US011167017B2

(12) United States Patent
de la Fuente Garcia et al.

(10) Patent No.: US 11,167,017 B2
(45) Date of Patent: Nov. 9, 2021

(54) SEA LICE VACCINE

(71) Applicant: Pharmaq AS, Overhalla (NO)

(72) Inventors: Jose de Jesus de la Fuente Garcia, Overhalla (NO); Marinela Contreras Rojo, Overhalla (NO); Margarita Maria Villar Rayo, Overhalla (NO); Marius Andre De Feijter Karlsen, Overhalla (NO); Bjorn Erik Brudeseth, Overhalla (NO); Karine Lindmo Yttredal, Overhalla (NO); Christer Ross Wiik-Nielsen, Overhalla (NO); Rolf Hetlelid Olsen, Overhalla (NO); Liv Blom Hungerholdt, Overhalla (NO)

(73) Assignee: Pharmaq AS, Overhalla (NO)

( * ) Notice: Subject to any disclaimer, the term of this patent is extended or adjusted under 35 U.S.C. 154(b) by 0 days.

(21) Appl. No.: 16/323,892

(22) PCT Filed: Aug. 16, 2017

(86) PCT No.: PCT/US2017/047095
§ 371 (c)(1),
(2) Date: Feb. 7, 2019

(87) PCT Pub. No.: WO2018/035199
PCT Pub. Date: Feb. 22, 2018

(65) Prior Publication Data
US 2019/0167772 A1 Jun. 6, 2019

Related U.S. Application Data

(60) Provisional application No. 62/376,016, filed on Aug. 17, 2016.

(51) Int. Cl.
*A01K 61/13* (2017.01)
*A61K 39/00* (2006.01)
*A61P 33/14* (2006.01)
*A61K 9/00* (2006.01)
*A61K 39/39* (2006.01)

(52) U.S. Cl.
CPC .......... *A61K 39/0003* (2013.01); *A01K 61/13* (2017.01); *A61K 9/0019* (2013.01); *A61K 39/39* (2013.01); *A61P 33/14* (2018.01); *A61K 2039/54* (2013.01); *A61K 2039/552* (2013.01); *A61K 2039/55516* (2013.01)

(58) Field of Classification Search
CPC .................................................. A61K 39/0003
See application file for complete search history.

(56) References Cited

U.S. PATENT DOCUMENTS

2013/0280290 A1\* 10/2013 Carpio Gonzalez .... A61P 33/14
424/191.1

OTHER PUBLICATIONS

Boslego et al (Chapter 17, Gonorrhea Vaccines, pp. 211-223, Vaccine and Immunotherapy) (Year: 1991).\*
Plotkin et al (Vaccines W. B. Saunders Company, p. 571) (Year: 1988).\*
Boxaspen et al (Journal of Marine Science vol. 63, pp. 1304-1316) (Year: 2006).\*
Struck (Nature Biotechnology vol. 14, pp. 591-593) (Year: 1996).\*
Cyrus Chothia and Arthur M. Lesk, "The relation between the divergence of sequence and structure in Proteins," The EMBO Journal, vol. 5, No. 4, pp. 823-826, 1986.

\* cited by examiner

*Primary Examiner* — Albert M Navarro
(74) *Attorney, Agent, or Firm* — Vyacheslav Vasilyev

(57) ABSTRACT

The present invention describes vaccine compositions for treatment and/or prevention against sea lice infestation in salmon. The present invention further describes nucleic acids, host cells, vectors and methods of using said vaccine for the prevention and/or treatment of sea lice infestation in salmon.

16 Claims, 22 Drawing Sheets
Specification includes a Sequence Listing.

FIGURE 1A

MREEVPQRAIKADKLGFLARDANMVKMAKALEKGRSVSRDIGGSDPERMAPPRVEEYVRSVFKDSGVKIEVV
AGHDTFEKEYPCLAAVNRAASTVARHQGRVIWLTYEPEGKVEKTAMIVGKGITYDTGGADIKAGGIMAGMSRD
KCGAADAAGFMKTISELKPKNLKVVVGMAMVRNSVGSNCYVSDEIITSRAGVRIRVGNTDAEGRMAMVDVLC
HMREKALREVN (SEQ ID NO. 1)

FIGURE 1B

ATGAGGGAAGAGGTGCCACAAAGGGCGATCAAGGCAGATAAGTTGGGATTTTTGGCCAGGGACGCTAAT
ATGGTGAAGATGGCTAAGGCATTGGAGAAAGGGAGATCCGTATCTAGAGACATTGGAGGCTCTGATCCTG
AAAGAATGGCACCACCTCGTGTGGAGGAATACGTTCGTTCAGTCTTTAAGGACTCTGGTGTTAAAATTGAG
GTTGTTGCAGGACACGACACCTTTGAAAAGGAGTATCCGTGCCTTGCTGCTGTGAATCGTGCAGCATCCA
CTGTAGCTCGTCATCAAGGACGTGTTATTTGGTTGACATATGAGCCTGAAGGAAAGGTAGAAAAGACAGC
CATGATTGTAGGAAAGGGTATCACTTATGATACCGGTGGAGCTGATATCAAGGCTGGCGGAATCATGGCT
GGAATGTCCAGGGACAAATGTGGAGCCGCAGATGCTGCTGGATTCATGAAAACCATTTCAGAATTGAAGC
CAAAGAACTTGAAGGTCGTTGTTGGAATGGCTATGGTGCGGAATAGTGTTGGATCCAATTGCTATGTGTCT
GATGAAATAATTACCTCTCGTGCTGGAGTAAGGATTCGTGTGGGTAACACGGATGCTGAGGGTCGAATGG
CCATGGTAGATGTTCTCTGCCACATGAGAGAAAAGGCTTTAAGAGAAGTTAAT (SEQ ID NO.2)

MAAIRKKLVIVGDGACGKTCLLIVFSKDQFPEVYVPTVFENYVADIEVDGKQVELALWDTAGQEDYDRLRPLSY
PDTDVILMCFSIDSPDSLENIPEKWTPEVKHFCPNVPIILVGNKKDLRNDPNTIKELGKMKQEPVKPEDGRTMAE
KINAFAYLECSAKSKEGVREVFETATRAALQVKKKKKRPCVL  (SEQ ID NO.3)

FIGURE 2B

ATGGCTGCTATTCGAAAGAAGTTGGTCATTGTTGGGGATGGAGCCTGCGGTAAGACTTGTCTCCTCATCG
TCTTCAGTAAAGATCAGTTCCCAGAAGTCTACGTCCCAACCGTGTTTGAAAACTATGTGGCCGACATCGAA
GTGGATGGAAAGCAGGTGGAACTGGCGCTCTGGGATACTGCAGGCCAAGAAGACTATGATCGCCTTCGT
CCTTTATCGTATCCGGACACGGATGTTATTCTCATGTGTTTCTCTATTGACTCTCCGGACTCCCTTGAGAA
CATTCCAGAGAAATGGACGCCGGAAGTCAAACATTTTTGCCCCAATGTACCTATAATACTCGTGGGGAAC
AAAAAGGATCTTAGAAATGACCCAAACACGATAAAAGAATTGGGGAAAATGAAGCAAGAGCCAGTCAAAC
CCGAAGACGGTCGCACAATGGCGGAAAAAATCAACGCATTTGCTTATTTGGAATGTTCCGCTAAATCTAAG
GAAGGGGTCAGAGAGGTCTTCGAAACTGCTACCCGAGCCGCGTTGCAAGTGAAGAAAAAGAAGAAGAGA
CCTTGCGTTCTA  (SEQ ID NO. 4)

MADRNTEFELEELLQFKKSHEHEFSSATRTAEQAIEITKNNIAWMDSSYKTIQEWLNK (SEQ ID NO. 5)

FIGURE 3B

ATGGCTGACAGGAATACGGAGTTTGAACTTGAAGAGCTACTTCAATTTAAAAAATCTCACGAACATGAGTT
TAGTTCAGCAACTCGTACCGCAGAGCAAGCTATTGAAATAACGAAGAATAATATCGCCTGGATGGACTCC
AGCTATAAAACCATTCAAGAGTGGTTGAATAAA (SEQ ID NO. 6)

MMSMNGRLAFAIAAGAFGSSFQHGYNTGVLNAPQVLITNWLRGCEKNMTAVTEDGSDVLVCEKDMKS (SEQ ID NO. 7)

FIGURE 4B

ATGATGTCCATGAATGGAAGATTGGCTTTTGCTATAGCAGCCGGTGCATTTGGATCTTCTTTTCAACATGG
ATATAATACCGGAGTTTTGAATGCTCCTCAAGTTCTTATTACGAATTGGTTGAGAGGATGTGAGAAAAATAT
GACAGCAGTTACAGAGGATGGAAGTGACGTTCTTGTCTGTGAGAAAGATATGAAAAGC (SEQ ID NO.8)

MYICDSEGNVICVDGWSYPSKLCSEPICDMNGRGCVNGKCIHPNVCACEVGWDGPNCDECIPLGGCKHGSC
N (SEQ ID NO. 9)

FIGURE 5B

ATGTACATTTGCGATTCGGAAGGAAATGTCATCTGTGTTGATGGATGGTCTTATCCATCTAAACTCTGTAG
TGAACCTATCTGTGATATGAATGGAAGAGGATGCGTTAATGGAAAATGCATCCATCCAAATGTATGCGCAT
GTGAAGTTGGATGGGATGGCCCTAACTGTGATGAATGTATTCCTCTTGGTGGTTGTAAGCATGGAAGCTG
TAAC (SEQ ID NO. 10)

MNEHVCSLFIYTDPFLWRHIYRSMKGSKRAERTRLKIEKLLTESVTRVNEAFSMAEFYGSGQTIHKGVHFSLLD
YIIDDDTRCFSDTEYCDEKVMPMGEMCNEPIVCDNLKHVFCNNLTSLRFYLHAFSAFRNHGAFCLSYAFTYRN
MSDFQGIAWVKGYDQSDERSLSHYGYCSLNDEKCQDESLQYYFRNTGVVNFHRLGENFSTSIGANVFIHEIGH
SLGSTHDDKVSECNPQGHDLYLMTGKAENILLQRNSDRLSACSSREIGRNLD (SEQ ID NO.11)

FIGURE 6B

ATGAATGAACATGTCTGCAGTTTGTTCATCTACACAGATCCATTTCTCTGGAGACACATTTATCGCTCTATG
AAAGGAAGTAAAAGAGCAGAAAGGACGAGGCTCAAAATTGAAAAATTACTCACAGAATCCGTAACAAGAG
TAAATGAGGCATTCTCTATGGCTGAGTTTTATGGGTCTGGTCAGACCATACATAAGGGAGTTCACTTTTCC
TTACTGGATTATATCATCGACGACGACACAAGATGCTTCTCAGACACGGAATATTGTGATGAAAAAGTCAT
GCCCATGGGAGAAATGTGCAATGAGCCCATCGTATGTGACAACTTGAAGCATGTCTTTTGTAACAACTTAA
CAAGTCTACGTTTCTATCTCCATGCTTTTCCGCATTTCGCAACCATGGAGCATTTTGTCTTTCATATGCGT
TTACATATAGGAACATGAGTGATTTTCAAGGGATTGCATGGGTAAAGGGATATGATCAAAGCGATGAGCG
CTCTTTGAGTCACTATGGATATTGCTCATTGAATGATGAAAAGTGTCAGGATGAGAGTCTCCAATATTATTT
CAGGAACACGGGTGTAGTCAATTTTCATAGATTAGGAGAAAATTTTTCAACGTCAATTGGAGCAAATGTAT
TTATACATGAAATTGGTCATAGTTTAGGAAGCACACACGACGATAAAGTGAGTGAGTGCAATCCGCAGGG
CCATGACTTGTATCTTATGACGGGAAAGGCTGAGAACATATTACTTCAGCGAAACAGCGATCGGCTTTCTG
CATGCTCAAGTCGGGAAATTGGAAGGAACTTGGAT (SEQ ID NO.12)

MENSRADVPNIEDKIPPKIEEDNELQGNSLTVPKSSNRESSNVRRMHTAVRLNEVIVNKSHDAKLVILNLSPPK
IMGPDKDASYMEFLEVLTEGLERVLMVRGGGREVITIYS (SEQ ID NO. 13)

FIGURE 7B

ATGGAGAATAGTCGAGCTGATGTTCCAAACATTGAAGACAAAATACCACCCAAGATTGAAGAAGATAATGA
GTTACAAGGCAACTCTCTCACAGTACCAAAGTCTTCAAATCGTGAGTCTTCTAACGTCAGACGGATGCATA
CTGCCGTACGATTGAACGAAGTGATTGTCAACAAGTCCCACGATGCAAAATTAGTAATTTTGAATCTTCCA
AGTCCTCCCAAAATTATGGGTCCAGACAAAGATGCTAGCTATATGGAATTTTTAGAAGTTTTAACCGAGGG
TTTAGAGCGAGTCCTTATGGTTCGAGGAGGCGGACGAGAAGTGATTACCATTTACTCT (SEQ ID NO. 14)

MEFLGGFTINLAFITNGFALAYPTIALSQLTNNGTESCSFVMSKEEGSWFAGLLGIGGICGSVFFGTLIGQRIGN
RKTLLLAAILDIIGWLLIAFAVNSPMMMGGRFLNGVFVGTIGPSGYTFLSEIMHRKHRASCSQATSVAISAGMLV
TYGLGSVISWNLLAIGCGISSVLFFIMLLTMPDSPYWNASIGKIEEAKKSLSHFRSKKDDVEEEFKEIMEGIQKSIK
KEKISFFEAMKLLFTDETCYKPFIILSVLFLIQTLSGLYAVIAYAIQVLEESRTPIDTNLGTIISGAMRLFFGTLAIPLF
FYLPRKTLMYISTGLACLSISSLGILGLLELETNTFTTYFPVGAISLYMVSFTFGFQSIPFLYLGEYYPPHVRQHLA
GLTSTLRFLGFFIMLKLFPQMMEFFGPNYTFIFLGLVCLFAGIYAKVVLPETKGLTLNQIQDLF (SEQ ID NO. 15)

FIGURE 8B

ATGGAGTTTTTAGGTGGATTTACGATTAATCTTGCATTTATTACTAATGGATTTGCCTTGGCCTATCCCACA
ATTGCATTGAGTCAACTCACCAATAATGGTACTGAATCATGCTCATTTGTTATGAGCAAGGAAGAGGGATC
CTGGTTCGCTGGACTTTTGGGCATCGGAGGTATTTGTGGGAGTGTGTTCTTCGGAACTTTGATTGGCCAA
AGAATTGGTAATCGAAAGACTCTCCTCTTGGCAGCTATTTTAGACATTATTGGATGGCTTCTTATTGCATTT
GCTGTGAATTCTCCAATGATGATGGGAGGACGATTTTTAAATGGTGTTTTTGTTGGCACAATAGGCCCTAG
TGGATACACCTTCCTATCAGAAATAATGCATCGTAAACATCGAGCTTCTTGTTCACAAGCAACTTCTGTTGC
AATTAGTGCTGGGATGCTAGTCACTTATGGACTAGGGTCTGTGATTTCATGGAACCTCCTTGCGATTGGAT
GTGGTATTTCTTCAGTTCTGTTCTTTATCATGTTACTTACAATGCCAGACTCTCCATATTGGAATGCCTCTA
TCGGAAAAATTGAGGAAGCCAAGAAATCTTTAAGTCATTTCAGGTCAAAGAAGGACGATGTGGAAGAAGA
GTTCAAAGAAATCATGGAAGGAATACAAAAATCCATCAAAAAAGAAAAGATTTCATTCTTCGAGGCTATGAA
GTTACTCTTCACGGATGAGACATGCTACAAACCTTTCATAATATTAAGCGTTTTGTTCTTAATTCAAACCCT
TTCTGGGTTGTATGCAGTTATTGCTTATGCTATTCAAGTATTGGAAGAGTCCAGGACTCCTATTGATACAAA
TTTGGGCACAATTATCTCCGGAGCAATGCGACTTTTTTTTGGAACTCTTGCAATTCCCCTCTTCTTTTATCT
ACCTCGTAAAACACTAATGTACATTTCCACTGGCCTTGCTTGTCTCTCTATTTCCTCTCTGGGCATTTTGGG
TCTCCTAGAATTGGAAACAAATACATTTACCACATATTTCCCCGTTGGTGCAATTTCTTTATATATGGTGTC
ATTTACATTTGGATTCCAGAGCATTCCTTTCCTCTATCTTGGAGAGTATTATCCACCTCATGTGAGACAGCA
CTTGGCAGGCTTAACCTCCACCTTAAGATTCTTAGGGTTTTTTATCATGCTCAAATTATTTCCTCAAATGAT
GGAGTTCTTTGGACCAAATTATACATTTATATTCCTAGGACTTGTATGTCTCTTTGCTGGAATTTACGCCAA
AGTAGTTCTCCCTGAGACAAAGGGGCTTACTCTGAATCAAATTCAAGACCTATTC (SEQ ID NO. 16)

MYSGVQALTHLLEEVRVPYKVWILGEDSLDTLPWKEFALLLFQDFKTFVSINLFTRKLIFKYCSEYSVGIIVSATH
QTPLPLKITNDSIFQRHNSLRNLFICPHSQIPNILKASRTLYETLDSYGFLSFTSRFLTKSTTPVLEAMSDSGPVTI
VLHDRGQVPKIIFASNPLSHWLLKLLFLDSITFLSHQLINLDTKRWVLIDVDDIFVGKNRLSPSDVRELVISQDKLR
KNIYGFKYNLGFSGYYFRNQGSSLINKEGDAALIEKKHHFWWFPHTFRHLQPHMFNSSLQLEQQMFLNKKFAL
EYKLPVNFHYAVAPHHSGVYPVHKPLYDAWKNVWGIVVTSTEEYPHLKPSRLRRGFTHDKLKILPRQTCGLFT
KNIYYEDYPKNPEVLEKSIRGGELFQTISFNSINIFMTHMSNYGFDRLAPYTFESVFSMLKCWTNLKFVTVNPEK
LSEIYFNMFPDEKVPIWGNPCYDSRLKEIWSKNKNCKRLPNFLVIGPQKTGTTALYNFLKIHPSIISNNHHSKYFE
EVQFFSSSDYLKGFE (SEQ ID NO. 17)

FIGURE 9B

ATGTACTCTGGTGTCCAAGCATTGACTCACCTCTTGGAAGAAGTCCGTGTTCCCTACAAAGTGTGGATTTT
GGGAGAGGACTCCTTGGACACCCTACCTTGGAAGGAATTCGCCCTTCTTCTCTTCCAGGATTTTAAAACCT
TCGTTTCTATCAACTTGTTCACTCGAAAATTGATATTTAAATATTGTTCAGAATATTCTGTCGGTATCATTGT
ATCCGCCACCCATCAAACGCCTCTTCCTTTAAAAATTACCAATGATTCCATTTTTCAACGTCATAATTCACT
TAGAAATTTATTTATTTGTCCTCATAGTCAAATTCCTAATATTCTAAAAGCGTCTCGTACTCTCTATGAAACT
CTTGACTCTTACGGGTTCTTATCATTTACTTCTCGTTTTCTCACTAAATCTACTACCCCTGTCCTTGAGGCG
ATGTCTGATTCCGGGCCTGTTACTATAGTTCTTCATGATAGAGGACAAGTACCAAAGATTATCTTTGCTTCA
AATCCTTTGAGTCACTGGCTTTTAAAGCTACTTTTCCTAGACTCTATTACTTTTTTGAGTCATCAACTTATTA
ACTTAGACACTAAAAGGTGGGTTCTCATAGATGTTGACGATATTTTCGTCGGCAAAAACCGGCTTTCTCCA
TCTGATGTTAGAGAGCTTGTTATCTCTCAAGATAAACTTCGTAAGAATATTTATGGATTTAAATATAACCTG
GGATTTTCTGGCTATTATTTCCGTAACCAAGGTTCATCTTTAATAAATAAAGAAGGTGATGCCGCCCTCATT
GAAAAAAAACACCATTTTTGGTGGTTCCCCCATACATTCAGACATTTACAACCTCATATGTTCAATTCCTCA
CTTCAACTTGAACAGCAGATGTTTCTTAATAAGAAATTTGCGCTGGAATACAAATTGCCGGTCAATTTCCAT
TATGCCGTTGCTCCCCATCATTCTGGTGTTTACCCTGTTCATAAGCCATTATATGATGCTTGGAAAAATGTC
TGGGGGATAGTTGTTACTTCCACAGAGGAATATCCTCACCTTAAACCATCTCGATTACGTCGTGGATTTAC
ACATGATAAATTAAAAATTCTTCCGAGGCAAACATGTGGTCTCTTTACTAAAAACATTTATTATGAAGATTAC
CCTAAAAATCCTGAAGTGTTGGAAAAATCTATCAGAGGTGGAGAACTGTTTCAGACTATTTCATTTAATTCT
ATAAATATATTCATGACACATATGTCCAATTATGGATTTGATAGACTGGCTCCGTATACTTTTGAATCTGTAT
TTTCCATGTTAAAATGCTGGACTAACCTAAAATTTGTTACAGTTAATCCGGAAAAGCTAAGTGAAATTTATTT
TAATATGTTTCCTGACGAGAAAGTTCCAATTTGGGGAAATCCTTGTTATGACAGTCGCCTTAAAGAAATCT
GGTCGAAAAATAAAAATTGTAAGAGGCTACCTAATTTTCTTGTGATTGGACCGCAAAAAACTGGAACAACG
GCTTTATATAATTTCCTAAAAATTCATCCTTCAATAATTTCTAACAATCATCACTCCAAATATTTTGAAGAAGT
ACAATTTTTCAGTAGTAGCGATTATCTTAAAGGTTTCGAG (SEQ ID NO. 18)

MEFYFGGNPIKCDCQMTWFKSINSVNGLQMFPTVADLESIYCELVYSREQSFVPLVEAESDNFLEYKAHCFAL
CQCCEYDACDCEMTCPSNCTCYHDNSWAKNIAECSFSNLKGLPDRLPMDATEIFLDGNEISVVQSHTFIGRKN
LKILYLNESQVRYLPNNSFNGLIALEELHLENNHITRLEGSEFNGLFRLNKLYLHKNKISFVNNFTFKELKALETLY
IHGNHISIFPPWVFFQNPLLATLTLSENPWNCDCNYMKRFENWIEGFHGKILDLYYVSC (SEQ ID NO. 19)

FIGURE 10B

ATGGAATTTTACTTTGGCGGAAACCCTATTAAATGTGATTGTCAAATGACATGGTTCAAAAGTATTAACTCA
GTTAATGGTCTACAAATGTTCCCTACTGTTGCTGATCTTGAGTCAATTTATTGTGAACTTGTTTATTCTCGT
GAACAGAGTTTTGTGCCACTTGTGGAAGCAGAAAGTGACAATTTTCTCTGTGAATACAAGGCACATTGTTT
TGCTCTATGCCAATGTTGTGAATATGATGCTTGCGATTGTGAAATGACTTGCCCTTCCAATTGCACTTGCT
ACCATGACAATTCTTGGGCTAAGAATATTGCTGAATGCTCATTTTCTAACCTGAAAGGACTTCCTGATCGTT
TGCCAATGGATGCTACAGAAATATTTTTAGATGGAAATGAAATTAGTGTAGTGCAGAGTCATACGTTATC
GGTCGGAAGAACCTTAAGATATTATACTTGAATGAATCTCAAGTAAGATATCTGCCCAATAATTCATTTAAT
GGATTGATAGCACTCGAAGAACTACATTTAGAAAATAATCATATCACAAGGCTGGAAGGAAGTGAATTCAA
CGGGTTGTTTCGTCTAAATAAACTTTATTTACACAAAAATAAGATAAGTTTTGTCAACAACTTTACATTTAAA
GAGTTAAAAGCATTAGAGACTCTTTATATTCACGGAAATCACATTTCCATTTTCCCACCTTGGGTATTTTTT
CAAAATCCATTGCTGGCTACTCTTACTCTCTCTGAAAACCCATGGAATTGTGACTGTAATTATATGAAACGA
TTCGAAAATTGGATTGAGGGATTTCATGGTAAAATCTTGGATTTGTACTATGTATCTTGT (SEQ ID NO. 20)

MILIQSYVYLDAQNTAQHILYMDQASLGLLRINFVDSEKYKEIIKAYRTLQSSTAETLFKYLDINKPDDDKLNEDLE
SMFQFEKAIAGIMVPEDQRRNSTAMYNPMSLAKIMKSYTQIKWKIYFNELLKGDNAIEENDKIIVAEPYYFEKLN
ELLNETDDKIIYNYIHWRILLQTLPNGPDEMREHYKTFLKDAMGIKKEVLRDNICAKRVAAPFDGMGGLGFAVAY
EYIQKKFDDDSKNEVKKMVGGLKSSFKELVAESSWMDKETQNKAKEKVDSMVQSLGYPDWLKTESEIEKKYK
ELDELKPKTLLENIKKVRQFESLTSFSAINSKPDKNAWPLHPAVVNAVYSPMRNSITFPAGILQYPFFESSNPMY
LNFGSIGVVIGHEITHGFDDQGSQYDNNGNLVKWWSNSSLEAFQKEKECIIEQYSAFNVPEISEETYVNGVLTQ
GENIADNGGLRESFRAYKKWVNSNNDEPKLPELEKYTSEQMFFIAYSQTWCQVKTKASLQNQILSDPHSPGKF
RSWGPVSNSKSFSKAFNCKPSDPMNNGENSCVLW (SEQ ID NO.21)

FIGURE 11B

ATGATCCTGATCCAGAGCTACGTTTACCTGGATGCGCAGAACACGGCGCAGCACATCCTGTACTGGACCA
AGCGAGCTTAGGGCTCCTGAGAATTAACTTTGTGGATAGTGAGAAGTACAAAGAGATAATTAAGGCGTAC
CGTACCCTGCAGAGCTCCACCGCGGAAACCCTGTTCAAATACTTGGATATTAATAAACCTGACGATGACA
AACTGAACGAAGATCTGGAATCTATGTTCCAGTTCGAAAAGCAATCGCTGGCATCATGGTGCCGGAAGA
TCAGCGTCGTAACTCTACCGCGATGTACAACCCGATGTCGCTGGCGAAAATCATGAAATCTTACACCCAG
ATCAAATGGAAAATCTACTTCAACGAACTGCTGAAAGGCGACAACGCAATCGAAGAAACGATAAAATCAT
AGTGGCAGAACCGTACTACTTCGAAAAACTGAACGAACTGCTGAACGAAACCGACGACAAAATTATCTATA
ACTATATCCACTGGCGTATCCTGCTGCAGACCCTGCCGAACGGCCCGGACGAAATGCGTGAACACTACA
AAACCTTCCTGAAAGATGCGATGGGTATTAAAAAAGAAGTTCTTCGTGATAACATCTGCGCAAAACGCGTT
GCCGCTCCGTTCGACGGCATGGGTGGTCTGGGCTTCGCAGTTGCGTACGAATACATTCAGAAAAAATTCG
ACGACGACTCCAAAAACGAAGTTAAGAAAATGGTTGGTGGTCTGAAAAGCAGCTTCAAAGAACTGGTTGC
GGAAAGCTCCTGGATGGATAAAGAAACTCAGAACAAAGCTAAAGAAAAGTGGATTCCATGGTTCAGTCC
CTGGGTTACCCGGACTGGCTGAAAACCGAATCTGAAATCGAGAAAAAATATAAAGAACTGGATGAACTGA
AACCGAAAACCCTGCTGGAAAACATTAAAAAAGTTCGTCAGTTCGAAAGCCTGACTTCTTTCAGCGCGATC
AACAGCAAACCGGATAAAAACGCATGGCCGCTGCACCCGGCGGTGGTTAACGCGGTTTATAGCCCGATG
CGTAACTCTATTACCTTCCCGGCGGGCATCCTGCAGTACCCGTTCTTCGAATCTAGCAACCCGATGTACC
TGAACTTCGGGAGCATCGGCGTGGTTATCGGCCACGAAATCACCCACGGTTTCGACGACCAGGGCAGCC
AGTACGATAACAACGGTAACCTGGTGAAATGGTGGTCCAACTCCAGCCTGGAAGCCTTTCAGAAAGAAAA
AGAATGCATCATCGAACAGTACAGCGCGTTCAACGTTCCGGAAATCTCCGAAGAAACCTACGTTAACGGC
GTTCTGACCCAGGGCGAAAACATCGCGGATAACGGCGGCCTGCGTGAATCCTTCCGTGCGTATAAAAAAT
GGGTGAACTCCAACAACGACGAACCGAAACTGCCGGAACTGGAAAAATACACCAGCGAACAGATGTTCTT
CATCGCTTACTCCCAGACCTGGTGTCAGGTTAAAACCAAAGCAAGCCTGCAGAACCAGATCCTGAGCGAC
CCGCACTCTCCGGGCAAATTCCGCAGCTGGGGCCCGGTGTCTAACTCTAAAAGCTTCAGCAAAGCGTTC
AACTGCAAACCGAGCGATCCGATGAACAACGGCGAAAACAGCTGCGTGCTGTGG (SEQ ID NO.22)

MPMGVLACKSFSTSSKVGAAGGAEVSSILEERILGSAPKANLEETGRVLSIGDGIARVYGLKNIQAEEMVEFSS
GLKGMALNLEADNVGVVVFGNDKLIKEGDVVKRTGAIVDVPVGRELLGRVVDALGNPIDGAGPVNTATRQRVG
IKAPGIIPRQSVKEPMQTGIKAVDSLVPIGRGQRELIIGDRQTGKTAVAIDAIINQKRFNDAGDEKKKLYCIYVAIG
QKRSTVAQIVKRLTDTDAMKYSIVVSATASDAAPLQYLAPYSGCAMGEFFRDNGMHALIIFDDLSKQAVAYRQ
MSLLLRRPPGREAYPGDVFYLHSRLLERAAKMSDTQGGGSLTALPVIETQAGDVSAYIPTNVISITDGQIFLETE
LFYKGIRPAINVGLSVSRVGSAAQTKSMKQVAGSMKLELAQYREVAAFAQFGSDLDAATQQLLNRGVRLTELL
KQGQYVPMAIEDQVAVIYCGVRGFLDKLDPAKITDFEKKFLEHVRSSQKPLLDQIAKDGHLSDTSDKALHKVVV
DFLATYQ (SEQ ID NO.23)

FIGURE 12B

ATGCCGATGGGCGTTCTGGCGTGCAAATCTTTCAGCACCTCTTCTAAAGTTGGCGCGGCAGGCGGCGCT
GAAGTTTCTAGCATCCTGGAAGAACGTATCCTGGGTAGCGCCCCGAAAGCTAACCTGGAAGAAACCGGT
CGCGTTCTGTCTATTGGTGATGGCATTGCGCGCGTTTATGGCCTGAAAAACATCCAGGCGGAAGAAATGG
TTGAATTCAGCAGCGGTCTGAAAGGCATGGCGCTGAACCTGGAAGCTGATAACGTTGGCGTGGTTGTTTT
CGGTAACGATAAACTTATTAAAGAAGGTGATGTTGTTAAACGTACCGGTGCTATCGTTGACGTGCCGGTTG
GTCGTGAACTGCTGGGCCGTGTTGTGGATGCCCTGGGAAACCCAATCGATGGCGCGGGTCCGGTGAAC
ACCGCGACCCGCCAGCGCGTGGGTATCAAAGCGCCGGGTATCATCCCGCGTCAGTCTGTAAAAGAACCG
ATGCAGACCGGCATTAAAGCGGTTGACTCTCTGGTTCCGATTGGCCGCGGCCAGCGTGAACTGATCATT
GGCGACCGTCAGACTGGCAAAACCGCGGTTGCCATCGACGCTATCATCAACCAGAAACGTTTCAACGAT
GCGGGCGATGAAAAGAAAAAACTGTACTGCATTTACGTTGCTATCGGTCAGAACGTTCTACCGTTGCGC
AGATCGTTAAACGTCTGACCGACACCGACGCAATGAAATACTCTATTGTTGTTAGCGCGACCGCCAGCGA
TGCTGCGCCGCTGCAGTACCTGGCTCCGTACAGCGGCTGTGCTATGGGGGAATTCTTCCGTGATAACGG
TATGCATGCTCTGATCATCTTCGATGATTTATCTAAACAGGCTGTAGCCTACCGTCAGATGAGCTTGCTGC
TGCGTCGCCCGCCGGGCCGTGAAGCGTATCCAGGTGATGTTTTCTACCTGCACTCTCGCTTGCTGGAGC
GTGCTGCGAAAATGAGCGACACCCAGGGTGGTGGTTCCCTGACCGCACTGCCGGTGATCGAAACCCAG
GCGGGCGATGTTAGCGCTTACATCCCGACCAACGTGATCAGCATTACCGATGGCCAGATTTTCCTGGAAA
CCGAACTGTTCTACAAAGGCATCCGTCCGGCCATCAACGTGGGTCTGTCCGTGAGCCGCGTTGGTTCCG
CGGCACAGACCAAATCCATGAAACAGGTTGCGGGTAGCATGAAACTGGAACTGGCACAGTACCGTGAAG
TTGCAGCCTTCGCGCAGTTCGGCTCTGATCTGGACGCTGCAACCCAGCAGCTGCTGAACCGTGGTGTTC
GTCTGACCGAACTGCTGAAACAGGGCCAGTACGTTCCGATGGCGATTGAAGATCAGGTTGCTGTGATCTA
CTGCGGCGTTCGTGGTTTCCTGGACAAACTGGATCCGGCGAAAATTACCGATTTCGAGAAAAAATTCCTG
GAACACGTGCGTAGCAGCCAGAAACCGCTGCTGGACCAGATCGCTAAAGATGGCCACCTGAGCGATACC
TCCGATAAAGCTCTGCATAAAGTTGTTGTTGACTTCCTGGCGACCTATCAG (SEQ ID NO.24)

VELSVKCKDITNKDMMSKSDPICLVKQKTGVDKFEELGRTEQIKDCLSPEFMKKIVVPYNFEERQELRFELWDV
DNIKKKVEDQKLLGYVDVSLGKIVNARGIEAKIEKGKGSMIIVAKEASSEQSSIGKLHLQFGASKLENKDTFGKS
DPFFHISKSISATDFMKVYESEWIKNDLNPTWKPFSMSLNDLCDGELNRLLKIDVFDYSSNGKHDFIGEFETSVS
QMMNKRSFEVINPKKKEKKKYTNSGVLNIISFNNDSPPSFLDFIQGGMVMNFSVAIDFTASNGNIRSRLSLHHR
GDEGENDYTVAIQTVGDIIEDYDTDKKFPAFGFGARLPPNGEISHDFFLNLKENNPFCEGVRGILDAYYSTVDA
VELYGPTNFSPCINRIKAIAQSHQDGKQYYVLLILTDGAITDMAETKKTIVEASNLPMSIIIGVGSADFSSMIELDS
DDALLKDEDGNVAARDIVQFVEMAKYVKKAENGDIFWDRASLAYQVMVEIPKQVLEWTSKRGIKP (SEQ ID NO. 25)

FIGURE 13B

GTGGAACTGAGCGTCAAATGCAAAGATATCACCAACAAAGATATGATGTCCAAAAGCGATCCGATCTGCC
TGGTTAAACAGAAAACCGGCGTTGACAAATTCGAAGAACTGGGCCGTACGGAACAGATCAAAGACTGCCT
GAGCCCGGAATTTATGAAGAAAATCGTTGTTCCGTACAACTTCGAAGAACGCCAGGAACTGCGCTTCGAA
CTGTGGGATGTCGATAACATCAAGAAAAAAGTTGAAGACCAGAAACTGCTGGGCTATGTTGATGTTAGCC
TGGGCAAAATCGTGAACGCGCGTGGAATCGAAGCGAAAATCGAAAAAGGTAAAGGCAGCATGATCATCG
TTGCGAAAGAAGCGTCCTCTGAACAGAGCAGCATCGGCAAACTGCATCTGCAGTTCGGCGCGAGCAAAC
TGGAAAACAAAGATACCTTTGGTAAATCCGACCCGTTCTTCCATATCTCTAAAAGCATCAGCGCGACCGAC
TTTATGAAAGTTTACGAATCCGAATGGATCAAAAACGATCTGAACCCGACCTGGAAACCGTTCTCTATGTC
GCTGAACGACCTGTGCGACGGCGAACTGAACCGTCTGCTGAAAATCGACGTTTTCGATTATAGCTCTAAC
GGCAAACACGACTTCATCGGCGAATTCGAAACCAGCGTGTCCCAGATGATGAACAAACGGAGCTTCGAA
GTTATCAACCCGAAGAAAAAGAAAAGAAAAAATACACCAACAGCGGTGTGCTGAACATCATCAGCTTTAA
CAACGACAGCCCGCCGTCCTTCCTGGATTTCATCCAGGGCGGTATGGTTATGAACTTCAGCGTTGCCATC
GATTTCACTGCGTCTAACGGTAACATCCGTTCTCGTCTGTCCCTGCACCATCGTGGCGACGAAGGTGAAA
ACGATTACACCGTGGCCATCCAGACCGTTGGCGATATCATTGAAGACTATGATACCGATAAAAAATTCCCG
GCCTTCGGCTTCGGCGCGCGTCTGCCGCCGAACGGCGAAATCAGCCACGACTTCTTCCTGAACCTGAAA
GAGAACAACCCGTTCTGCGAAGGTGTGCGTGGCATCCTGGATGCGTACTACTCTACCGTCGACGCGGTT
GAACTGTACGGCCCGACCAACTTCTCCCCGTGCATCAACCGTATTAAAGCGATCGCGCAGAGCCACCAG
GATGGCAAACAGTACTACGTCCTGCTGATTCTGACCGACGGCGCGATCACCGACATGGCCGAAACCAAA
AAGACCATCGTGGAAGCGAGCAACCTGCCGATGTCTATCATCATCGGCGTGGGCAGCGCGGATTTC
TCATCTATGATCGAACTGGACAGTGATGATGCATTGTTAAAAGATGAGGATGGTAACGTTGCCGCTCGTG
ATATCGTTCAGTTCGTTGAAATGGCCAAATACGTGAAGAAAGCCGAAAACGGTGACATCTTCTGGGATCG
CGCTTCTTTAGCGTACCAGGTCATGGTAGAAATCCCGAAACAGGTGCTGGAGTGGACCTCTAAACGCGG
CATTAAACCG (SEQ ID NO. 26)

MPKAVNVRVTTIDAELEFAIQPNTTGKQLFDQVVKTIGLREIWFFGLQYTDTKGFSTWLKLNKKVMVQDVKKET
PLQFKFRAKFYPEDVAEELIQDITLRLFYLQVKNAILSDEIYCPPETSVLLASYAVQSKHGDFQKDFHVAGFLAN
DRLLPERVTQQHRLNREQWEKRITEWYSEHKGMMREDAMMEYLKIAQDLEMYGVNYFEIKNKKGTELWLGV
DALGLNIYEKDDRLTPKIGFPWSEIRNISFNDRKFVIKPIDAKAPNFVFFAPRLRINKRILTLCMGNHELYMRRRK
PDTIEVQQMKAQNKEEKLAKQQEREKLQREIAAREKAERIQAEYEDRLKAMQEDMEKRQKALLEAQEQIKKLE
SVLRETQDAKQELEESQNELKDMMRRLEDDKNLEIEERTRLQDEIARKQSEVNDIYTQVQTKEQENMELQKE
MDDARRKHEEATIALVAATTTPKHHHLEEDDNDDEVSNSERDLHVPSDPIDDPVSDRLLLVERNERLQNQLKS
LKEDLSHTRDEGEETTMDRIHKENVKQGRDKYKTLREVRKGNTKRRVDQFENM (SEQ ID NO. 27)

FIGURE 14B

ATGCCTAAAGCGGTGAACGTTAGAGTGACGACCATTGACGCTGAGCTTGAGTTCGCGATCCAGCCTAACA
CCACAGGTAAACAGCTGTTTGATCAGGTAGTGAAAACCATAGGTCTGCGTGAAATCTGGTTCTTCGGCCT
GCAGTACACCGATACCAAAGGTTTCTCTACCTGGCTGAAACTGAACAAAAAAGTGATGGTGCAGGATGTT
AAAAAAGAAACCCCGCTGCAGTTCAAATTCCGTGCAAAATTCTACCCGGAAGACGTGGCGGAAGAACTGA
TCCAGGACATTACCCTGCGTCTGTTCTATCTGCAGGTTAAAAACGCGATTCTGAGTGATGAGATCTACTGC
CCGCCTGAAACTAGCGTTCTGTTAGCTAGCTACGCGGTTCAATCTAAGCACGGTGACTTTCAAAAGATTT
CCATGTTGCGGGCTTCCTGGCGAACGATCGCCTGCTGCCGGAACGTGTTACCCAGCAGCACCGTCTGAA
CCGTGAACAGTGGGAAAAACGTATCACCGAATGGTATTCCGAACATAAAGGCATGATGCGCGAAGACGC
GATGATGGAATATCTGAAAATCGCGCAGGATCTGGAAATGTATGGCGTGAACTACTTCGAAATCAAGAAC
AAAAAAGGCACTGAACTGTGGCTGGGCGTGGACGCACTGGGCCTGAACATCTACGAAAAGATGATCGC
CTGACCCCGAAAATCGGTTTCCCGTGGAGCGAAATCCGTAACATCAGCTTCAACGACCGCAAATTCGTCA
TCAAACCGATTGATGCTAAAGCGCCGAACTTCGTGTTCTTCGCTCCGCGTCTGCGCATCAACAAACGTAT
CCTGACCCTGTGTATGGGCAACCACGAACTGTACATGCGTCGTCGCAAACCGGATACCATTGAAGTTCAG
CAGATGAAAGCACAGAACAAAGAAGAAAAACTGGCGAAACAGCAGGAACGTGAAAAACTGCAGCGTGAA
ATCGCGGCGCGTGAAAAAGCTGAACGCATCCAGGCGGAATACGAAGATCGTCTGAAAGCGATGCAGGAA
GATATGGAAAAACGTCAGAAAGCGCTGCTGGAAGCACAGGAACAGATCAAAAAACTGGAATCCGTTCTGC
GCGAAACCCAGGATGCGAAACAGGAACTGGAAGAATCTCAGAACGAACTGAAAGATATGATGCGTCGTCT
GGAAGACGACAAAAACCTGGAAATCGAAGAACGTACTCGCCTGCAGGACGAAATCGCCCGCAAACAGAG
CGAAGTTAACGATATCTACACCCAGGTACAGACCAAAGAACAGGAAAACATGGAACTGCAGAAAGAAATG
GATGACGCGCGTCGTAAACACGAAGAAGCGACTATCGCCCTGGTTGCGGCGACCACCACCCCGAAACAC
CATCACCTGGAAGAAGATGATAACGACGATGAAGTTTCTAACTCTGAACGCGACCTGCACGTGCCGAGCG
ACCCGATCGACGACCCGGTTTCTGATCGTCTGCTGCTGGTTGAACGTAACGAACGTCTGCAGAACCAGCT
GAAATCCCTGAAAGAAGACCTGAGCCACACCCGTGACGAAGGCGAAGAACCACCATGGACCGTATCCA
CAAAGAAAACGTTAAACAGGGTCGTGATAAATACAAAACCCTGCGTGAAGTTCGTAAAGGTAACACCAAAC
GTCGTGTTGATCAGTTCGAAAACATG (SEQ ID NO. 28)

MNVPSSVSLVLILASTCHALMFHLEPNGRKCLKEEINKDILVSGEYEVTEVPGQVVDLIVVDSKGQHFVSRQNA
DKGKFAFTTDETNDAFEVCFISQIPAGHHGSQQEIFLSVKHGVEAKSYEGLGDAAKLKPLEVELKRLEDLSESIV
QDFAHMRRREEEMRDTNESTNNRVLYFSIFSMCCLCSLATWQVLYLRKYFKSKKLIE (SEQ ID NO. 29)

FIGURE 15B

ATGAACGTTCCGAGCTCTGTTTCTCTGGTTCTGATCCTGGCGAGCACCTGCCACGCGCTGATGTTCCACC
TGGAACCGAACGGTCGCAAATGCCTCAAAGAAGAAATCAACAAAGATATCCTGGTAAGTGGTGAATATGA
AGTTACGGAAGTGCCTGGTCAGGTTGTTGACCTGATCGTAGTCGACTCTAAAGGTCAGCACTTTGTTTCC
CGCCAGAACGCAGATAAAGGTAAATTCGCGTTCACCACCGATGAAACCAACGACGCGTTCGAAGTTTGCT
TCATCAGCCAGATCCCGGCGGGTCACCACGGCTCTCAGCAGGAAATCTTCCTGAGTGTTAAACATGGTGT
TGAAGCGAAAAGCTACGAAGGACTGGGTGATGCGGCGAAACTGAAACCGCTGGAAGTTGAGCTGAAACG
TCTGGAAGATCTGTCGGAAAGCATCGTTCAGGATTTCGCGCACATGCGTCGTCGTGAAGAAGAAATGCGA
GATACCAACGAATCTACCAACAACCGTGTTCTGTACTTCAGCATCTTCAGCATGTGCTGCCTGTGCTCTCT
GGCGACCTGGCAGGTTCTGTACCTGCGTAAATACTTCAAATCTAAAAAACTTATCGAA (SEQ ID NO. 30)

MVDEIQEKDKEIYELLSRIKSQDMELEKLNANFEQWKGIKNDLENKISILQRDLDEKYGVVQENNTVIDGLKIELQKLTE
QKRECESFSNAEIQRIKETVEKLESENISIHQGIQEKDKAFALLEFQNKSLTQGNKQSIIHIDEMKALNTCLENKVKELQ
KNFELSSTRLDEANIKIAENEKEMNLVNTQLITVTDENQEWQHRFDELTNQNHSFAKEIEILKSSLDGENSKNNMDFKL
LEGKNRELESFLEKAQLRIEDQGSNIHNLQLKLKSKNEKFINLENNIIFSNEQKLQLLSDVESYKNTSRSKEDDIKELQQ
LVDSLNNEKRDLTTRCDAYSTKKLQMESDFNECKNELRICELNTKELQSCVKSYEIELENVKFQLGECSRLQSILDEE
RKKFEVEKIKYQEDILTHSRSNNEEIAQFKIKCDKLESEMSKLKHDDSEFVELKSANSELLSKITCLSSQITLLLSEKEKI
DEDLVRLTDSNEAVLQTKQHEIIELKEKINSILKDHKKEIEDTHNEYKEKMESSLYDGDSVKEEIASLQNLVKSKENDAN
LLNEQVNHKKEAITCLENRLSQEAVALSEVLNNNKKLVIEIEELKKLNCQLENNILEVSESQSKKEFDNLRQTLKSCKLE
LASTQVESTFKDKEIDTLRKDINFLSKKSNTYKEELRKVRNENMDTTIYNNESKLKKRNETKVERQNDAMHSV (SEQ ID NO. 31)

ATGGTTGACGAAATCCAGGAAAAAGACAAAGAAATCTACGAGCTGCTGTCCCGTATCAAATCCCAGGACATGGA
ACTCGAAAAACTGAACGCGAACTTTGAACAGTGGAAAGGCATCAAAAACGACCTGGAGAACAAAATCTCCATTC
TGCAGCGCGACCTGGATGAAAAATACGGCGTGGTGCAGGAGAACAACACGGTGATCGACGGCCTGAAAATCG
AGCTGCAGAAACTGACCGAACAGAAACGTGAATGCGAAAGCTTCAGCAACGCAGAGATTCAGCGTATCAAAGA
AACCGTTGAAAAGCTGGAGTCGGAAAACATCAGCATCCACCAGGGCATCCAGGAGAAGGACAAGGCCTTCGCT
CTCCTGGAATTCCAGAACAAATCCCTGACGCAGGGTAACAAACAGTCCATCATCCACATCGACGAGATGAAGGC
GCTGAACACCTGCCTTGAAAACAAGGTTAAAGAACTGCAGAAAAACTTCGAGCTGAGCAGCACCCGCCTGGAT
GAAGCCAACATCAAGATCGCGGAGAACGAGAAGGAGATGAACCTGGTTAACACCCAGCTGATCACCGTTACCG
ACGAGAACCAGGAGTGGCAGCACCGTTTTGACGAACTGACCAACCAGAACCACAGCTTCGCTAAGGAGATCGA
GATCCTGAAAAGCAGCCTGGACGGCGAAAACTCCAAGAACAACATGGACTTCAAACTGCTCGAAGGCAAAAAC
CGCGAACTGGAGAGCTTCCTGGAAAAGGCGCAGCTGCGCATCGAAGATCAGGGTAGCAACATCCACAACCTGC
AGCTGAAACTGAAGAGCAAAAACGAGAAATTCATCAACCTGGAAAACAACATTATCTTCTCCAACGAACAGAAGC
TGCAGCTGCTGTCCGACGTGGAATCCTACAAAAACACCTCTCGCAGCAAAGAGGATGATATCAAAGAACTGCAG
CAGCTCGTGGACTCCCTGAACAACGAGAAGCGCGACCTGACTACCCGGTGCGACGCGTACAGCACTAAGAAAC
TGCAGATGGAGAGCGACTTCAACGAATGCAAGAATGAACTGCGCATCTGCGAACTGAACACCAAAGAGCTGCA
GAGCTGCGTGAAGTCCTATGAGATCGAGCTGGAGAACGTCAAATTCCAGCTGGGCGAATGCTCCCGTCTGCAG
TCTATCCTGGATGAAGAACGTAAAAAATTCGAAGTTGAAAAAATCAAATACCAGGAAGATATCCTCACTCACTCT
CGCAGCAACAACGAAGAAATCGCACAGTTCAAGATCAAATGCGATAAACTGGAAAGCGAGATGTCCAAACTGAA
ACATGACGACTCTGAATTTGTGGAACTCAAATCCGCAAATAGCGAACTGCTGTCCAAAATCACCTGTCTCAGCA
GCCAGATTACTCTGCTGCTGAGCGAAAAAGAAAAGATCGATGAAGATCTGGTGCGCTTGACCGATAGCAACGAA
GCCGTCCTGCAGACGAAACAACACGAAATCATCGAACTGAAAGAAAAAATCAACTCTATCCTGAAAGACCATAA
AAAAGAAATTGAAGATACCCACAACGAATATAAAGAAAAAATGGAAAGCAGCCTGTACGACGGTGATTCCGTTAA
AGAAGAGATCGCCTCCCTGCAGAACCTGGTTAAATCTAAGGAAAACGACGCAAACCTGCTGAACGAGCAGGTT
AACCACAAGAAGAAGCGATTACCTGCCTGGAAAACCGTCTGTCCCAGGAAGCAGTTGCGCTGAGCGAAGTGC
TGAACAACAACAAAAAACTGGTTATCGAAATCGAAGAACTGAAAAAACTGAATTGCCAGCTGGAAAACAACATTC
TTGAGGTTTCTGAATCCCAGTCTAAAAAAGAATTCGACAACTTGCGCCAGACTCTGAAAAGCTGCAAACTGGAA
CTGGCTTCCACTCAGGTAGAGTCTACTTTCAAAGATAAAGAAATTGATACCCTGCGTAAAGATATTAACTTCCTG
TCTAAAAAATCTAACACCTACAAAGAAGAACTGCGTAAAGTTCGTAACGAAAACATGGACACCACCATCTATAAC
AACGAATCTAAACTGAAAAAACGTAATGAGACTAAAGTTGAACGTCAGAACGACGCGATGCATAGCGTG (SEQ ID NO. 32)

FIGURE 18A

MSTEDKEGLESIRMLHSHLDDDKDGSIEPAETGEFIRGGELRGEDYIKRQKLFHRSDVEITVLDLWQTWTTSTV
HNWTVDQTIEWLLTSVDLPQYKTTFEYHSVNGSRIPQIAVNSSYLTKVLKITNPIHKSKLSLKAMDVVLFGPPKE
PSSFFKDVIFTIIILLAGTGLFYAYHKNKKSQDQLKKMMEDMDKLGVAERDLLDLQSKLQQKDKVIKNIRSVSKEL
NQVSLETEEIKRMREEIEDLRNQLYAAETELEDKCWSAPPTLQLWLQISYEIESMGFSAKKKEAEKQLELAKDM
CEKLKKKRS (SEQ ID NO. 33)

FIGURE 18B

ATGAGCACTGAAGATAAAGAAGGCCTGGAGAGCATCCGTATGCTGCACAGCCACCTGGATGATGATAAAG
ATGGTAGCATCGAACCGGCGGAAACCGGTGAATTCATCCGTGGTGGCGAACTGCGTGGCGAAGACTACA
TCAAACGCCAGAAACTGTTCCACCGTAGCGATGTTGAAATCACCGTGCTGGATCTGTGGCAGACCTGGAC
CACCAGCACCGTGCACAACTGGACCGTGGATCAGACCATCGAGTGGCTGCTGACCAGCGTGGACCTGCC
GCAGTACAAAACCACCTTCGAATACCACTCTGTTAACGGCAGCCGCATCCCGCAGATCGCGGTTAACAGC
AGCTACCTGACCAAAGTTCTGAAAATTACCAACCCGATCCACAAAAGCAAACTGAGCCTGAAAGCGATGG
ACGTTGTGCTGTTCGGTCCGCCGAAAGAACCGAGCTCTTTCTTCAAAGATGTTATCTTCACCATCATCATC
CTGCTGGCCGGCACCGGTCTGTTCTACGCTTACCACAAAAACAAAAAATCCCAGGACCAGCTGAAAAAGA
TGATGGAAGATATGGATAAACTGGGCGTTGCGGAACGTGACCTGCTGGATCTGCAGTCTAAACTGCAACA
GAAAGACAAAGTCATCAAAAACATTCGTAGCGTTAGCAAAGAACTGAACCAGGTTTCTCTGGAAACCGAA
GAAATCAAACGTATGCGTGAAGAAATCGAAGATCTGCGTAACCAGCTGTACGCGGCGGAAACCGAACTG
GAAGACAAATGCTGGTCCGCCCCACCGACCTTGCAGCTGTGGCTGCAGATTTCATACGAAATCGAATCCA
TGGGCTTTTCAGCGAAAAAGAAAGAAGCTGAGAAACAGCTGGAACTCGCTAAAGATATGTGCGAGAAACT
CAAAAAGAAACGCTCT (SEQ ID NO. 34)

FIGURES 18A AND 18B

1: CELL LYSATE WITH INDUCTION, 16 HOURS AT 15°C
2: CELL LYSATE WITH INDUCTION, 4 HOURS AT 37°C
3: SUPERNATANT OF CELL LYSATE WITH INDUCTION, 16 HOURS AT 15°C
4: PELLET OF CELL LYSATE WITH INDUCTION, 16 HOURS AT 15°C
5: SUPERNATANT OF CELL LYSATE WITH INDUCTION, 4 HOURS AT 37°C
6: PELLET OF CELL LYSATE WITH INDUCTION, 4 HOURS AT 37°C

SEQUENCE LISTING

<160> NUMBER OF SEQ ID NOS: 34

<210> SEQ ID NO 1
<211> LENGTH: 228
<212> TYPE: PRT
<213> ORGANISM: Lepeophtheirus salmonis

<400> SEQUENCE: 1

```
Met Arg Glu Glu Val Pro Gln Arg Ala Ile Lys Ala Asp Lys Leu Gly
1               5                   10                  15

Phe Leu Ala Arg Asp Ala Asn Met Val Lys Met Ala Lys Ala Leu Glu
            20                  25                  30

Lys Gly Arg Ser Val Ser Arg Asp Ile Gly Gly Ser Asp Pro Glu Arg
        35                  40                  45

Met Ala Pro Pro Arg Val Glu Glu Tyr Val Arg Ser Val Phe Lys Asp
    50                  55                  60

Ser Gly Val Lys Ile Glu Val Val Ala Gly His Asp Thr Phe Glu Lys
65                  70                  75                  80

Glu Tyr Pro Cys Leu Ala Ala Val Asn Arg Ala Ala Ser Thr Val Ala
                85                  90                  95

Arg His Gln Gly Arg Val Ile Trp Leu Thr Tyr Glu Pro Glu Gly Lys
            100                 105                 110

Val Glu Lys Thr Ala Met Ile Val Gly Lys Gly Ile Thr Tyr Asp Thr
        115                 120                 125

Gly Gly Ala Asp Ile Lys Ala Gly Gly Ile Met Ala Gly Met Ser Arg
    130                 135                 140

Asp Lys Cys Gly Ala Ala Asp Ala Ala Gly Phe Met Lys Thr Ile Ser
145                 150                 155                 160

Glu Leu Lys Pro Lys Asn Leu Lys Val Val Gly Met Ala Met Val
                165                 170                 175

Arg Asn Ser Val Gly Ser Asn Cys Tyr Val Ser Asp Glu Ile Ile Thr
            180                 185                 190
```

Ser Arg Ala Gly Val Arg Ile Arg Val Gly Asn Thr Asp Ala Glu Gly
            195                 200                 205

Arg Met Ala Met Val Asp Val Leu Cys His Met Arg Glu Lys Ala Leu
210                 215                 220

Arg Glu Val Asn
225

<210> SEQ ID NO 2
<211> LENGTH: 684
<212> TYPE: DNA
<213> ORGANISM: Lepeophtheirus salmonis

<400> SEQUENCE: 2

```
atgagggaag aggtgccaca aagggcgatc aaggcagata agttgggatt tttggccagg      60
gacgctaata tggtgaagat ggctaaggca ttggagaaag ggagatccgt atctagagac     120
attggaggct ctgatcctga agaatggcac ccacctcgtg tggaggaata cgttcgttca     180
gtctttaagg actctggtgt taaaattgag gttgttgcag acacgacac ctttgaaaag     240 gagtatccgt gccttgctgc tgtgaatcgt gcagcatcca ctgtagctcg tcatcaagga     300
cgtgttattt ggttgacata tgagcctgaa ggaaaggtag aaaagacagc catgattgta     360
ggaaagggta tcacttatga taccggtgga gctgatatca aggctggcgg aatcatggct     420
ggaatgtcca gggacaaatg tggagccgca gatgctgctg gattcatgaa aaccatttca     480
gaattgaagc caaagaactt gaaggtcgtt gttggaatgg ctatggtgcg aatagtgtt     540 ggatccaatt gctatgtgtc tgatgaaata attacctctc gtgctggagt aaggattcgt     600
gtgggtaaca cggatgctga gggtcgaatg gccatggtag atgttctctg ccacatgaga     660
gaaaaggctt taagagaagt taat                                           684
```

<210> SEQ ID NO 3
<211> LENGTH: 191
<212> TYPE: PRT
<213> ORGANISM: Lepeophtheirus salmonis

<400> SEQUENCE: 3

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Pro Asn Thr Ile
        115                 120                 125

Lys Glu Leu Gly Lys Met Lys Gln Glu Pro Val Lys Pro Glu Asp Gly
    130                 135                 140

Arg Thr Met Ala Glu Lys Ile Asn Ala Phe Ala Tyr Leu Glu Cys Ser
145                 150                 155                 160

```
Ala Lys Ser Lys Glu Gly Val Arg Glu Val Phe Glu Thr Ala Thr Arg
                165                 170                 175

Ala Ala Leu Gln Val Lys Lys Lys Lys Arg Pro Cys Val Leu
        180                 185                 190

<210> SEQ ID NO 4
<211> LENGTH: 573
<212> TYPE: DNA
<213> ORGANISM: Lepeophtheirus salmonis

<400> SEQUENCE: 4
atggctgcta ttcgaaagaa gttggtcatt gttggggatg gagcctgcgg taagacttgt      60
ctcctcatcg tcttcagtaa agatcagttc ccagaagtct acgtcccaac cgtgtttgaa     120
aactatgtgg ccgacatcga agtggatgga aagcaggtgg aactggcgct ctgggatact     180
gcaggccaag aagactatga tcgccttcgt cctttatcgt atccggacac ggatgttatt     240
ctcatgtgtt tctctattga ctctccggac tcccttgaga acattccaga gaaatggacg     300
ccggaagtca acatttttg ccccaatgta cctataatac tcgtggggaa caaaaaggat     360
cttagaaatg acccaaacac gataaaagaa ttggggaaaa tgaagcaaga gccagtcaaa     420
cccgaagacg tcgcacaat ggcggaaaaa atcaacgcat ttgcttattt ggaatgttcc     480
gctaaatcta aggaaggggt cagagaggtc ttcgaaactg ctacccgagc cgcgttgcaa     540
gtgaagaaaa agaagaagag accttgcgtt cta                                  573

<210> SEQ ID NO 5
<211> LENGTH: 58
<212> TYPE: PRT
<213> ORGANISM: Lepeophtheirus salmonis

<400> SEQUENCE: 5

Met Ala Asp Arg Asn Thr Glu Phe Glu Leu Glu Glu Leu Leu Gln Phe
1               5                   10                  15

Lys Lys Ser His Glu His Glu Phe Ser Ser Ala Thr Arg Thr Ala Glu
            20                  25                  30

Gln Ala Ile Glu Ile Thr Lys Asn Asn Ile Ala Trp Met Asp Ser Ser
        35                  40                  45

Tyr Lys Thr Ile Gln Glu Trp Leu Asn Lys
    50                  55

<210> SEQ ID NO 6
<211> LENGTH: 174
<212> TYPE: DNA
<213> ORGANISM: Lepeophtheirus salmonis

<400> SEQUENCE: 6
atggctgaca ggaatacgga gtttgaactt gaagagctac ttcaatttaa aaaatctcac      60
gaacatgagt ttagttcagc aactcgtacc gcagagcaag ctattgaaat aacgaagaat     120
aatatcgcct ggatggactc cagctataaa accattcaag agtggttgaa taaa           174

<210> SEQ ID NO 7
<211> LENGTH: 67
<212> TYPE: PRT
<213> ORGANISM: Lepeophtheirus salmonis

<400> SEQUENCE: 7

Met Met Ser Met Asn Gly Arg Leu Ala Phe Ala Ile Ala Ala Gly Ala
1               5                   10                  15
```

```
Phe Gly Ser Ser Phe Gln His Gly Tyr Asn Thr Gly Val Leu Asn Ala
             20                  25                  30

Pro Gln Val Leu Ile Thr Asn Trp Leu Arg Gly Cys Glu Lys Asn Met
         35                  40                  45

Thr Ala Val Thr Glu Asp Gly Ser Asp Val Leu Val Cys Glu Lys Asp
     50                  55                  60

Met Lys Ser
65

<210> SEQ ID NO 8
<211> LENGTH: 201
<212> TYPE: DNA
<213> ORGANISM: Lepeophtheirus salmonis

<400> SEQUENCE: 8
atgatgtcca tgaatggaag attggctttt gctatagcag ccggtgcatt tggatcttct      60
tttcaacatg gatataatac cggagttttg aatgctcctc aagttcttat tacgaattgg    120
ttgagaggat gtgagaaaaa tatgacagca gttacagagg atggaagtga cgttcttgtc    180
tgtgagaaag atatgaaaag c                                               201

<210> SEQ ID NO 9
<211> LENGTH: 72
<212> TYPE: PRT
<213> ORGANISM: Lepeophtheirus salmonis

<400> SEQUENCE: 9

Met Tyr Ile Cys Asp Ser Glu Gly Asn Val Ile Cys Val Asp Gly Trp
1               5                  10                  15

Ser Tyr Pro Ser Lys Leu Cys Ser Glu Pro Ile Cys Asp Met Asn Gly
             20                  25                  30

Arg Gly Cys Val Asn Gly Lys Cys Ile His Pro Asn Val Cys Ala Cys
         35                  40                  45

Glu Val Gly Trp Asp Gly Pro Asn Cys Asp Glu Cys Ile Pro Leu Gly
     50                  55                  60

Gly Cys Lys His Gly Ser Cys Asn
65                  70

<210> SEQ ID NO 10
<211> LENGTH: 216
<212> TYPE: DNA
<213> ORGANISM: Lepeophtheirus salmonis

<400> SEQUENCE: 10
atgtacattt gcgattcgga aggaaatgtc atctgtgttg atggatggtc ttatccatct      60
aaactctgta gtgaacctat ctgtgatatg aatggaagag atgcgttaa tggaaaatgc    120 atccatccaa atgtatgcgc atgtgaagtt ggatgggatg gccctaactg tgatgaatgt    180
attcctcttg gtggttgtaa gcatggaagc tgtaac                               216

<210> SEQ ID NO 11
<211> LENGTH: 272
<212> TYPE: PRT
<213> ORGANISM: Lepeophtheirus salmonis

<400> SEQUENCE: 11

Met Asn Glu His Val Cys Ser Leu Phe Ile Tyr Thr Asp Pro Phe Leu
1               5                  10                  15

Trp Arg His Ile Tyr Arg Ser Met Lys Gly Ser Lys Arg Ala Glu Arg
```

```
        20                  25                  30
Thr Arg Leu Lys Ile Glu Lys Leu Leu Thr Glu Ser Val Thr Arg Val
            35                  40                  45

Asn Glu Ala Phe Ser Met Ala Glu Phe Tyr Gly Ser Gly Gln Thr Ile
         50                  55                  60

His Lys Gly Val His Phe Ser Leu Leu Asp Tyr Ile Ile Asp Asp Asp
 65                  70                  75                  80

Thr Arg Cys Phe Ser Asp Thr Glu Tyr Cys Asp Glu Lys Val Met Pro
                 85                  90                  95

Met Gly Glu Met Cys Asn Glu Pro Ile Val Cys Asp Asn Leu Lys His
            100                 105                 110

Val Phe Cys Asn Asn Leu Thr Ser Leu Arg Phe Tyr Leu His Ala Phe
            115                 120                 125

Ser Ala Phe Arg Asn His Gly Ala Phe Cys Leu Ser Tyr Ala Phe Thr
         130                 135                 140

Tyr Arg Asn Met Ser Asp Phe Gln Gly Ile Ala Trp Val Lys Gly Tyr
145                 150                 155                 160

Asp Gln Ser Asp Glu Arg Ser Leu Ser His Tyr Gly Tyr Cys Ser Leu
                165                 170                 175

Asn Asp Glu Lys Cys Gln Asp Glu Ser Leu Gln Tyr Tyr Phe Arg Asn
            180                 185                 190

Thr Gly Val Val Asn Phe His Arg Leu Gly Glu Asn Phe Ser Thr Ser
         195                 200                 205

Ile Gly Ala Asn Val Phe Ile His Glu Ile Gly His Ser Leu Gly Ser
    210                 215                 220

Thr His Asp Asp Lys Val Ser Glu Cys Asn Pro Gln Gly His Asp Leu
225                 230                 235                 240

Tyr Leu Met Thr Gly Lys Ala Glu Asn Ile Leu Leu Gln Arg Asn Ser
                245                 250                 255

Asp Arg Leu Ser Ala Cys Ser Ser Arg Glu Ile Gly Arg Asn Leu Asp
            260                 265                 270

<210> SEQ ID NO 12
<211> LENGTH: 816
<212> TYPE: DNA
<213> ORGANISM: Lepeophtheirus salmonis

<400> SEQUENCE: 12
atgaatgaac atgtctgcag tttgttcatc tacacagatc catttctctg gagacacatt     60
tatcgctcta tgaaaggaag taaaagagca gaaaggacga ggctcaaaat tgaaaaatta    120
ctcacagaat ccgtaacaag agtaaatgag gcattctcta tggctgagtt ttatgggtct    180
ggtcagacca tacataaggg agttcacttt tccttactgg attatatcat cgacgacgac    240
acaagatgct tctcagacac ggaatattgt gatgaaaaag tcatgcccat gggagaaatg    300
tgcaatgagc ccatcgtatg tgacaacttg aagcatgtct tttgtaacaa cttaacaagt    360
ctacgtttct atctccatgc ttttttccgca tttcgcaacc atggagcatt tgtctttca    420 tatgcgttta catataggaa catgagtgat tttcaaggga ttgcatgggt aaagggatat    480
gatcaaagcg atgagcgctc tttgagtcac tatggatatt gctcattgaa tgatgaaaag    540
tgtcaggatg agagtctcca atattatttc aggaacacgg gtgtagtcaa ttttcataga    600
ttaggagaaa attttttcaac gtcaattgga gcaaatgtat ttatacatga aattggtcat    660
agtttaggaa gcacacacga cgataaagtg agtgagtgca atccgcaggg ccatgacttg    720
```

```
tatcttatga cgggaaaggc tgagaacata ttacttcagc gaaacagcga tcggctttct      780
gcatgctcaa gtcgggaaat tggaaggaac ttggat                                816
```

<210> SEQ ID NO 13
<211> LENGTH: 114
<212> TYPE: PRT
<213> ORGANISM: Lepeophtheirus salmonis

<400> SEQUENCE: 13

```
Met Glu Asn Ser Arg Ala Asp Val Pro Asn Ile Glu Asp Lys Ile Pro
1               5                   10                  15

Pro Lys Ile Glu Glu Asp Asn Glu Leu Gln Gly Asn Ser Leu Thr Val
            20                  25                  30

Pro Lys Ser Ser Asn Arg Glu Ser Ser Asn Val Arg Arg Met His Thr
        35                  40                  45

Ala Val Arg Leu Asn Glu Val Ile Val Asn Lys Ser His Asp Ala Lys
    50                  55                  60

Leu Val Ile Leu Asn Leu Pro Ser Pro Lys Ile Met Gly Pro Asp
65                  70                  75                  80

Lys Asp Ala Ser Tyr Met Glu Phe Leu Glu Val Leu Thr Glu Gly Leu
                85                  90                  95

Glu Arg Val Leu Met Val Arg Gly Gly Gly Arg Glu Val Ile Thr Ile
            100                 105                 110

Tyr Ser
```

<210> SEQ ID NO 14
<211> LENGTH: 342
<212> TYPE: DNA
<213> ORGANISM: Lepeophtheirus salmonis

<400> SEQUENCE: 14

```
atggagaata gtcgagctga tgttccaaac attgaagaca aataccacc caagattgaa       60 gaagataatg agttacaagg caactctctc acagtaccaa agtcttcaaa tcgtgagtct     120
tctaacgtca gacggatgca tactgccgta cgattgaacg aagtgattgt caacaagtcc     180
cacgatgcaa aattagtaat tttgaatctt ccaagtcctc ccaaaattat gggtccagac     240
aaagatgcta gctatatgga attttttagaa gttttaaccg agggtttaga gcgagtcctt     300
atggttcgag gaggcggacg agaagtgatt accatttact ct                        342
```

<210> SEQ ID NO 15
<211> LENGTH: 448
<212> TYPE: PRT
<213> ORGANISM: Lepeophtheirus salmonis

<400> SEQUENCE: 15

```
Met Glu Phe Leu Gly Gly Phe Thr Ile Asn Leu Ala Phe Ile Thr Asn
1               5                   10                  15

Gly Phe Ala Leu Ala Tyr Pro Thr Ile Ala Leu Ser Gln Leu Thr Asn
            20                  25                  30

Asn Gly Thr Glu Ser Cys Ser Phe Val Met Ser Lys Glu Glu Gly Ser
        35                  40                  45

Trp Phe Ala Gly Leu Leu Gly Ile Gly Ile Cys Gly Ser Val Phe
    50                  55                  60

Phe Gly Thr Leu Ile Gly Gln Arg Ile Gly Asn Arg Lys Thr Leu Leu
65                  70                  75                  80

Leu Ala Ala Ile Leu Asp Ile Ile Gly Trp Leu Leu Ile Ala Phe Ala
```

```
            85                  90                  95
Val Asn Ser Pro Met Met Gly Gly Arg Phe Leu Asn Gly Val Phe
            100                 105                 110

Val Gly Thr Ile Gly Pro Ser Gly Tyr Thr Phe Leu Ser Glu Ile Met
            115                 120                 125

His Arg Lys His Arg Ala Ser Cys Ser Gln Ala Thr Ser Val Ala Ile
            130                 135                 140

Ser Ala Gly Met Leu Val Thr Tyr Gly Leu Gly Ser Val Ile Ser Trp
145                 150                 155                 160

Asn Leu Leu Ala Ile Gly Cys Gly Ile Ser Ser Val Leu Phe Phe Ile
                    165                 170                 175

Met Leu Leu Thr Met Pro Asp Ser Pro Tyr Trp Asn Ala Ser Ile Gly
                    180                 185                 190

Lys Ile Glu Glu Ala Lys Lys Ser Leu Ser His Phe Arg Ser Lys Lys
                    195                 200                 205

Asp Asp Val Glu Glu Glu Phe Lys Glu Ile Met Glu Gly Ile Gln Lys
                    210                 215                 220

Ser Ile Lys Lys Glu Lys Ile Ser Phe Phe Glu Ala Met Lys Leu Leu
225                 230                 235                 240

Phe Thr Asp Glu Thr Cys Tyr Lys Pro Phe Ile Ile Leu Ser Val Leu
                    245                 250                 255

Phe Leu Ile Gln Thr Leu Ser Gly Leu Tyr Ala Val Ile Ala Tyr Ala
                    260                 265                 270

Ile Gln Val Leu Glu Glu Ser Arg Thr Pro Ile Asp Thr Asn Leu Gly
                    275                 280                 285

Thr Ile Ile Ser Gly Ala Met Arg Leu Phe Phe Gly Thr Leu Ala Ile
                    290                 295                 300

Pro Leu Phe Phe Tyr Leu Pro Arg Lys Thr Leu Met Tyr Ile Ser Thr
305                 310                 315                 320

Gly Leu Ala Cys Leu Ser Ile Ser Ser Leu Gly Ile Leu Gly Leu Leu
                    325                 330                 335

Glu Leu Glu Thr Asn Thr Phe Thr Thr Tyr Phe Pro Val Gly Ala Ile
                    340                 345                 350

Ser Leu Tyr Met Val Ser Phe Thr Phe Gly Phe Gln Ser Ile Pro Phe
                    355                 360                 365

Leu Tyr Leu Gly Glu Tyr Tyr Pro Pro His Val Arg Gln His Leu Ala
                    370                 375                 380

Gly Leu Thr Ser Thr Leu Arg Phe Leu Gly Phe Phe Ile Met Leu Lys
385                 390                 395                 400

Leu Phe Pro Gln Met Met Glu Phe Gly Pro Asn Tyr Thr Phe Ile
                    405                 410                 415

Phe Leu Gly Leu Val Cys Leu Phe Ala Gly Ile Tyr Ala Lys Val Val
                    420                 425                 430

Leu Pro Glu Thr Lys Gly Leu Thr Leu Asn Gln Ile Gln Asp Leu Phe
                    435                 440                 445

<210> SEQ ID NO 16
<211> LENGTH: 1344
<212> TYPE: DNA
<213> ORGANISM: Lepeophtheirus salmonis

<400> SEQUENCE: 16
atggagtttt taggtggatt tacgattaat cttgcattta ttactaatgg atttgccttg      60
gcctatccca caattgcatt gagtcaactc accaataatg gtactgaatc atgctcattt     120
```

-continued

```
gttatgagca aggaagaggg atcctggttc gctggacttt tgggcatcgg aggtatttgt      180
gggagtgtgt tcttcggaac tttgattggc caaagaattg gtaatcgaaa gactctcctc      240
ttggcagcta ttttagacat tattggatgg cttcttattg catttgctgt gaattctcca      300
atgatgatgg gaggacgatt tttaaatggt gttttttgttg gcacaatagg ccctagtgga     360
tacaccttcc tatcagaaat aatgcatcgt aaacatcgag cttcttgttc acaagcaact      420
tctgttgcaa ttagtgctgg gatgctagtc acttatggac tagggtctgt gatttcatgg      480
aacctccttg cgattggatg tggtatttct tcagttctgt tctttatcat gttacttaca      540
atgccagact ctccatattg gaatgcctct atcggaaaaa ttgaggaagc caagaaatct      600
ttaagtcatt tcaggtcaaa gaaggacgat gtggaagaag agttcaaaga aatcatggaa      660
ggaatacaaa atccatcaa aaaagaaaag atttcattct tcgaggctat gaagttactc       720
ttcacggatg agacatgcta caaaccttc ataatattaa gcgttttgtt cttaattcaa       780
accctttctg ggttgtatgc agttattgct tatgctattc aagtattgga gagtccagg       840 actcctattg atacaaattt gggcacaatt atctccggag caatgcgact ttttttttgga    900 actcttgcaa ttcccctctt cttttatcta cctcgtaaaa cactaatgta catttccact      960
ggccttgctt gtctctctat ttcctctctg gcattttgg gtctcctaga attggaaaca      1020
aatacattta ccacatattt ccccgttggt gcaatttctt tatatatggt gtcatttaca     1080
tttggattcc agagcattcc tttcctctat cttggagagt attatccacc tcatgtgaga    1140
cagcacttgg caggcttaac ctccacctta agattcttag ggttttttat catgctcaaa     1200
ttatttcctc aaatgatgga gttctttgga ccaaattata catttatatt cctaggactt    1260
gtatgtctct tgctggaat ttacgccaaa gtagttctcc ctgagacaaa ggggcttact     1320
ctgaatcaaa ttcaagacct attc                                            1344
```

<210> SEQ ID NO 17
<211> LENGTH: 542
<212> TYPE: PRT
<213> ORGANISM: Lepeophtheirus salmonis

<400> SEQUENCE: 17

```
Met Tyr Ser Gly Val Gln Ala Leu Thr His Leu Leu Glu Glu Val Arg
1               5                   10                  15

Val Pro Tyr Lys Val Trp Ile Leu Gly Glu Asp Ser Leu Asp Thr Leu
                20                  25                  30

Pro Trp Lys Glu Phe Ala Leu Leu Leu Phe Gln Asp Phe Lys Thr Phe
            35                  40                  45

Val Ser Ile Asn Leu Phe Thr Arg Lys Leu Ile Phe Lys Tyr Cys Ser
        50                  55                  60

Glu Tyr Ser Val Gly Ile Ile Val Ser Ala Thr His Gln Thr Pro Leu
65                  70                  75                  80

Pro Leu Lys Ile Thr Asn Asp Ser Ile Phe Gln Arg His Asn Ser Leu
                85                  90                  95

Arg Asn Leu Phe Ile Cys Pro His Ser Gln Ile Pro Asn Ile Leu Lys
            100                 105                 110

Ala Ser Arg Thr Leu Tyr Glu Thr Leu Asp Ser Tyr Gly Phe Leu Ser
        115                 120                 125

Phe Thr Ser Arg Phe Leu Thr Lys Ser Thr Thr Pro Val Leu Glu Ala
    130                 135                 140

Met Ser Asp Ser Gly Pro Val Thr Ile Val Leu His Asp Arg Gly Gln
```

```
            145                 150                 155                 160
Val Pro Lys Ile Ile Phe Ala Ser Asn Pro Leu Ser His Trp Leu Leu
                165                 170                 175
Lys Leu Leu Phe Leu Asp Ser Ile Thr Phe Leu Ser His Gln Leu Ile
            180                 185                 190
Asn Leu Asp Thr Lys Arg Trp Val Leu Ile Asp Val Asp Ile Phe
        195                 200                 205
Val Gly Lys Asn Arg Leu Ser Pro Ser Asp Val Arg Glu Leu Val Ile
    210                 215                 220
Ser Gln Asp Lys Leu Arg Lys Asn Ile Tyr Gly Phe Lys Tyr Asn Leu
225                 230                 235                 240
Gly Phe Ser Gly Tyr Tyr Phe Arg Asn Gln Gly Ser Ser Leu Ile Asn
                245                 250                 255
Lys Glu Gly Asp Ala Ala Leu Ile Glu Lys Lys His His Phe Trp Trp
            260                 265                 270
Phe Pro His Thr Phe Arg His Leu Gln Pro His Met Phe Asn Ser Ser
        275                 280                 285
Leu Gln Leu Glu Gln Gln Met Phe Leu Asn Lys Lys Phe Ala Leu Glu
    290                 295                 300
Tyr Lys Leu Pro Val Asn Phe His Tyr Ala Val Ala Pro His His Ser
305                 310                 315                 320
Gly Val Tyr Pro Val His Lys Pro Leu Tyr Asp Ala Trp Lys Asn Val
                325                 330                 335
Trp Gly Ile Val Val Thr Ser Thr Glu Glu Tyr Pro His Leu Lys Pro
            340                 345                 350
Ser Arg Leu Arg Arg Gly Phe Thr His Asp Lys Leu Lys Ile Leu Pro
        355                 360                 365
Arg Gln Thr Cys Gly Leu Phe Thr Lys Asn Ile Tyr Tyr Glu Asp Tyr
    370                 375                 380
Pro Lys Asn Pro Glu Val Leu Glu Lys Ser Ile Arg Gly Gly Glu Leu
385                 390                 395                 400
Phe Gln Thr Ile Ser Phe Asn Ser Ile Asn Ile Phe Met Thr His Met
                405                 410                 415
Ser Asn Tyr Gly Phe Asp Arg Leu Ala Pro Tyr Thr Phe Glu Ser Val
            420                 425                 430
Phe Ser Met Leu Lys Cys Trp Thr Asn Leu Lys Phe Val Thr Val Asn
        435                 440                 445
Pro Glu Lys Leu Ser Glu Ile Tyr Phe Asn Met Phe Pro Asp Glu Lys
    450                 455                 460
Val Pro Ile Trp Gly Asn Pro Cys Tyr Asp Ser Arg Leu Lys Glu Ile
465                 470                 475                 480
Trp Ser Lys Asn Lys Asn Cys Lys Arg Leu Pro Asn Phe Leu Val Ile
                485                 490                 495
Gly Pro Gln Lys Thr Gly Thr Thr Ala Leu Tyr Asn Phe Leu Lys Ile
            500                 505                 510
His Pro Ser Ile Ile Ser Asn Asn His His Ser Lys Tyr Phe Glu Glu
        515                 520                 525
Val Gln Phe Phe Ser Ser Ser Asp Tyr Leu Lys Gly Phe Glu
    530                 535                 540

<210> SEQ ID NO 18
<211> LENGTH: 1626
<212> TYPE: DNA
<213> ORGANISM: Lepeophtheirus salmonis
```

<400> SEQUENCE: 18

```
atgtactctg gtgtccaagc attgactcac ctcttggaag aagtccgtgt ccctacaaa      60
gtgtggattt tgggagagga ctccttggac accctacctt ggaaggaatt cgcccttctt    120
ctcttccagg attttaaaac cttcgttcct atcaacttgt tcactcgaaa attgatattt    180
aaatattgtt cagaatattc tgtcggtatc attgtatccg ccacccatca acgcctctt     240
cctttaaaaa ttaccaatga ttccattttt caacgtcata attcacttag aaatttattt    300
atttgtcctc atagtcaaat tcctaatatt ctaaaagcgt tcgtactct ctatgaaact     360
cttgactctt acgggttctt atcatttact tctcgttttc tcactaaatc tactacccct    420
gtccttgagg cgatgtctga ttccgggcct gttactatag ttcttcatga tagaggacaa    480
gtaccaaaga ttatctttgc ttcaaatcct ttgagtcact ggcttttaaa gctacttttc    540
ctagactcta ttactttttt gagtcatcaa cttattaact tagacactaa aaggtgggtt    600
ctcatagatg ttgacgatat tttcgtcggc aaaaaccggc tttctccatc tgatgttaga    660
gagcttgtta tctctcaaga taaacttcgt aagaatattt atggatttaa atataacctg    720
ggattttctg ctattatttt ccgtaaccaa ggttcatctt taataaataa agaaggtgat    780
gccgccctca ttgaaaaaaa acaccatttt tggtggttcc cccatacatt cagacattta    840
caacctcata tgttcaattc ctcacttcaa cttgaacagc agatgtttct taataagaaa    900
tttgcgctgg aatacaaatt gccggtcaat ttccattatg ccgttgctcc ccatcattct    960
ggtgtttacc ctgttcataa gccattatat gatgcttgga aaatgtctg ggggatagtt    1020
gttacttcca cagaggaata tcctcacctt aaaccatctc gattacgtcg tggatttaca    1080
catgataaat taaaaattct tccgaggcaa acatgtggtc tctttactaa aaacattat    1140
tatgaagatt accctaaaaa tcctgaagtg ttggaaaaat ctatcagagg tggagaactg    1200
tttcagacta tttcatttaa ttctataaat atattcatga cacatatgtc caattatgga    1260
tttgatagac tggctccgta cttttgaa tctgtatttt ccatgttaaa atgctggact    1320
aacctaaaat ttgttacagt taatccggaa aagctaagtg aaatttattt taatatgttt    1380
cctgacgaga agttccaat tggggaaat ccttgttatg acagtcgcct taagaaatc     1440
tggtcgaaaa ataaaaattg taagaggcta cctaattttc ttgtgattgg accgcaaaaa    1500
actgaacaa cggctttata taatttccta aaaattcatc cttcaataat ttctaacaat    1560
catcactcca aatatttga agaagtacaa ttttcagta gtagcgatta tcttaaaggt    1620
ttcgag                                                              1626
```

<210> SEQ ID NO 19
<211> LENGTH: 282
<212> TYPE: PRT
<213> ORGANISM: Lepeophtheirus salmonis

<400> SEQUENCE: 19

```
Met Glu Phe Tyr Phe Gly Gly Asn Pro Ile Lys Cys Asp Cys Gln Met
1               5                   10                  15

Thr Trp Phe Lys Ser Ile Asn Ser Val Asn Gly Leu Gln Met Phe Pro
            20                  25                  30

Thr Val Ala Asp Leu Glu Ser Ile Tyr Cys Glu Leu Val Tyr Ser Arg
        35                  40                  45

Glu Gln Ser Phe Val Pro Leu Val Glu Ala Glu Ser Asp Asn Phe Leu
    50                  55                  60
```

| | | | | | | | | | | | | | | |
|---|---|---|---|---|---|---|---|---|---|---|---|---|---|---|
| Glu | Tyr | Lys | Ala | His | Cys | Phe | Ala | Leu | Cys | Gln | Cys | Glu | Tyr | Asp |
| 65 | | | | 70 | | | | | 75 | | | | | 80 |
| Ala | Cys | Asp | Cys | Glu | Met | Thr | Cys | Pro | Ser | Asn | Cys | Thr | Cys | Tyr | His |
| | | | 85 | | | | | 90 | | | | | 95 | | |
| Asp | Asn | Ser | Trp | Ala | Lys | Asn | Ile | Ala | Glu | Cys | Ser | Phe | Ser | Asn | Leu |
| | | | 100 | | | | 105 | | | | | 110 | | | |
| Lys | Gly | Leu | Pro | Asp | Arg | Leu | Pro | Met | Asp | Ala | Thr | Glu | Ile | Phe | Leu |
| | | 115 | | | | | 120 | | | | | 125 | | | |
| Asp | Gly | Asn | Glu | Ile | Ser | Val | Val | Gln | Ser | His | Thr | Phe | Ile | Gly | Arg |
| | 130 | | | | | 135 | | | | | 140 | | | | |
| Lys | Asn | Leu | Lys | Ile | Leu | Tyr | Leu | Asn | Glu | Ser | Gln | Val | Arg | Tyr | Leu |
| 145 | | | | | 150 | | | | | 155 | | | | | 160 |
| Pro | Asn | Asn | Ser | Phe | Asn | Gly | Leu | Ile | Ala | Leu | Glu | Glu | Leu | His | Leu |
| | | | | 165 | | | | | 170 | | | | | 175 | |
| Glu | Asn | Asn | His | Ile | Thr | Arg | Leu | Glu | Gly | Ser | Glu | Phe | Asn | Gly | Leu |
| | | | 180 | | | | | 185 | | | | | 190 | | |
| Phe | Arg | Leu | Asn | Lys | Leu | Tyr | Leu | His | Lys | Asn | Lys | Ile | Ser | Phe | Val |
| | | 195 | | | | | 200 | | | | | 205 | | | |
| Asn | Asn | Phe | Thr | Phe | Lys | Glu | Leu | Lys | Ala | Leu | Glu | Thr | Leu | Tyr | Ile |
| | 210 | | | | | 215 | | | | | 220 | | | | |
| His | Gly | Asn | His | Ile | Ser | Ile | Phe | Pro | Pro | Trp | Val | Phe | Gln | Asn |
| 225 | | | | | 230 | | | | | 235 | | | | | 240 |
| Pro | Leu | Leu | Ala | Thr | Leu | Thr | Leu | Ser | Glu | Asn | Pro | Trp | Asn | Cys | Asp |
| | | | | 245 | | | | | 250 | | | | | 255 | |
| Cys | Asn | Tyr | Met | Lys | Arg | Phe | Gly | Asn | Trp | Ile | Glu | Gly | Phe | His | Gly |
| | | | 260 | | | | | 265 | | | | | 270 | | |
| Lys | Ile | Leu | Asp | Leu | Tyr | Tyr | Val | Ser | Cys |
| | | 275 | | | | | 280 | | |

<210> SEQ ID NO 20
<211> LENGTH: 849
<212> TYPE: DNA
<213> ORGANISM: Lepeophtheirus salmonis

<400> SEQUENCE: 20

```
atggaatttt actttggcgg aaaccctatt aaatgtgatt gtcaaatgac atggttcaaa     60
agtattaact cagttaatgg tctacaaatg ttccctactg ttgctgatct tgagtcaatt    120
tattgtgaac ttgtttattc tcgtgaacag agttttgtgc acttgtgga agcagaaagt     180
gacaattttc tctgtgaata caaggcacat tgttttgctc tatgccaatg ttgtgaatat    240
gatgcttgcg attgtgaaat gacttgccct tccaattgca cttgctacca tgacaattct    300
tgggctaaga atattgctga atgctcattt tctaacctga aaggacttcc tgatcgtttg    360
ccaatggatg ctacagaaat attttagat ggaaatgaaa ttagtgtagt gcagagtcat    420
acgtttatcg gtcggaagaa ccttaagata ttatacttga tgaatctca agtaagatat    480
ctgcccaata attcatttaa tggattgata gcactcgaag aactacattt agaaaataat    540
catatcacaa ggctggaagg aagtgaattc aacgggttgt tcgtctaaa taaactttat    600
ttacacaaaa ataagataag ttttgtcaac aactttacat ttaaagagtt aaaagcatta    660
gagactcttt atattcacgg aaatcacatt tccatttcc caccttgggt attttttcaa    720
aatccattgc tggctactct tactctctct gaaaacccat ggaattgtga ctgtaattat    780
atgaaacgat tcgaaaattg gattgaggga tttcatggta aaatcttgga tttgtactat    840
gtatcttgt                                                            849
```

<210> SEQ ID NO 21
<211> LENGTH: 555
<212> TYPE: PRT
<213> ORGANISM: Lepeophtheirus salmonis

<400> SEQUENCE: 21

```
Met Ile Leu Ile Gln Ser Tyr Val Tyr Leu Asp Ala Gln Asn Thr Ala
1               5                   10                  15

Gln His Ile Leu Tyr Met Asp Gln Ala Ser Leu Gly Leu Leu Arg Ile
            20                  25                  30

Asn Phe Val Asp Ser Glu Lys Tyr Lys Glu Ile Ile Lys Ala Tyr Arg
        35                  40                  45

Thr Leu Gln Ser Ser Thr Ala Glu Thr Leu Phe Lys Tyr Leu Asp Ile
    50                  55                  60

Asn Lys Pro Asp Asp Asp Lys Leu Asn Glu Asp Leu Glu Ser Met Phe
65                  70                  75                  80

Gln Phe Glu Lys Ala Ile Ala Gly Ile Met Val Pro Glu Asp Gln Arg
                85                  90                  95

Arg Asn Ser Thr Ala Met Tyr Asn Pro Met Ser Leu Ala Lys Ile Met
            100                 105                 110

Lys Ser Tyr Thr Gln Ile Lys Trp Lys Ile Tyr Phe Asn Glu Leu Leu
        115                 120                 125

Lys Gly Asp Asn Ala Ile Glu Glu Asn Asp Lys Ile Ile Val Ala Glu
    130                 135                 140

Pro Tyr Tyr Phe Glu Lys Leu Asn Glu Leu Leu Asn Glu Thr Asp Asp
145                 150                 155                 160

Lys Ile Ile Tyr Asn Tyr Ile His Trp Arg Ile Leu Leu Gln Thr Leu
                165                 170                 175

Pro Asn Gly Pro Asp Glu Met Arg Glu His Tyr Lys Thr Phe Leu Lys
            180                 185                 190

Asp Ala Met Gly Ile Lys Lys Glu Val Leu Arg Asp Asn Ile Cys Ala
        195                 200                 205

Lys Arg Val Ala Ala Pro Phe Asp Gly Met Gly Gly Leu Gly Phe Ala
    210                 215                 220

Val Ala Tyr Glu Tyr Ile Gln Lys Lys Phe Asp Asp Ser Lys Asn
225                 230                 235                 240

Glu Val Lys Lys Met Val Gly Gly Leu Lys Ser Ser Phe Lys Glu Leu
                245                 250                 255

Val Ala Glu Ser Ser Trp Met Asp Lys Glu Thr Gln Asn Lys Ala Lys
            260                 265                 270

Glu Lys Val Asp Ser Met Val Gln Ser Leu Gly Tyr Pro Asp Trp Leu
        275                 280                 285

Lys Thr Glu Ser Glu Ile Glu Lys Lys Tyr Lys Glu Leu Asp Glu Leu
    290                 295                 300

Lys Pro Lys Thr Leu Leu Glu Asn Ile Lys Lys Val Arg Gln Phe Glu
305                 310                 315                 320

Ser Leu Thr Ser Phe Ser Ala Ile Asn Ser Lys Pro Asp Lys Asn Ala
                325                 330                 335

Trp Pro Leu His Pro Ala Val Val Asn Ala Val Tyr Ser Pro Met Arg
            340                 345                 350

Asn Ser Ile Thr Phe Pro Ala Gly Ile Leu Gln Tyr Pro Phe Phe Glu
        355                 360                 365

Ser Ser Asn Pro Met Tyr Leu Asn Phe Gly Ser Ile Gly Val Val Ile
```

| | 370 | | | | 375 | | | | 380 | | | |
|---|---|---|---|---|---|---|---|---|---|---|---|---|
Gly His Glu Ile Thr His Gly Phe Asp Asp Gln Gly Ser Gln Tyr Asp
385               390             395             400

Asn Asn Gly Asn Leu Val Lys Trp Trp Ser Asn Ser Ser Leu Glu Ala
              405             410             415

Phe Gln Lys Glu Lys Glu Cys Ile Ile Glu Gln Tyr Ser Ala Phe Asn
         420              425             430

Val Pro Glu Ile Ser Glu Thr Tyr Val Asn Gly Val Leu Thr Gln
         435              440             445

Gly Glu Asn Ile Ala Asp Asn Gly Gly Leu Arg Glu Ser Phe Arg Ala
450               455             460

Tyr Lys Lys Trp Val Asn Ser Asn Asn Asp Glu Pro Lys Leu Pro Glu
465               470             475             480

Leu Glu Lys Tyr Thr Ser Glu Gln Met Phe Phe Ile Ala Tyr Ser Gln
         485              490             495

Thr Trp Cys Gln Val Lys Thr Lys Ala Ser Leu Gln Asn Gln Ile Leu
         500              505             510

Ser Asp Pro His Ser Pro Gly Lys Phe Arg Ser Trp Gly Pro Val Ser
         515              520             525

Asn Ser Lys Ser Phe Ser Lys Ala Phe Asn Cys Lys Pro Ser Asp Pro
530               535             540

Met Asn Asn Gly Glu Asn Ser Cys Val Leu Trp
545               550             555

<210> SEQ ID NO 22
<211> LENGTH: 1665
<212> TYPE: DNA
<213> ORGANISM: Lepeophtheirus salmonis

<400> SEQUENCE: 22

```
atgatcctga tccagagcta cgtttacctg gatgcgcaga acacggcgca gcacatcctg      60
tacatggacc aagcgagctt agggctcctg agaattaact ttgtggatag tgagaagtac     120
aaagagataa ttaaggcgta ccgtaccctg cagagctcca ccgcggaaac cctgttcaaa     180
tacttggata ttaataaacc tgacgatgac aaactgaacg aagatctgga atctatgttc     240
cagttcgaaa aagcaatcgc tggcatcatg gtgccggaag atcagcgtcg taactctacc     300
gcgatgtaca cccgatgtc gctggcgaaa atcatgaaat cttacacccca gatcaaatgg     360
aaaatctact caacgaact gctgaaaggc gacaacgcaa tcgaagaaaa cgataaaatc     420
atagtggcag aaccgtacta cttcgaaaaa ctgaacgaac tgctgaacga aaccgacgac     480
aaaattatct ataactatat ccactggcgt atcctgctgc agaccctgcc gaacggcccg     540
gacgaaatgc gtgaacacta caaaaccttc ctgaaagatg cgatgggtat taaaaaagaa     600
gttcttcgtg ataacatctg cgcaaaacgc gttgccgctc cgttcgacgg catgggtggt     660
ctgggcttcg cagttgcgta cgaatacatt cagaaaaaat cgacgacga ctccaaaaac     720
gaagttaaga aaatggttgg tggtctgaaa agcagcttca agaactggt tgcggaaagc     780
tcctggatgg ataaagaaac tcagaacaaa gctaaagaaa agtggattc catggttcag     840
tccctgggtt acccggactg gctgaaaacc gaatctgaaa tcgagaaaaa atataaagaa     900
ctggatgaac tgaaaccgaa aaccctgctg aaaacatta aaaagttcg tcagttcgaa     960
agcctgactt ctttcagcgc gatcaacagc aaaccggata aaacgcatg gccgctgcac    1020
ccggcggtgg ttaacgcggt ttatagcccg atgcgtaact ctattacctt cccggcgggc    1080
```

```
atcctgcagt acccgttctt cgaatctagc aacccgatgt acctgaactt cgggagcatc   1140
ggcgtggtta tcggccacga aatcacccac ggtttcgacg accagggcag ccagtacgat   1200
aacaacggta acctggtgaa atggtggtcc aactccagcc tggaagcctt tcagaaagaa   1260
aaagaatgca tcatcgaaca gtacagcgcg ttcaacgttc cggaaatctc cgaagaaacc   1320
tacgttaacg gcgttctgac ccagggcgaa aacatcgcgg ataacggcgg cctgcgtgaa   1380
tccttccgtg cgtataaaaa atgggtgaac tccaacaacg acgaaccgaa actgccggaa   1440
ctggaaaaat acaccagcga acagatgttc ttcatcgctt actcccagac ctggtgtcag   1500
gttaaaacca agcaagcct gcagaaccag atcctgagcg acccgcactc tccgggcaaa   1560
ttccgcagct ggggcccggt gtctaactct aaaagcttca gcaaagcgtt caactgcaaa   1620
ccgagcgatc cgatgaacaa cggcgaaaac agctgcgtgc tgtgg             1665
```

<210> SEQ ID NO 23
<211> LENGTH: 526
<212> TYPE: PRT
<213> ORGANISM: Lepeophtheirus salmonis

<400> SEQUENCE: 23

```
Met Pro Met Gly Val Leu Ala Cys Lys Ser Phe Ser Thr Ser Ser Lys
1               5                   10                  15

Val Gly Ala Ala Gly Gly Ala Glu Val Ser Ser Ile Leu Glu Glu Arg
            20                  25                  30

Ile Leu Gly Ser Ala Pro Lys Ala Asn Leu Glu Glu Thr Gly Arg Val
        35                  40                  45

Leu Ser Ile Gly Asp Gly Ile Ala Arg Val Tyr Gly Leu Lys Asn Ile
    50                  55                  60

Gln Ala Glu Glu Met Val Glu Phe Ser Ser Gly Leu Lys Gly Met Ala
65                  70                  75                  80

Leu Asn Leu Glu Ala Asp Asn Val Gly Val Val Phe Gly Asn Asp
                85                  90                  95

Lys Leu Ile Lys Glu Gly Asp Val Val Lys Arg Thr Gly Ala Ile Val
            100                 105                 110

Asp Val Pro Val Gly Arg Glu Leu Leu Gly Arg Val Val Asp Ala Leu
        115                 120                 125

Gly Asn Pro Ile Asp Gly Ala Gly Pro Val Asn Thr Ala Thr Arg Gln
    130                 135                 140

Arg Val Gly Ile Lys Ala Pro Gly Ile Ile Pro Arg Gln Ser Val Lys
145                 150                 155                 160

Glu Pro Met Gln Thr Gly Ile Lys Ala Val Asp Ser Leu Val Pro Ile
                165                 170                 175

Gly Arg Gly Gln Arg Glu Leu Ile Ile Gly Asp Arg Gln Thr Gly Lys
            180                 185                 190

Thr Ala Val Ala Ile Asp Ala Ile Ile Asn Gln Lys Arg Phe Asn Asp
        195                 200                 205

Ala Gly Asp Glu Lys Lys Lys Leu Tyr Cys Ile Tyr Val Ala Ile Gly
    210                 215                 220

Gln Lys Arg Ser Thr Val Ala Gln Ile Val Lys Arg Leu Thr Asp Thr
225                 230                 235                 240

Asp Ala Met Lys Tyr Ser Ile Val Val Ser Ala Thr Ala Ser Asp Ala
                245                 250                 255

Ala Pro Leu Gln Tyr Leu Ala Pro Tyr Ser Gly Cys Ala Met Gly Glu
            260                 265                 270
```

```
Phe Phe Arg Asp Asn Gly Met His Ala Leu Ile Ile Phe Asp Asp Leu
            275                 280                 285

Ser Lys Gln Ala Val Ala Tyr Arg Gln Met Ser Leu Leu Leu Arg Arg
        290                 295                 300

Pro Pro Gly Arg Glu Ala Tyr Pro Gly Asp Val Phe Tyr Leu His Ser
305                 310                 315                 320

Arg Leu Leu Glu Arg Ala Ala Lys Met Ser Asp Thr Gln Gly Gly Gly
                325                 330                 335

Ser Leu Thr Ala Leu Pro Val Ile Glu Thr Gln Ala Gly Asp Val Ser
            340                 345                 350

Ala Tyr Ile Pro Thr Asn Val Ile Ser Ile Thr Asp Gly Gln Ile Phe
        355                 360                 365

Leu Glu Thr Glu Leu Phe Tyr Lys Gly Ile Arg Pro Ala Ile Asn Val
    370                 375                 380

Gly Leu Ser Val Ser Arg Val Gly Ser Ala Ala Gln Thr Lys Ser Met
385                 390                 395                 400

Lys Gln Val Ala Gly Ser Met Lys Leu Glu Leu Ala Gln Tyr Arg Glu
                405                 410                 415

Val Ala Ala Phe Ala Gln Phe Gly Ser Asp Leu Asp Ala Ala Thr Gln
            420                 425                 430

Gln Leu Leu Asn Arg Gly Val Arg Leu Thr Glu Leu Leu Lys Gln Gly
        435                 440                 445

Gln Tyr Val Pro Met Ala Ile Glu Asp Gln Val Ala Val Ile Tyr Cys
    450                 455                 460

Gly Val Arg Gly Phe Leu Asp Lys Leu Asp Pro Ala Lys Ile Thr Asp
465                 470                 475                 480

Phe Glu Lys Lys Phe Leu Glu His Val Arg Ser Ser Gln Lys Pro Leu
                485                 490                 495

Leu Asp Gln Ile Ala Lys Asp Gly His Leu Ser Asp Thr Ser Asp Lys
            500                 505                 510

Ala Leu His Lys Val Val Asp Phe Leu Ala Thr Tyr Gln
        515                 520                 525

<210> SEQ ID NO 24
<211> LENGTH: 1578
<212> TYPE: DNA
<213> ORGANISM: Lepeophtheirus salmonis

<400> SEQUENCE: 24
atgccgatgg gcgttctggc gtgcaaatct ttcagcacct cttctaaagt tggcgcggca    60
ggcggcgctg aagtttctag catcctggaa gaacgtatcc tgggtagcgc cccgaaagct   120
aacctggaag aaaccggtcg cgttctgtct attggtgatg cattgcgcg cgtttatggc    180 ctgaaaaaca tccaggcgga agaaatggtt gaattcagca gcggtctgaa aggcatggcg   240
ctgaacctgg aagctgataa cgttggcgtg gttgttttcg gtaacgataa acttattaaa   300
gaaggtgatg ttgttaaacg taccggtgct atcgttgacg tgccggttgg tcgtgaactg   360
ctgggccgtg ttgtggatgc cctgggaaac ccaatcgatg gcgcgggtcc ggtgaacacc   420
gcgacccgcc agcgcgtggg tatcaaagcg ccgggtatca tcccgcgtca gtctgtaaaa   480
gaaccgatgc agaccggcat taagcggtt gactctctgg ttccgattgg ccgcggccag   540
cgtgaactga tcattggcga ccgtcagact ggcaaaaccg cggttgccat cgacgctatc   600
atcaaccaga acgtttcaa cgatgcgggc gatgaaaaga aaaactgta ctgcatttac   660 gttgctatcg gtcagaaacg ttctaccgtt gcgcagatcg ttaaacgtct gaccgacacc   720
```

-continued

```
gacgcaatga aatactctat tgttgttagc gcgaccgcca gcgatgctgc gccgctgcag     780
tacctggctc cgtacagcgg ctgtgctatg ggggaattct tccgtgataa cggtatgcat     840
gctctgatca tcttcgatga tttatctaaa caggctgtag cctaccgtca gatgagcttg     900
ctgctgcgtc gcccgccggg ccgtgaagcg tatccaggtg atgttttcta cctgcactct     960
cgcttgctgg agcgtgctgc gaaaatgagc gacacccagg gtggtggttc cctgaccgca    1020
ctgccggtga tcgaaaccca ggcgggcgat gttagcgctt acatcccgac caacgtgatc    1080
agcattaccg atggccagat tttcctggaa accgaactgt tctacaaagg catccgtccg    1140
gccatcaacg tgggtctgtc cgtgagccgc gttggttccg cggcacagac caaatccatg    1200
aaacaggttg cgggtagcat gaaactggaa ctggcacagt accgtgaagt tgcagccttc    1260
gcgcagttcg gctctgatct ggacgctgca acccagcagc tgctgaaccg tggtgttcgt    1320
ctgaccgaac tgctgaaaca gggccagtac gttccgatgg cgattgaaga tcaggttgct    1380
gtgatctact gcggcgttcg tggtttcctg gacaaactgg atccggcgaa aattaccgat    1440
ttcgagaaaa aattcctgga acacgtgcgt agcagccaga aaccgctgct ggaccagatc    1500
gctaaagatg gccacctgag cgatacctcc gataaagctc tgcataaagt tgttgttgac    1560
ttcctggcga cctatcag                                                  1578
```

<210> SEQ ID NO 25
<211> LENGTH: 515
<212> TYPE: PRT
<213> ORGANISM: Lepeophtheirus salmonis

<400> SEQUENCE: 25

```
Val Glu Leu Ser Val Lys Cys Lys Asp Ile Thr Asn Lys Asp Met Met
1               5                   10                  15

Ser Lys Ser Asp Pro Ile Cys Leu Val Lys Gln Lys Thr Gly Val Asp
            20                  25                  30

Lys Phe Glu Glu Leu Gly Arg Thr Glu Gln Ile Lys Asp Cys Leu Ser
        35                  40                  45

Pro Glu Phe Met Lys Lys Ile Val Val Pro Tyr Asn Phe Glu Glu Arg
    50                  55                  60

Gln Glu Leu Arg Phe Glu Leu Trp Asp Val Asp Asn Ile Lys Lys Lys
65                  70                  75                  80

Val Glu Asp Gln Lys Leu Leu Gly Tyr Val Asp Val Ser Leu Gly Lys
                85                  90                  95

Ile Val Asn Ala Arg Gly Ile Glu Ala Lys Ile Glu Lys Gly Lys Gly
            100                 105                 110

Ser Met Ile Ile Val Ala Lys Glu Ala Ser Ser Glu Gln Ser Ser Ile
        115                 120                 125

Gly Lys Leu His Leu Gln Phe Gly Ala Ser Lys Leu Glu Asn Lys Asp
    130                 135                 140

Thr Phe Gly Lys Ser Asp Pro Phe Phe His Ile Ser Lys Ser Ile Ser
145                 150                 155                 160

Ala Thr Asp Phe Met Lys Val Tyr Glu Ser Glu Trp Ile Lys Asn Asp
                165                 170                 175

Leu Asn Pro Thr Trp Lys Pro Phe Ser Met Ser Leu Asn Asp Leu Cys
            180                 185                 190

Asp Gly Glu Leu Asn Arg Leu Leu Lys Ile Asp Val Phe Asp Tyr Ser
        195                 200                 205

Ser Asn Gly Lys His Asp Phe Ile Gly Glu Phe Glu Thr Ser Val Ser
```

```
                    210                 215                 220
        Gln Met Met Asn Lys Arg Ser Phe Glu Val Ile Asn Pro Lys Lys
        225                 230                 235                 240

Glu Lys Lys Lys Tyr Thr Asn Ser Gly Val Leu Asn Ile Ile Ser Phe
                        245                 250                 255

Asn Asn Asp Ser Pro Pro Ser Phe Leu Asp Phe Ile Gln Gly Met
                    260                 265                 270

Val Met Asn Phe Ser Val Ala Ile Asp Phe Thr Ala Ser Asn Gly Asn
                    275                 280                 285

Ile Arg Ser Arg Leu Ser Leu His His Arg Gly Asp Glu Gly Glu Asn
        290                 295                 300

Asp Tyr Thr Val Ala Ile Gln Thr Val Gly Asp Ile Ile Glu Asp Tyr
        305                 310                 315                 320

Asp Thr Asp Lys Lys Phe Pro Ala Phe Gly Phe Gly Ala Arg Leu Pro
                        325                 330                 335

Pro Asn Gly Glu Ile Ser His Asp Phe Phe Leu Asn Leu Lys Glu Asn
                        340                 345                 350

Asn Pro Phe Cys Glu Gly Val Arg Gly Ile Leu Asp Ala Tyr Tyr Ser
                    355                 360                 365

Thr Val Asp Ala Val Glu Leu Tyr Gly Pro Thr Asn Phe Ser Pro Cys
        370                 375                 380

Ile Asn Arg Ile Lys Ala Ile Ala Gln Ser His Gln Asp Gly Lys Gln
        385                 390                 395                 400

Tyr Tyr Val Leu Leu Ile Leu Thr Asp Gly Ala Ile Thr Asp Met Ala
                        405                 410                 415

Glu Thr Lys Lys Thr Ile Val Glu Ala Ser Asn Leu Pro Met Ser Ile
                        420                 425                 430

Ile Ile Ile Gly Val Gly Ser Ala Asp Phe Ser Ser Met Ile Glu Leu
                    435                 440                 445

Asp Ser Asp Asp Ala Leu Leu Lys Asp Glu Asp Gly Asn Val Ala Ala
                    450                 455                 460

Arg Asp Ile Val Gln Phe Val Glu Met Ala Lys Tyr Val Lys Lys Ala
        465                 470                 475                 480

Glu Asn Gly Asp Ile Phe Trp Asp Arg Ala Ser Leu Ala Tyr Gln Val
                        485                 490                 495

Met Val Glu Ile Pro Lys Gln Val Leu Glu Trp Thr Ser Lys Arg Gly
                    500                 505                 510

Ile Lys Pro
                515

<210> SEQ ID NO 26
<211> LENGTH: 1545
<212> TYPE: DNA
<213> ORGANISM: Lepeophtheirus salmonis

<400> SEQUENCE: 26
gtggaactga gcgtcaaatg caaagatatc accaacaaag atatgatgtc caaaagcgat     60
ccgatctgcc tggttaaaca gaaaaccggc gttgacaaat cgaagaact gggccgtacg     120 gaacagatca aagactgcct gagcccggaa tttatgaaga aatcgttgt ccgtacaac     180 ttcgaagaac gccaggaact gcgcttcgaa ctgtgggatg tcgataacat caagaaaaaa     240
gttgaagacc agaaactgct gggctatgtt gatgttagcc tgggcaaaat cgtgaacgcg     300
cgtggaatcg aagcgaaaat cgaaaaaggt aaaggcagca tgatcatcgt tgcgaaagaa     360
```

```
gcgtcctctg aacagagcag catcggcaaa ctgcatctgc agttcggcgc gagcaaactg    420
gaaaacaaag ataccttttgg taaatccgac ccgttcttcc atatctctaa aagcatcagc    480
gcgaccgact ttatgaaagt ttacgaatcc gaatggatca aaaacgatct gaacccgacc    540
tggaaaccgt tctctatgtc gctgaacgac ctgtgcgacg gcgaactgaa ccgtctgctg    600
aaaatcgacg ttttcgatta tagctctaac ggcaaacacg acttcatcgg cgaattcgaa    660
accagcgtgt cccagatgat gaacaaacgg agcttcgaag ttatcaaccc gaagaaaaaa    720
gaaaagaaaa aatacaccaa cagcggtgtg ctgaacatca tcagctttaa caacgacagc    780
ccgccgtcct tcctggattt catccagggc ggtatggtta tgaacttcag cgttgccatc    840
gatttcactg cgtctaacgg taacatccgt tctcgtctgt ccctgcacca tcgtggcgac    900
gaaggtgaaa acgattacac cgtggccatc cagaccgttg gcgatatcat tgaagactat    960
gataccgata aaaaattccc ggccttcggc ttcggcgcgc gtctgccgcc gaacggcgaa   1020
atcagccacg acttcttcct gaacctgaaa gagaacaacc cgttctgcga aggtgtgcgt   1080
ggcatcctgg atgcgtacta ctctaccgtc gacgcggttg aactgtacgg cccgaccaac   1140
ttctccccgt gcatcaaccg tattaaagcg atcgcgcaga gccaccagga tggcaaacag   1200
tactacgtcc tgctgattct gaccgacggc gcgatcaccg acatggccga aaccaaaaag   1260
accatcgtgg aagcgagcaa cctgccgatg tctatcatca tcatcggcgt gggcagcgcg   1320
gatttctcat ctatgatcga actggacagt gatgatgcat tgttaaaaga tgaggatggt   1380
aacgttgccg ctcgtgatat cgttcagttc gttgaaatgg ccaaatacgt gaagaaagcc   1440
gaaaacggtg acatcttctg ggatcgcgct tctttagcgt accaggtcat ggtagaaatc   1500
ccgaaacagg tgctggagtg gacctctaaa cgcggcatta aaccg                  1545
```

```

<210> SEQ ID NO 27
<211> LENGTH: 567
<212> TYPE: PRT
<213> ORGANISM: Lepeophtheirus salmonis

<400> SEQUENCE: 27

Met Pro Lys Ala Val Asn Val Arg Val Thr Thr Ile Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Ile Trp Phe Phe Gly Leu Gln
        35                  40                  45

Tyr Thr Asp Thr Lys Gly Phe Ser Thr Trp Leu Lys Leu Asn Lys Lys
    50                  55                  60

Val Met Val Gln Asp Val Lys Lys Glu Thr Pro Leu Gln Phe Lys Phe
65                  70                  75                  80

Arg Ala Lys Phe Tyr Pro Glu Asp Val Ala Glu Glu Leu Ile Gln Asp
                85                  90                  95

Ile Thr Leu Arg Leu Phe Tyr Leu Gln Val Lys Asn Ala Ile Leu Ser
            100                 105                 110

Asp Glu Ile Tyr Cys Pro Pro Glu Thr Ser Val Leu Leu Ala Ser Tyr
        115                 120                 125

Ala Val Gln Ser Lys His Gly Asp Phe Gln Lys Asp Phe His Val Ala
    130                 135                 140

Gly Phe Leu Ala Asn Asp Arg Leu Leu Pro Glu Arg Val Thr Gln Gln
145                 150                 155                 160

His Arg Leu Asn Arg Glu Gln Trp Glu Lys Arg Ile Thr Glu Trp Tyr
```

```
            165                 170                 175
Ser Glu His Lys Gly Met Met Arg Glu Asp Ala Met Met Glu Tyr Leu
            180                 185                 190

Lys Ile Ala Gln Asp Leu Glu Met Tyr Gly Val Asn Tyr Phe Glu Ile
            195                 200                 205

Lys Asn Lys Lys Gly Thr Glu Leu Trp Leu Gly Val Asp Ala Leu Gly
            210                 215                 220

Leu Asn Ile Tyr Glu Lys Asp Arg Leu Thr Pro Lys Ile Gly Phe
225                 230                 235                 240

Pro Trp Ser Glu Ile Arg Asn Ile Ser Phe Asn Asp Arg Lys Phe Val
                245                 250                 255

Ile Lys Pro Ile Asp Ala Lys Ala Pro Asn Phe Val Phe Phe Ala Pro
                260                 265                 270

Arg Leu Arg Ile Asn Lys Arg Ile Leu Thr Leu Cys Met Gly Asn His
                275                 280                 285

Glu Leu Tyr Met Arg Arg Lys Pro Asp Thr Ile Glu Val Gln Gln
            290                 295                 300

Met Lys Ala Gln Asn Lys Glu Glu Lys Leu Ala Lys Gln Glu Arg
305                 310                 315                 320

Glu Lys Leu Gln Arg Glu Ile Ala Ala Arg Glu Lys Ala Glu Arg Ile
                325                 330                 335

Gln Ala Glu Tyr Glu Asp Arg Leu Lys Ala Met Gln Glu Asp Met Glu
                340                 345                 350

Lys Arg Gln Lys Ala Leu Leu Glu Ala Gln Glu Gln Ile Lys Lys Leu
                355                 360                 365

Glu Ser Val Leu Arg Glu Thr Gln Asp Ala Lys Gln Glu Leu Glu Glu
370                 375                 380

Ser Gln Asn Glu Leu Lys Asp Met Met Arg Arg Leu Glu Asp Asp Lys
385                 390                 395                 400

Asn Leu Glu Ile Glu Glu Arg Thr Arg Leu Gln Asp Glu Ile Ala Arg
                405                 410                 415

Lys Gln Ser Glu Val Asn Asp Ile Tyr Thr Gln Val Gln Thr Lys Glu
                420                 425                 430

Gln Glu Asn Met Glu Leu Gln Lys Glu Met Asp Asp Ala Arg Arg Lys
                435                 440                 445

His Glu Glu Ala Thr Ile Ala Leu Val Ala Ala Thr Thr Thr Pro Lys
                450                 455                 460

His His His Leu Glu Glu Asp Asn Asp Asp Glu Val Ser Asn Ser
465                 470                 475                 480

Glu Arg Asp Leu His Val Pro Ser Asp Pro Ile Asp Pro Val Ser
                485                 490                 495

Asp Arg Leu Leu Leu Val Glu Arg Asn Glu Arg Leu Gln Asn Gln Leu
                500                 505                 510

Lys Ser Leu Lys Glu Asp Leu Ser His Thr Arg Asp Glu Gly Glu Glu
                515                 520                 525

Thr Thr Met Asp Arg Ile His Lys Glu Asn Val Lys Gln Gly Arg Asp
530                 535                 540

Lys Tyr Lys Thr Leu Arg Glu Val Arg Lys Gly Asn Thr Lys Arg Arg
545                 550                 555                 560

Val Asp Gln Phe Glu Asn Met
                565
```

<210> SEQ ID NO 28

<211> LENGTH: 1701
<212> TYPE: DNA
<213> ORGANISM: Lepeophtheirus salmonis

<400> SEQUENCE: 28

```
atgcctaaag cggtgaacgt tagagtgacg accattgacg ctgagcttga gttcgcgatc      60
cagcctaaca ccacaggtaa acagctgttt gatcaggtag tgaaaaccat aggtctgcgt     120
gaaatctggt tcttcggcct gcagtacacc gataccaaag gtttctctac ctggctgaaa     180
ctgaacaaaa aagtgatggt gcaggatgtt aaaaaagaaa ccccgctgca gttcaaattc     240
cgtgcaaaat ctacccggaa gacgtggcg aagaactga tccaggacat acccctgcgt       300
ctgttctatc tgcaggttaa aaacgcgatt ctgagtgatg agatctactg cccgcctgaa     360
actagcgttc tgttagctag ctacgcggtt caatcaagc acggtgactt tcaaaaagat      420
ttccatgttg cgggcttcct ggcgaacgat cgcctgctgc cggaacgtgt tacccagcag    480
caccgtctga ccgtgaaca gtgggaaaaa cgtatcaccg aatggtattc cgaacataaa    540
ggcatgatgc gcgaagacgc gatgatgaa tatctgaaaa tcgcgcagga tctgaaaatg     600
tatggcgtga actacttcga atcaagaac aaaaaaggca ctgaactgtg gctgggcgtg     660
gacgcactgg gcctgaacat ctacgaaaaa gatgatcgcc tgaccccgaa atcggtttc     720
ccgtggagcg aaatccgtaa catcagcttc aacgaccgca aattcgtcat caaaccgatt     780
gatgctaaag cgccgaactt cgtgttcttc gctccgcgtc tgcgcatcaa caaacgtatc    840
ctgacctgt gtatgggcaa ccacgaactg tacatgcgtc gtcgcaaacc ggataccatt     900
gaagttcagc agatgaaagc acagaacaaa gaagaaaaac tggcgaaaca gcaggaacgt    960
gaaaaactgc agcgtgaaat cgcggcgcgt gaaaagctg aacgcatcca ggcggaatac   1020
gaagatcgtc tgaaagcgat gcaggaagat atggaaaaac gtcagaaagc gctgctggaa   1080
gcacaggaac agatcaaaaa actggaatcc gttctgcgcg aaacccagga tgcgaaacag   1140
gaactggaag aatctcagaa cgaactgaaa gatatgatgc gtcgtctgga agacgacaaa   1200
aacctggaaa tcgaagaacg tactcgcctg caggacgaaa tcgcccgcaa acagagcgaa   1260
gttaacgata tctacacca ggtacagacc aagaacagg aaaacatgga actgcagaaa     1320
gaaatggatg acgcgcgtcg taaacacgaa gaagcgacta tcgccctggt tgcggcgacc   1380
accacccga acaccatca cctggaagaa gatgataacg acgatgaagt ttctaactct   1440
gaacgcgacc tgcacgtgcc gagcgacccg atcgacgacc cggtttctga tcgtctgctg   1500
ctggttgaac gtaacgaacg tctgcagaac cagctgaaat ccctgaaaga gacctgagc   1560
cacacccgtg acgaaggcga agaaaccacc atggaccgta tccacaaaga aaacgttaaa   1620
cagggtcgtg ataaatacaa aaccctgcgt gaagttcgta aggtaacac caaacgtcgt   1680
gttgatcagt tcgaaaacat g                                              1701
```

<210> SEQ ID NO 29
<211> LENGTH: 206
<212> TYPE: PRT
<213> ORGANISM: Lepeophtheirus salmonis

<400> SEQUENCE: 29

```
Met Asn Val Pro Ser Ser Val Ser Leu Val Leu Ile Leu Ala Ser Thr
1               5                   10                  15

Cys His Ala Leu Met Phe His Leu Glu Pro Asn Gly Arg Lys Cys Leu
            20                  25                  30

Lys Glu Glu Ile Asn Lys Asp Ile Leu Val Ser Gly Glu Tyr Glu Val
```

```
                35                  40                  45
Thr Glu Val Pro Gly Gln Val Val Asp Leu Ile Val Val Asp Ser Lys
 50                  55                  60

Gly Gln His Phe Val Ser Arg Gln Asn Ala Asp Lys Gly Lys Phe Ala
 65                  70                  75                  80

Phe Thr Thr Asp Glu Thr Asn Asp Ala Phe Glu Val Cys Phe Ile Ser
                 85                  90                  95

Gln Ile Pro Ala Gly His His Gly Ser Gln Gln Glu Ile Phe Leu Ser
            100                 105                 110

Val Lys His Gly Val Glu Ala Lys Ser Tyr Glu Gly Leu Gly Asp Ala
        115                 120                 125

Ala Lys Leu Lys Pro Leu Glu Val Glu Leu Lys Arg Leu Glu Asp Leu
    130                 135                 140

Ser Glu Ser Ile Val Gln Asp Phe Ala His Met Arg Arg Arg Glu Glu
145                 150                 155                 160

Glu Met Arg Asp Thr Asn Glu Ser Thr Asn Asn Arg Val Leu Tyr Phe
                165                 170                 175

Ser Ile Phe Ser Met Cys Cys Leu Cys Ser Leu Ala Thr Trp Gln Val
            180                 185                 190

Leu Tyr Leu Arg Lys Tyr Phe Lys Ser Lys Lys Leu Ile Glu
        195                 200                 205

<210> SEQ ID NO 30
<211> LENGTH: 618
<212> TYPE: DNA
<213> ORGANISM: Lepeophtheirus salmonis

<400> SEQUENCE: 30
atgaacgttc cgagctctgt ttctctggtt ctgatcctgg cgagcacctg ccacgcgctg      60
atgttccacc tggaaccgaa cggtcgcaaa tgcctcaaag aagaaatcaa caaagatatc     120
ctggtaagtg gtgaatatga agttacggaa gtgcctggtc aggttgttga cctgatcgta     180
gtcgactcta aaggtcagca ctttgtttcc cgccagaacg cagataaagg taaattcgcg     240
ttcaccaccg atgaaaccaa cgacgcgttc gaagtttgct tcatcagcca gatcccggcg     300
ggtcaccacg gctctcagca ggaaatcttc ctgagtgtta acatggtgt tgaagcgaaa      360
agctacgaag actgggtga tgcggcgaaa ctgaaaccgc tggaagttga gctgaaacgt     420
ctggaagatc tgtcggaaag catcgttcag gatttcgcgc acatgcgtcg tcgtgaagaa     480
gaaatgcgag ataccaacga atctaccaac aaccgtgttc tgtacttcag catcttcagc     540
atgtgctgcc tgtgctctct ggcgacctgg caggttctgt acctgcgtaa atacttcaaa     600
tctaaaaaac ttatcgaa                                                   618

<210> SEQ ID NO 31
<211> LENGTH: 711
<212> TYPE: PRT
<213> ORGANISM: Lepeophtheirus salmonis

<400> SEQUENCE: 31

Met Val Asp Glu Ile Gln Glu Lys Asp Lys Glu Ile Tyr Glu Leu Leu
  1               5                  10                  15

Ser Arg Ile Lys Ser Gln Asp Met Glu Leu Glu Lys Leu Asn Ala Asn
             20                  25                  30

Phe Glu Gln Trp Lys Gly Ile Lys Asn Asp Leu Glu Asn Lys Ile Ser
         35                  40                  45
```

```
Ile Leu Gln Arg Asp Leu Asp Glu Lys Tyr Gly Val Gln Glu Asn
 50                  55                  60
Asn Thr Val Ile Asp Gly Leu Lys Ile Glu Leu Gln Lys Leu Thr Glu
 65                  70                  75                  80
Gln Lys Arg Glu Cys Glu Ser Phe Ser Asn Ala Glu Ile Gln Arg Ile
                 85                  90                  95
Lys Glu Thr Val Glu Lys Leu Glu Ser Glu Asn Ile Ser Ile His Gln
                100                 105                 110
Gly Ile Gln Glu Lys Asp Lys Ala Phe Ala Leu Leu Glu Phe Gln Asn
            115                 120                 125
Lys Ser Leu Thr Gln Gly Asn Lys Gln Ser Ile Ile His Ile Asp Glu
130                 135                 140
Met Lys Ala Leu Asn Thr Cys Leu Glu Asn Lys Val Lys Glu Leu Gln
145                 150                 155                 160
Lys Asn Phe Glu Leu Ser Ser Thr Arg Leu Asp Glu Ala Asn Ile Lys
                165                 170                 175
Ile Ala Glu Asn Glu Lys Glu Met Asn Leu Val Asn Thr Gln Leu Ile
            180                 185                 190
Thr Val Thr Asp Glu Asn Gln Glu Trp Gln His Arg Phe Asp Glu Leu
            195                 200                 205
Thr Asn Gln Asn His Ser Phe Ala Lys Glu Ile Glu Ile Leu Lys Ser
210                 215                 220
Ser Leu Asp Gly Glu Asn Ser Lys Asn Asn Met Asp Phe Lys Leu Leu
225                 230                 235                 240
Glu Gly Lys Asn Arg Glu Leu Glu Ser Phe Leu Glu Lys Ala Gln Leu
                245                 250                 255
Arg Ile Glu Asp Gln Gly Ser Asn Ile His Asn Leu Gln Leu Lys Leu
            260                 265                 270
Lys Ser Lys Asn Glu Lys Phe Ile Asn Leu Glu Asn Asn Ile Ile Phe
            275                 280                 285
Ser Asn Glu Gln Lys Leu Gln Leu Leu Ser Asp Val Glu Ser Tyr Lys
290                 295                 300
Asn Thr Ser Arg Ser Lys Glu Asp Asp Ile Lys Glu Leu Gln Gln Leu
305                 310                 315                 320
Val Asp Ser Leu Asn Asn Glu Lys Arg Asp Leu Thr Thr Arg Cys Asp
                325                 330                 335
Ala Tyr Ser Thr Lys Lys Leu Gln Met Glu Ser Asp Phe Asn Glu Cys
            340                 345                 350
Lys Asn Glu Leu Arg Ile Cys Glu Leu Asn Thr Lys Glu Leu Gln Ser
            355                 360                 365
Cys Val Lys Ser Tyr Glu Ile Glu Leu Glu Asn Val Lys Phe Gln Leu
370                 375                 380
Gly Glu Cys Ser Arg Leu Gln Ser Ile Leu Asp Glu Arg Lys Lys
385                 390                 395                 400
Phe Glu Val Glu Lys Ile Lys Tyr Gln Glu Asp Ile Leu Thr His Ser
                405                 410                 415
Arg Ser Asn Asn Glu Glu Ile Ala Gln Phe Lys Ile Lys Cys Asp Lys
            420                 425                 430
Leu Glu Ser Glu Met Ser Lys Leu Lys His Asp Asp Ser Glu Phe Val
            435                 440                 445
Glu Leu Lys Ser Ala Asn Ser Glu Leu Leu Ser Lys Ile Thr Cys Leu
450                 455                 460
Ser Ser Gln Ile Thr Leu Leu Leu Ser Glu Lys Glu Lys Ile Asp Glu
```

```
                465                 470                 475                 480
Asp Leu Val Arg Leu Thr Asp Ser Asn Glu Ala Val Leu Gln Thr Lys
                    485                 490                 495

Gln His Glu Ile Ile Glu Leu Lys Glu Lys Ile Asn Ser Ile Leu Lys
                    500                 505                 510

Asp His Lys Lys Glu Ile Glu Asp Thr His Asn Glu Tyr Lys Glu Lys
                    515                 520                 525

Met Glu Ser Ser Leu Tyr Asp Gly Asp Ser Val Lys Glu Ile Ala
                    530                 535                 540

Ser Leu Gln Asn Leu Val Lys Ser Lys Glu Asn Asp Ala Asn Leu Leu
545                 550                 555                 560

Asn Glu Gln Val Asn His Lys Lys Glu Ala Ile Thr Cys Leu Glu Asn
                    565                 570                 575

Arg Leu Ser Gln Glu Ala Val Ala Leu Ser Glu Val Leu Asn Asn
                    580                 585                 590

Lys Lys Leu Val Ile Glu Ile Glu Leu Lys Lys Leu Asn Cys Gln
                    595                 600                 605

Leu Glu Asn Asn Ile Leu Glu Val Ser Glu Ser Gln Ser Lys Lys Glu
                    610                 615                 620

Phe Asp Asn Leu Arg Gln Thr Leu Lys Ser Cys Lys Leu Glu Leu Ala
625                 630                 635                 640

Ser Thr Gln Val Glu Ser Thr Phe Lys Asp Lys Glu Ile Asp Thr Leu
                    645                 650                 655

Arg Lys Asp Ile Asn Phe Leu Ser Lys Lys Ser Asn Thr Tyr Lys Glu
                    660                 665                 670

Glu Leu Arg Lys Val Arg Asn Glu Asn Met Asp Thr Thr Ile Tyr Asn
                    675                 680                 685

Asn Glu Ser Lys Leu Lys Lys Arg Asn Glu Thr Lys Val Glu Arg Gln
                    690                 695                 700

Asn Asp Ala Met His Ser Val
705                 710
```

<210> SEQ ID NO 32
<211> LENGTH: 2133
<212> TYPE: DNA
<213> ORGANISM: Lepeophtheirus salmonis

<400> SEQUENCE: 32

```
atggttgacg aaatccagga aaagacaaa gaaatctacg agctgctgtc ccgtatcaaa      60
tcccaggaca tggaactcga aaaactgaac gcgaactttg aacagtggaa aggcatcaaa     120
aacgacctgg agaacaaaat ctccattctg cagcgcgacc tggatgaaaa atacggcgtg    180
gtgcaggaga caacacggt gatcgacggc ctgaaaatcg agctgcagaa actgaccgaa     240
cagaaacgtg aatgcgaaag cttcagcaac gcagagattc agcgtatcaa agaaaccgtt    300
gaaaagctgg agtcggaaaa catcagcatc accagggca tccaggagaa ggacaaggcc    360
ttcgctctcc tggaattcca gaacaaatcc ctgacgcagg taacaaaca gtccatcatc     420
cacatcgacg atgaaggc gctgaacacc tgccttgaaa acaaggttaa agaactgcag      480
aaaaacttcg agctgagcag cacccgcctg atgaagcca acatcaagat cgcggagaac    540
gagaaggaga tgaacctggt taacacccag ctgatcaccg ttaccgacga accaggag      600
tggcagcacc gttttgacga actgaccaac cagaaccaca gcttcgctaa ggagatcgag    660
atcctgaaaa gcagcctgga cggcgaaaac tccaagaaca catggacttt caaactgctc    720
```

-continued

```
gaaggcaaaa accgcgaact ggagagcttc ctggaaaagg cgcagctgcg catcgaagat     780
cagggtagca acatccacaa cctgcagctg aaactgaaga gcaaaaacga gaaattcatc     840
aacctggaaa acaacattat cttctccaac gaacagaagc tgcagctgct gtccgacgtg     900
gaatcctaca aaacacctc tcgcagcaaa gaggatgata tcaaagaact gcagcagctc     960
gtggactccc tgaacaacga aagcgcgac ctgactaccc ggtgcgacgc gtacagcact    1020
aagaaactgc agatggagag cgacttcaac gaatgcaaga tgaactgcg catctgcgaa    1080 ctgaacacca aagagctgca gagctgcgtg aagtcctatg agatcgagct ggagaacgtc    1140
aaattccagc tgggcgaatg ctcccgtctg cagtctatcc tggatgaaga acgtaaaaaa    1200
ttcgaagttg aaaaaatcaa ataccaggaa gatatcctca ctcactctcg cagcaacaac    1260
gaagaaatcg cacagttcaa gatcaaatgc gataaactgg aaagcgagat gtccaaactg    1320
aaacatgacg actctgaatt tgtggaactc aaatccgcaa atagcgaact gctgtccaaa    1380
atcacctgtc tcagcagcca gattactctg ctgctgagcg aaaaagaaaa gatcgatgaa    1440
gatctggtgc gcttgaccga tagcaacgaa gccgtcctgc agacgaaaca acacgaaatc    1500
atcgaactga agaaaaaaat caactctatc ctgaaagacc ataaaaaaga aattgaagat    1560
acccacaacg aatataaaga aaaatggaa agcagcctgt acgacggtga ttccgttaaa    1620
gaagagatcg cctccctgca gaacctggtt aaatctaagg aaaacgacgc aaacctgctg    1680
aacgagcagg ttaaccacaa gaaagaagcg attacctgcc tggaaaaccg tctgtcccag    1740
gaagcagttg cgctgagcga agtgctgaac aacaacaaaa aactggttat cgaaatcgaa    1800
gaactgaaaa aactgaattg ccagctggaa acaacattc ttgaggtttc tgaatcccag    1860
tctaaaaaag aattcgacaa cttgcgccag actctgaaaa gctgcaaact ggaactggct    1920
tccactcagg tagagtctac tttcaaagat aaagaaattg ataccctgcg taaagatatt    1980
aacttcctgt ctaaaaaatc taacacctac aaagaagaac tgcgtaaagt tcgtaacgaa    2040
aacatggaca ccaccatcta taacaacgaa tctaaactga aaaaacgtaa tgagactaaa    2100
gttgaacgtc agaacgacgc gatgcatagc gtg                                 2133
```

<210> SEQ ID NO 33
<211> LENGTH: 308
<212> TYPE: PRT
<213> ORGANISM: Lepeophtheirus salmonis

<400> SEQUENCE: 33

```
Met Ser Thr Glu Asp Lys Glu Gly Leu Glu Ser Ile Arg Met Leu His
1               5                   10                  15

Ser His Leu Asp Asp Lys Asp Gly Ser Ile Glu Pro Ala Glu Thr
            20                  25                  30

Gly Glu Phe Ile Arg Gly Gly Leu Arg Gly Glu Asp Tyr Ile Lys
        35                  40                  45

Arg Gln Lys Leu Phe His Arg Ser Asp Val Glu Ile Thr Val Leu Asp
    50                  55                  60

Leu Trp Gln Thr Trp Thr Thr Ser Thr Val His Asn Trp Thr Val Asp
65                  70                  75                  80

Gln Thr Ile Glu Trp Leu Leu Ser Val Asp Leu Pro Gln Tyr Lys
            85                  90                  95

Thr Thr Phe Glu Tyr His Ser Val Asn Gly Ser Arg Ile Pro Gln Ile
        100                 105                 110

Ala Val Asn Ser Ser Tyr Leu Thr Lys Val Leu Lys Ile Thr Asn Pro
    115                 120                 125
```

```
Ile His Lys Ser Lys Leu Ser Leu Lys Ala Met Asp Val Val Leu Phe
    130                 135                 140

Gly Pro Pro Lys Glu Pro Ser Ser Phe Phe Lys Asp Val Ile Phe Thr
145                 150                 155                 160

Ile Ile Ile Leu Leu Ala Gly Thr Gly Leu Phe Tyr Ala Tyr His Lys
                165                 170                 175

Asn Lys Lys Ser Gln Asp Gln Leu Lys Lys Met Met Glu Asp Met Asp
            180                 185                 190

Lys Leu Gly Val Ala Glu Arg Asp Leu Leu Asp Leu Gln Ser Lys Leu
        195                 200                 205

Gln Gln Lys Asp Lys Val Ile Lys Asn Ile Arg Ser Val Ser Lys Glu
    210                 215                 220

Leu Asn Gln Val Ser Leu Glu Thr Glu Glu Ile Lys Arg Met Arg Glu
225                 230                 235                 240

Glu Ile Glu Asp Leu Arg Asn Gln Leu Tyr Ala Ala Glu Thr Glu Leu
                245                 250                 255

Glu Asp Lys Cys Trp Ser Ala Pro Pro Thr Leu Gln Leu Trp Leu Gln
            260                 265                 270

Ile Ser Tyr Glu Ile Glu Ser Met Gly Phe Ser Ala Lys Lys Lys Glu
        275                 280                 285

Ala Glu Lys Gln Leu Glu Leu Ala Lys Asp Met Cys Glu Lys Leu Lys
    290                 295                 300

Lys Lys Arg Ser
305
```

<210> SEQ ID NO 34
<211> LENGTH: 924
<212> TYPE: DNA
<213> ORGANISM: Lepeophtheirus salmonis

<400> SEQUENCE: 34

```
atgagcactg aagataaaga aggcctggag agcatccgta tgctgcacag ccacctggat      60
gatgataaag atggtagcat cgaaccggcg aaaccggtg aattcatccg tggtggcgaa     120
ctgcgtggcg aagactacat caaacgccag aaactgttcc accgtagcga tgttgaaatc     180
accgtgctgg atctgtggca gacctggacc accagcaccg tgcacaactg gaccgtggat     240
cagaccatcg agtggctgct gaccagcgtg gacctgccgc agtacaaaac caccttcgaa     300
taccactctg ttaacggcag ccgcatcccg cagatcgcgg ttaacagcag ctacctgacc     360
aaagttctga aaattaccaa cccgatccac aaaagcaaac tgagcctgaa agcgatggac     420
gttgtgctgt tcggtccgcc gaaagaaccg agctctttct tcaaagatgt tatcttcacc     480
atcatcatcc tgctggccgg caccggtctg ttctacgctt accacaaaaa caaaaaatcc     540
caggaccagc tgaaaaagat gatggaagat atggataaac tgggcgttgc ggaacgtgac     600
ctgctggatc tgcagtctaa actgcaacag aaagacaaag tcatcaaaaa cattcgtagc     660
gttagcaaag aactgaacca ggtttctctg gaaaccgaag aaatcaaacg tatgcgtgaa     720
gaaatcgaag atctgcgtaa ccagctgtac gcggcggaaa ccgaactgga agacaaatgc     780
tggtccgccc caccgacctt gcagctgtgg ctgcagattt catacgaaat cgaatccatg     840
ggcttttcag cgaaaaagaa agaagctgag aaacagctgg aactcgctaa agatatgtgc     900
gagaaactca aaagaaacg ctct                                             924
```

US 11,167,017 B2

SEA LICE VACCINE

CROSS REFERENCE TO RELATED APPLICATIONS

This application is a national stage entry of International Application No. PCT/US2017/047095 filed Aug. 16, 2017, which claims priority to the U.S. Provisional Application No. 62/376,016, filed Aug. 17, 2016 the contents of which are incorporated by reference in their entirety.

FIELD OF THE INVENTION

The present invention broadly relates to the field of immunology. More specifically, the invention relates to a vaccine composition to be used in the prevention and/or control of sea lice infestation in fish. In particular, the vaccine is directed towards peptides identified from the gut of sea lice to be used as a vaccine in salmon.

BACKGROUND OF THE INVENTION

Crustaceans of the Caligidae family, commonly known as sea lice, are the most extensively reported ectoparasites in salmonid species, both farmed and wild type (Pike, A W and Wadsworth, S L Advances in Parasitology 2000, 44:233-337, Ragi, V. et al. Aquaculture 2004, 242: 727-733). Global growth of intensive salmonid farming over the last decade has made the control of sea lice one of the main concerns in the industry due to important economic losses and environmental effects generated by these parasites. In 2012 salmon farming reached a worldwide production of over 2,100,000 metric tons. However, growth of the industry is slowing. Between 1991 and 2001, production of Atlantic salmon, the dominant species grown, grew 328%, but only grew 62% between 2001 and 2011. Infestations with sea lice have emerged as a dominant factor limiting growth of the industry.

A wide range of veterinary medicines; hydrogen peroxide, organophosphates, ivermectin, emamectin benzoate, molting regulators and pyrethroids have been used to try to control sea lice infestations; However, the potential for lice to develop resistance is high and has been reported several times in both the salmon louse (*Lepeophtheirus salmonis*) and *C. rogercresseyi* (Vaccine 29 (2011) 2810-2820). Multiple resistances, now present in several regions, exacerbate this situation (International Animal Health Journal Volume 2 Issue 1). However, without any treatment measures, sea lice would probably increase to levels such as to cause significant direct and indirect mortality to stock.

These facts, together with the necessity of reducing costs and threats to wild stocks of salmonids, make the development of new approaches, such as vaccination to control infestation of sea lice in salmon, an imperative. To date, there are no commercial vaccines available against sea lice. Vaccines against *L. salmonis* derived from whole extracts of the parasite were not protective since their administration resulted in only minor changes in *L. salmonis* fecundity [Grayson T H et al. J Fish Biol 1995; 47: 85-94]. The identification of effective vaccine targets for prevention and treatment of sea lice has not yet been successful. There is a distinct need for the development of a vaccine that can be used to prevent and limit the infestation of sea lice.

SUMMARY OF THE INVENTION

The invention provides a novel vaccine composition for the control and prevention of a sea lice infestation. The vaccine of the invention comprises recombinant peptides identified from sea lice formulated into a vaccine, as described herein. The invention further provides polynucleotides encoding the peptides that comprise said vaccine and a host cell comprising the polynucleotides of the invention. The invention further provides a method of using the vaccine of the invention.

One aspect of the present invention provides a vaccine composition for use in controlling or preventing a sea lice infestation comprising an immunologically effective dose of an identified sea louse peptide and a pharmaceutically acceptable carrier. In one embodiment the vaccine composition of the invention comprises a peptide identified from the gut of the sea louse. In one or more embodiments the sea louse peptide is an isolated and recombinant peptide.

In one or more embodiments the vaccine of the present invention is used to control and/or prevent an infestation of a population of sea lice and is selected from the genus *Lepeophtheirus* or *Caligus*. In one embodiment the sea louse comprises the genus *Lepeophtheirus* and is *Lepeophtheirus salmonis*. In one embodiment of the present invention the sea louse comprises the genus *Caligus*. In one embodiment the sea louse is of the genus *Caligus* and comprises *Caligus rogercresseyi*.

In one or more embodiments of the present invention the vaccine composition is used for controlling sea lice infestation in Salmonids. In one embodiment the Salmonid is selected from the group consisting of: salmon, trout and chars. In one embodiment the Salmonid comprises salmon. In one embodiment the salmonid is selected from the genus *Salmo* or the genus *Oncorhynchus*. In one embodiment the Salmonid comprises *Salmo*. In one embodiment the Salmonid comprises wither *Salmo salar* or *Salmo trutta*. In one embodiment the Salmonid comprises *Salmo salar*. In one embodiment the Salmonid comprises *Salmo trutta*. In one embodiment the Salmonid is *Oncorhynchus*. In one embodiment the Salmonid is *Oncorhynchus* and is selected from the group consisting of: *Oncorhynchus mykiss*, *Oncorhynchus nerka*, *Oncorhynchus tshawytscha*, *Oncorhynchus gorbuscha* *Oncorhynchus keta*, *Oncorhynchus kisutch*, and *Oncorhynchus masu*.

In one or more embodiments the vaccine composition of the present invention further comprises a pharmaceutically acceptable adjuvant. In one embodiment the adjuvants of the invention are selected from the group consisting of: muramyl dipeptides, lipopolysaccharides, glucans, glycans, oil-in-water emulsion, Freund's adjuvant and acrylic acid polymers. In one embodiment the adjuvant is a water-in-oil emulsion. In one embodiment the oil in the water-in-oil-emulsion is selected from an animal, vegetable or mineral oil.

In one or more embodiments of the present invention the peptide of the vaccine composition has at least about 80% sequence identity with a peptide that is selected from the group consisting of SEQ ID NO. 1, SEQ ID NO. 5, SEQ ID NO.7, SEQ ID NO.9, SEQ ID NO.13, SEQ ID NO.15 SEQ ID NO.17, SEQ ID NO.19, SEQ ID NO.21, SEQ ID NO. 23, SEQ ID NO. 25, SEQ ID NO. 27, SEQ ID NO.29, SEQ ID NO. 33, and variants or immunogenic fragments thereof. In one or more embodiments of the present invention the peptide of the vaccine composition has at least about 85% sequence identity with a peptide that is selected from the group consisting of SEQ ID NO. 1, SEQ ID NO. 5, SEQ ID NO.7, SEQ ID NO.9, SEQ ID NO.13, SEQ ID NO.15 SEQ ID NO.17, SEQ ID NO.19, SEQ ID NO.21, SEQ ID NO. 23, SEQ ID NO. 25, SEQ ID NO. 27, SEQ ID NO.29, SEQ ID NO. 33 and variants or immunogenic fragments thereof. In one or more embodiments of the present invention the peptide of the vaccine composition has at least about 90% sequence identity with a peptide that is selected from the group consisting of SEQ ID NO. 1, SEQ ID NO. 5, SEQ ID NO.7, SEQ ID NO.9, SEQ ID NO.13, SEQ ID NO. 15 SEQ ID NO.17, SEQ ID NO.19, SEQ ID NO.21, SEQ ID NO. 23, SEQ ID NO. 25, SEQ ID NO. 27, SEQ ID NO.29, SEQ ID NO. 33 and variants or immunogenic fragments thereof. In one or more embodiments of the present invention the peptide of the vaccine composition has at least about 95% sequence identity with a peptide that is selected from the group consisting of SEQ ID NO. 1, SEQ ID NO. 5, SEQ ID NO.7, SEQ ID NO.9, SEQ ID NO.13, SEQ ID NO. 15, SEQ ID NO.17, SEQ ID NO.19, SEQ ID NO.21, SEQ ID NO. 23, SEQ ID NO. 25, SEQ ID NO. 27, SEQ ID NO.29, SEQ ID NO. 33 and variants or immunogenic fragments thereof. In one embodiment the vaccine of the present invention comprises a peptide having at least about 80%, 85%, 90% or 95% sequence identity to SEQ ID NO.1 or a variant or immunogenic fragment thereof. In one embodiment the vaccine of the present invention comprises a peptide having at least about 80%, 85%, 90% or 95% sequence identity to SEQ ID NO.5 or a variant or immunogenic fragment thereof. In one embodiment the vaccine of the present invention comprises a peptide having at least about 80%, 85%, 90% or 95% sequence identity to SEQ ID NO.7 or a variant or immunogenic fragment thereof. In one embodiment the vaccine of the present invention comprises a peptide having at least about 80%, 85%, 90% or 95% sequence identity to SEQ ID NO.9 or a variant or immunogenic fragment thereof. In one embodiment the vaccine of the present invention comprises a peptide having at least about 80%, 85%, 90% or 95% sequence identity to SEQ ID NO.13 or a variant or immunogenic fragment thereof. In one embodiment the vaccine of the present invention comprises a peptide having at least about 80%, 85%, 90% or 95% sequence identity to SEQ ID NO.15 or a variant or immunogenic fragment thereof. In one embodiment vaccine of the present invention comprises a peptide having at least about 80%, 85%, 90% or 95% sequence identity to SEQ ID NO.17 or a variant or immunogenic fragment thereof. In one embodiment the vaccine of the present invention comprises a peptide having at least about 80%, 85%, 90% or 95% sequence identity to SEQ ID NO.19 or a variant or immunogenic fragment thereof. In one embodiment the vaccine of the present invention comprises a peptide having at least about 80%, 85%, 90% or 95% sequence identity to SEQ ID NO.21 or a variant or immunogenic fragment thereof. In one embodiment the vaccine of the present invention comprises a peptide having at least about 80%, 85%, 90% or 95% sequence identity to SEQ ID NO.23 or a variant or immunogenic fragment thereof. In one embodiment the vaccine of the present invention comprises a peptide having at least about 80%, 85%, 90% or 95% sequence identity to SEQ ID NO.25 or a variant or immunogenic fragment thereof. In one embodiment the vaccine of the present invention comprises a peptide having at least about 80%, 85%, 90% or 95% sequence identity to SEQ ID NO.27 or a variant or immunogenic fragment thereof. In one embodiment the vaccine of the present invention comprises a peptide having at least about 80%, 85%, 90% or 95% sequence identity to SEQ ID NO.29 or a variant or immunogenic fragment thereof. In one embodiment the vaccine of the present invention comprises a peptide having at least about 80%, 85%, 90% or 95% sequence identity to SEQ ID NO.33 or a variant or immunogenic fragment thereof.

In one or more embodiments the vaccine of the invention further comprises one or more antigens obtained from bacteria, virus, fungus or parasites other than sea lice. In one embodiment the one or more non-sea lice antigens are selected from the group consisting of *Piscirickettsias* sp. *Aeromonas* sp., *Vibrio* sp., *Listonella* sp., *Moritella viscose*, *Photobacterium damsela*, *Flavobacterium* sp., *Yersinia* sp., *Renibacterium* sp., *Streptococcus* sp., *Lactococcus* sp., *Edwarsiella* sp., *Francisella* sp., *Pseudomonas* sp., *Nocardia* sp., *Mycobacterium* sp., Viral Hemorrhagic Septicemia Virus (VHSV), Infectious Hematopoietic Necrosis virus (IHNV), Infectious Pancreatic Necrosis Virus (IPNV), Spring Viremia of Carp (SVC), Channel Catfish Virus (CCV), Infectious Salmon Anaemia virus (ISAV), pancreatic disease virus (SPDV), Iridovirus, and heart and skeletal muscle inflammation virus (HSMIV), Piscine Myocarditis virus (PMCV), *Saprolegnia* Sp., *Branchiomyces sanguinis*, and *Branchiomyces demigrans* variants or immunogenic fragments thereof.

In one or more embodiments, the vaccine of the invention further comprises at least one or more additional sea louse peptide(s), as described herein. In one embodiment, the one or more isolated sea louse peptide is identified from the gut of a sea louse, as described herein. In one embodiment the one or more sea louse peptide is a recombinant peptide and is isolated, as described herein. In one embodiment the vaccine of the invention further comprises one or more sea louse peptide having at least about 80% sequence identity with a peptide that is selected from the group consisting of SEQ ID NO.1, SEQ ID NO.5, SEQ ID NO.7, SEQ ID NO.9, SEQ ID NO.13, SEQ ID NO.15 SEQ ID NO.17, SEQ ID NO.19, SEQ ID NO.21, SEQ ID NO. 23, SEQ ID NO. 25, SEQ ID NO. 27, SEQ ID NO.29, SEQ ID NO. 33 and variants or immunogenic fragments thereof. In one embodiment of the present invention the vaccine composition further comprises one or more peptides having at least about 85% sequence identity with a peptide that is selected from the group consisting of SEQ ID NO. 1, SEQ ID NO. 5, SEQ ID NO.7, SEQ ID NO.9, SEQ ID NO.13, SEQ ID NO.15 SEQ ID NO.17, SEQ ID NO.19, SEQ ID NO.21, SEQ ID NO. 23, SEQ ID NO. 25, SEQ ID NO.27, SEQ ID NO.29, SEQ ID NO. 33 and variants or immunogenic fragments thereof. In one embodiment of the present invention the vaccine composition further comprises one or more peptides having at least about 90% sequence identity with a peptide that is selected from the group consisting of SEQ ID NO. 1, SEQ ID NO. 5, SEQ ID NO.7, SEQ ID NO.9, SEQ ID NO.13, SEQ ID NO.15 SEQ ID NO.17, SEQ ID NO.19, SEQ ID NO.21, SEQ ID NO. 23, SEQ ID NO. 25, SEQ ID NO. 27, SEQ ID NO.29, SEQ ID NO. 33 and variants or immunogenic fragments thereof. In one embodiment of the present invention the vaccine composition further comprises one or more peptides having at least about 95% sequence identity with a peptide that is selected from the group consisting of SEQ ID NO. 1, SEQ ID NO. 5, SEQ ID NO.7, SEQ ID NO.9, SEQ ID NO.13, SEQ ID NO.15 SEQ ID NO.17, SEQ ID NO.19, SEQ ID NO.21, SEQ ID NO. 23, SEQ ID NO. 25, SEQ ID NO.27, SEQ ID NO.29, SEQ ID NO. 33 and variants or immunogenic fragments thereof. In one embodiment the one or more peptide used in the vaccine of the present invention further comprises a peptide having at least about 80%, 85%, 90% or 95% sequence identity to SEQ ID NO.1 or a variant or immunogenic fragment thereof. In one embodiment the one or more peptide used in the vaccine of the present invention further comprises a peptide having at least about 80%, 85%, 90% or 95% sequence identity to SEQ ID NO.5 or a variant or immunogenic fragment thereof. In one embodiment the one or more peptide used in the vaccine of the present invention further comprises a peptide having at least about 80%, 85%, 90% or 95% sequence identity to SEQ ID NO.7 or a variant or immunogenic fragment thereof. In one embodiment the one or more peptide used in the vaccine of the present invention further comprises a peptide having at least about 80%, 85%, 90% or 95% sequence identity to SEQ ID NO.9 or a variant or immunogenic fragment thereof. In one embodiment the one or more peptide used in the vaccine of the present invention further comprises a peptide having at least about 80%, 85%, 90% or 95% sequence identity to SEQ ID NO.13 or a variant or immunogenic fragment thereof. In one embodiment the one or more peptide used in the vaccine of the present invention further comprises a peptide having at least about 80%, 85%, 90% or 95% sequence identity to SEQ ID NO.15 or a variant or immunogenic fragment thereof. In one embodiment the one or more peptide used in the vaccine of the present invention further comprises a peptide having at least about 80%, 85%, 90% or 95% sequence identity to SEQ ID NO.17 or a variant or immunogenic fragment thereof. In one embodiment the one or more peptide used in the vaccine of the present invention further comprises a peptide having at least about 80%, 85%, 90% or 95% sequence identity to SEQ ID NO. 19 or a variant or immunogenic fragment thereof. In one embodiment the one or more peptide used in the vaccine of the present invention further comprises a peptide having at least about 80%, 85%, 90% or 95% sequence identity to SEQ ID NO.21 or a variant or immunogenic fragment thereof. In one embodiment the one or more peptide used in the vaccine of the present invention further comprises a peptide having at least about 80%, 85%, 90% or 95% sequence identity to SEQ ID NO.23 or a variant or immunogenic fragment thereof. In one embodiment the one or more peptide used in the vaccine of the present invention further comprises a peptide having at least about 80%, 85%, 90% or 95% sequence identity to SEQ ID NO.25 or a variant or immunogenic fragment thereof. In one embodiment the one or more peptide used in the vaccine of the present invention further comprises a peptide having at least about 80%, 85%, 90% or 95% sequence identity to SEQ ID NO.27 or a variant or immunogenic fragment thereof. In one embodiment the one or more peptide used in the vaccine of the present invention further comprises a peptide having at least about 80%, 85%, 90% or 95% sequence identity to SEQ ID NO.29 or a variant or immunogenic fragment thereof. In one embodiment the one or more peptide used in the vaccine of the present invention further comprises a peptide having at least about 80%, 85%, 90% or 95% sequence identity to SEQ ID NO.33 or a variant or immunogenic fragment thereof.

One aspect of the present invention provides a method to vaccinate a Salmonid to prevent or control a sea lice infestation comprising the step of administering the vaccine of the invention. In one embodiment the vaccine is administered by a route selected from the group selected from intraperitoneal injection, intramuscular injection, bath, immersion, and oral administration. In one embodiment the vaccine is administered by intraperitoneal injection.

One aspect of the present invention provides a vector comprising a nucleic acid sequence encoding the peptide of the vaccine of the invention wherein the nucleic acid sequence having at least about 80%, 85%, 90% or 95% sequence identity to the nucleic acid sequences that are selected from the group consisting of: SEQ ID NO. 2, SEQ ID NO. 6, SEQ ID NO. 8, SEQ ID NO. 10, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 34. In one embodiment the nucleic acid coding sequence of the invention is a heterologous sequence that is operably linked to one or more regulatory sequences as part of the vector of the invention. One aspect of the present invention provides a host cell comprising the vector of the present invention.

BRIEF DESCRIPTION OF THE FIGURES

FIG. 1A: Amino acid sequence of the identified sea louse peptide P9: SEQ ID NO. 1

FIG. 1B: Nucleotide coding sequence of the identified sea louse peptide P9: SEQ ID NO. 2

FIG. 2A: Amino acid sequence of the identified sea louse peptide P13: SEQ ID NO. 3

FIG. 2B: Nucleotide coding sequence of the identified sea louse peptide P13: SEQ ID NO. 4

FIG. 3A: Amino acid sequence of the identified sea louse peptide P15: SEQ ID NO. 5

FIG. 3B: Nucleotide coding sequence of the identified sea louse peptide P15: SEQ ID NO. 6

FIG. 4A: Amino acid sequence of the identified sea louse peptide P18: SEQ ID NO. 7

FIG. 4B: Nucleotide coding sequence of the identified sea louse peptide P18: SEQ ID NO. 8

FIG. 5A: Amino acid sequence of the identified sea louse peptide P21: SEQ ID NO. 9

FIG. 5B: Nucleotide coding sequence of the identified sea louse peptide P21: SEQ ID NO. 10

FIG. 6A: Amino acid sequence of the identified sea louse peptide P26: SEQ ID NO. 11

FIG. 6B: Nucleotide coding sequence of the identified sea louse peptide P26: SEQ ID NO. 12

FIG. 7A: Amino acid sequence of the identified sea louse peptide P33: SEQ ID NO. 13

FIG. 7B: Nucleotide coding sequence of the identified sea louse peptide P33: SEQ ID NO. 14

FIG. 8A: Amino acid sequence of the identified sea louse peptide P34: SEQ ID NO. 15

FIG. 8B: Nucleotide coding sequence of the identified sea louse peptide P34: SEQ ID NO. 16

FIG. 9A: Amino acid sequence of the identified sea louse peptide P37: SEQ ID NO. 17

FIG. 9B: Nucleotide coding sequence of the identified sea louse peptide P37: SEQ ID NO. 18

FIG. 10A: Amino acid sequence of the identified sea louse peptide P30: SEQ ID NO.19

FIG. 10B: Nucleotide coding sequence of the identified sea louse peptide P30: SEQ ID NO. 20

FIG. 11A: Amino acid sequence of the identified sea louse peptide P4: SEQ ID NO.21

FIG. 11B: Nucleotide coding sequence of the identified sea louse peptide P4: SEQ ID NO.22

FIG. 12A: Amino acid sequence of the identified sea louse peptide P5: SEQ ID NO.23

FIG. 12B: Nucleotide coding sequence of the identified sea louse peptide P5: SEQ ID NO.24

FIG. 13A: Amino acid sequence of the identified sea louse peptide P12: SEQ ID NO.25

FIG. 13B: Nucleotide coding sequence of the identified sea louse peptide P12: SEQ ID NO.26

FIG. 14A: Amino acid sequence of the identified sea louse peptide P14: SEQ ID NO.27

FIG. 14B: Nucleotide coding sequence of the identified sea louse peptide P14: SEQ ID NO.28

FIG. 15A: Amino acid sequence of the identified sea louse peptide P16: SEQ ID NO.29

FIG. 15B: Nucleotide coding sequence of the identified sea louse peptide P16: SEQ ID NO.30

FIG. 16: Amino acid sequence of the identified sea louse peptide P17: SEQ ID NO.31

FIG. 17: Nucleotide coding sequence of the identified sea louse peptide P17: SEQ ID NO.32

FIG. 18A: Amino acid sequence of the identified sea louse peptide P32: SEQ ID NO.33

FIG. 18B: Nucleotide coding sequence of the identified sea louse peptide P32: SEQ ID NO.34.

BRIEF DESCRIPTION OF THE SEQUENCES

Figures 19A, 19B:
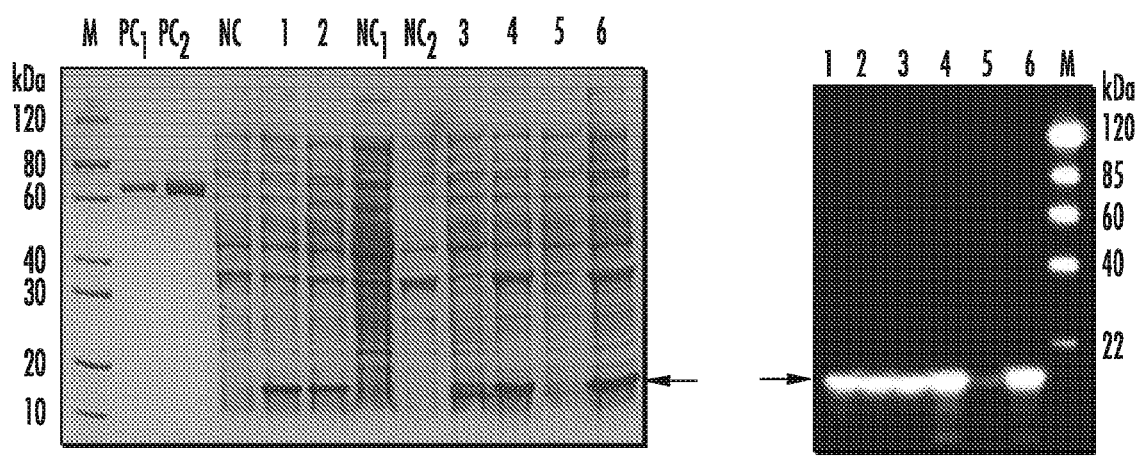
FIG. 19A: Western blot of P33 peptide after expression in *E. coli* BL21 (DE3) cells.
FIG. 19B: Stained SDS-PAGE gel showing IPTG induction of P33 (SEQ ID NO. 13) peptide in transformed *E. coli* BL21 (DE3) cells.
Figure 20:
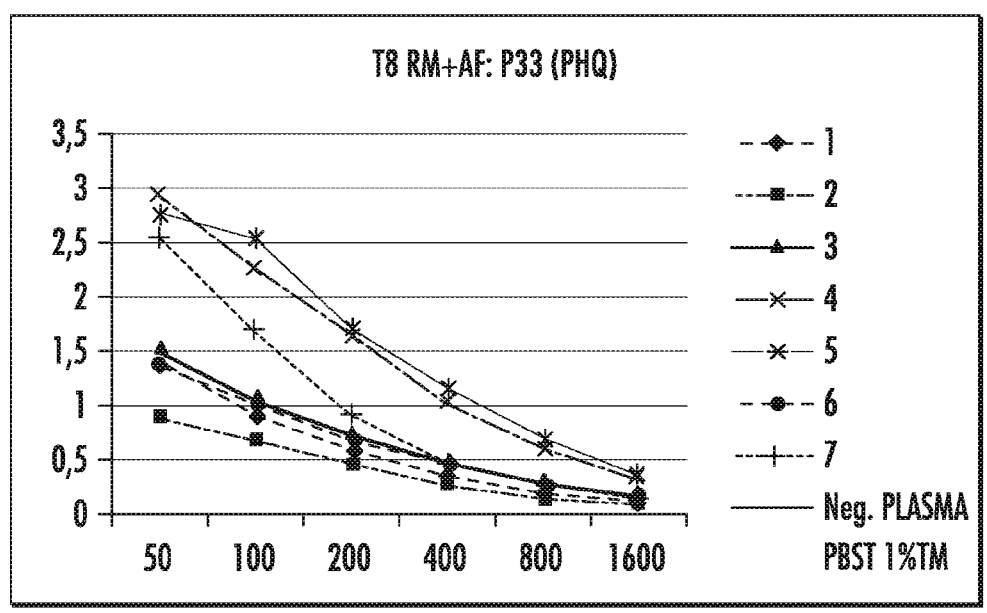
FIG. 20: ELISA results showing dilution series of titers of anti-P33 peptide in salmon serum post-immunization with 50 µg P33/0.1 ml water in oil formulation.

| IDENTIFIED PEPTIDE SEQUENCE NUMBER | PUTATIVE FUNCTION/HOMOLOGOUS SEQUENCES | SEQ ID NO. |
|---|---|---|
| P9 | Uniprot A0A0K2SYS7 Putative peptide sequence of aminopeptidase-like peptide from *L. salmonis*. | 1 |
| | Nucleotide sequence encoding P9 peptide | 2 |
| P13 | NCBI ACO12150 Peptide sequence of putative RAS-LIKE GTP binding protein Rho1 of *L. salmonis* | 3 |
| | Nucleotide sequence encoding P13 peptide | 4 |
| P15 | Uncharacterized peptide sequence | 5 |
| | Nucleotide sequence encoding P15 peptide | 6 |
| P18 | Uncharacterized peptide sequence | 7 |
| | Nucleotide sequence encoding P18 peptide | 8 |
| P21 | Uniprot A0A0K2VDM5- uncharacterized peptide from *L. salmonis* | 9 |
| | Nucleotide sequence encoding P21 peptide | 10 |
| P26 | UNIPROT A0A0K2T5B3 Putative disintegrin and metalloproteinase domain containing protein from *L. salmonis* | 11 |
| | Nucleotide sequence encoding P26 peptide | 12 |
| P33 | Uniprot A0A0K2TQ92: uncharacterized peptide from *L. salmonis* | 13 |
| | Nucleotide sequence encoding P33 peptide | 14 |
| P34 | Uniprot A0A0K2T1P1 Putative Facilitated trehalose transporter from *L. Salmonis* | 15 |
| | Nucleotide sequence encoding P34 peptide | 16 |
| P37 | Uniprot A0A0K2UYH4 Putative bifunctional heparan sulfate N-deacetylase/N-sulfotransferase peptide from *L. salmonis* | 17 |
| | Nucleotide sequence encoding P37 peptide | 18 |

| IDENTIFIED PEPTIDE SEQUENCE NUMBER | PUTATIVE FUNCTION/HOMOLOGOUS SEQUENCES | SEQ ID NO. |
|---|---|---|
| P30 | Uniprot A0A0K2T2M9 Putative peptide Tolllike receptor 6 from *L. salmonis* | 19 |
| | Nucleotide sequence encodinq P30 peptide | 20 |

Additional Sea Louse Identified Peptide and Nucleic Acid Sequence

| IDENTIFIED PEPTIDE SEQUENCE NUMBER | SEQ ID NO. |
|---|---|
| P4 peptide | 21 |
| nucleotide | 22 |
| P5 peptide | 23 |
| nucleotide | 24 |
| P12 peptide | 25 |
| nucleotide | 26 |
| P14 peptide | 27 |
| nucleotide | 28 |
| P16 peptide | 29 |
| nucleotide | 30 |
| P17 peptide | 31 |
| nucleotide | 32 |
| P39 peptide | 33 |
| nucleotide | 34 |

DETAILED DESCRIPTION OF THE INVENTION

Commercial salmon farming in the ocean was first developed in the 1960s, building on the success of early pioneering enhancement projects to raise salmon in hatcheries to repopulate declining wild stocks. The transition from enhancement aquaculture to commercial aquaculture was realized in the 1960s with coho salmon in the Pacific Northwest and with Atlantic salmon in Norway. By 2012 global production of farmed Atlantic salmon exceeded two million metric tons, representing sixty six percent of all salmon species used for human consumption (wild and farmed). Atlantic salmon (*Salmo salar*) is now farmed in twelve countries around the world, with Norway, Chile and Scotland being the top three producers and accounting for eighty seven percent of the total farmed Atlantic salmon production. Norway, by far the world's largest producer, currently accounts for sixty percent of the world's total at 1.2 million metric tons. (International Animal Health Journal Volume 2 Issue 1).

Not long after the farmers in Norway and Scotland began to scale up production, sea lice emerged as a new clinically important pathogen. Problems with sea lice subsequently developed in other farming regions, notably Ireland, Canada and Chile, due to the ubiquitous nature of sea lice as parasites of wild salmon and other marine fish. Sea lice include *Leophtheirus salmonis* (the "salmon louse"), in the Northern Hemisphere and several species of *Caligus* (found in Northern and Southern Hemispheres), the most notable of which is *Caligus rogercressyi* in Chile. Left untreated, sea lice numbers can quickly escalate on farmed salmon, resulting in significant losses. More insidious, perhaps, are the effects sea lice have on growth performance and predisposition of fish to infection from other pathogens (such as bacteria or virus), all of which amount to a significant fish welfare issues if left unchecked.

The salmon louse, *Lepeophtheirus salmonis*, is a marine ectoparasitic copepod feeding on skin, mucus and blood of salmonidae hosts. Salmonidae is a family of ray-finned fish; the only living family currently placed in the order Salmoniformes which includes salmon, trout and chars. Sea lice are obligate ectoparasitic copepods found living on the external surface of salmon. The louse has eight developmental stages and lasts 7-8 weeks at 10° C. (Hamre L A, Eichner C, Caipang C M, Dalvin S T, Bron J E, Nilsen F, Boxshall G, Skern-Mauritzen R. PLoS One. 2013 Sep. 12; 8(9):e73539). Two of the stages are free living in the water, one is infectious and seven are parasites (reviewed in Pike, A. W. and Wadsworth, S. L., Adv. Parasitol. 44: 233-337 (1999)). Naupilus and copepodid are free swimming and non-parasitic stages, and chalimus, pre adult and adult lice are attached and parasitic stages. Lice are at copepodid stage 3 days post infection (dpi), chalimus 7-14 dpi and pre adult 21 dpi. The life cycle of *C. elongatus* lasts 6 weeks, and has no pre adult stage.

Different types of salmonids exhibit varying degrees of susceptibility to sea lice infection. The differences in susceptibility may reflect physiological differences between the different types of salmonids, ex. differences in mucous enzymes prior to infection. Additional differences in mucous enzyme composition also exist among salmonids following lice infection, including levels of serine protease (trypsin-like, 17-22 kDa), alkaline phosphatase, and lysozyme. Besides mucous composition, salmonids show significant differences in immunological parameters in infected fish including respiratory burst, phagocytic activity, and antibody responses Sea lice have also been suggested to be linked to declines in wild salmonids. As a result, the management of sea lice on salmon farms must also take into consideration the effects on, and protection of, wild salmonids. This has led to legislation in most regions requiring routine auditing of lice and development of "trigger" levels, maximum numbers of lice allowed before actions must be taken to bring lice numbers down.

Initially, the first line of defense against sea lice was through the use of veterinary medicines. Pesticides were used to control the sea lice problem in Atlantic salmon farming; however, many of the commercially available treatments have significant drawbacks. Commercially available treatments include (1) Pyrethroids, Alphamax® and Excis® (deltamethrin and cypermethrin, blocks action of sodium channels in axon membranes), (2) Salmosan® (azamethiphos, inhibits acetylcholinesterase and signal transduction in nervous system), (3) Salartect® (hydrogen peroxide, toxicity not well understood, possibly causes mechanical paralysis due to liberation of oxygen in gut and haemolymph), (4) Slice® (emamectin benzoate, inhibits neurotransmission by interfering with GABA receptor in the peripheral nervous system) and (5) Calicide® (tefluben-zuron, chitin synthase inhibitor) (Y E Shahein Vet. Immunol. and Immunopathol. 2008, 121: 281-289, Denholm, I Pest Manag Sci 2002, 58: 528-536, Bravo, S. et al. Aquaculture 2008, 282: 7-12, Lees et al. J. Fish Dis. 2008, 31: 947-951). The limited number of products lead to risk of the development of resistant pathogens that may be very difficult to counter. Thus, there exists a need for novel vaccines against sea lice.

Efforts to develop a sea lice vaccine have historically proven to be a difficult task. Compared to bacteria and viruses, ectoparasitic copepods are structurally and immunologically complex, with very large genomes. It is clear that a more targeted approach is needed to identify critical antigens if the development of a vaccine will be successful.

Therefore, the development of vaccines against sea lice is highly desirable. Up till now, however, no such vaccines are on the market. The search for suitable vaccine candidates has been going on for many years. Identification of novel, protective antigens is the limiting step in increasing the effectiveness of any potential vaccine to be used to prevent sea lice infestation. As stated, sea lice feed on mucus, skin and blood of the host and therefore have only limited contact with the host immune system (Boxaspen, K. ICES Journal of Marine Science 2006, 63: 1304-1316) and due to poor knowledge of the mechanisms and pathology of the salmon infestation by sea lice, target identification for prevention and treatment of this infection have not been successful. This approach has, however, so far not led to vaccines for combating sea lice infection. It is an objective of the present invention to provide a novel vaccine that is capable of inducing a protective immune response in susceptible fish such as *Salmo salar*, and provides a degree of protection against sea lice infection and to the effects of the infection.

General Methodologies:

It should be understood that this invention is not limited to the particular methodology, protocols, and reagents, etc. described herein and as such may vary. The terminology used herein is for the purpose of describing particular embodiments only, and is not intended to limit the scope of the present invention. Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art.

Standard techniques are used for recombinant DNA, oligonucleotide synthesis, and tissue culture and transfection (e.g., electroporation, lipofection). Enzymatic reactions and purification techniques are performed according to manufacturers specifications or as commonly accomplished in the art or as described herein. The foregoing techniques and procedures are generally performed according to conventional methods well known in the art and as described, but not limited to the various general and more specific references that are cited and discussed throughout the present specification, See ex. Sambrook et al. MOLECULAR CLONING: LAB. MANUAL ($3^{rd}$ ed., Cold Spring Harbor Lab. Press, Cold Spring Harbor, N.Y., 2001) and Ausubel et al. Current Protocols in Molecular Biology (New York: Greene Publishing Association JWiley Interscience), Oligonucleotide Synthesis (M. J. Gait, ed.,1984); *Methods in Molecular Biology*, Humana Press; *Cell Biology: A Laboratory Notebook* (J. E. Cellis, ed., 1998) Academic Press; *Animal Cell Culture* (R. 1. Freshney, ed. 1987); *Introduction to Cell and Tissue Culture* (1. P. Mather and P. E. Roberts, 1998) Plenum Press; *Cell and Tissue Culture: Laboratory Procedures* (A. Doyle, J. B. Griffiths, and D. G. Newell, eds., 1993-1998) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Proto-* cols in Immunology (E. Coligan et al., eds., 1991); *Short Protocols in Molecular Biology* (Wiley and Sons, 1999); *Immunobiology* (C. A. Janeway and P. Travers, 1997); Antibodies (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); The Antibodies (M. Zanetti and J. D. Capra, eds., Harwood Academic Publishers, 1995); and *Cancer: Principles and Practice of Oncology* (Y. T. DeVita et al., eds., J. B. Lippincott Company, 1993).

Other than in the operating examples, or where otherwise indicated, all numbers expressing quantities of ingredients or reaction conditions used herein should be understood as modified in all instances by the term "about".

All patents and other publications identified are expressly incorporated herein by reference for the purpose of describing and disclosing, for example, the methodologies described in such publications that might be used in connection with the present invention. These publications are provided solely for their disclosure prior to the filing date of the present application.

Definitions

Before describing the present invention in detail, several terms used in the context of the present invention will be defined. In addition to these terms, others are defined elsewhere in the specification as necessary. Unless otherwise expressly defined herein, terms of art used in this specification will have their art-recognized meanings.

It is noted that in this disclosure, terms such as "comprises", "comprised", "comprising", "contains", "containing" and the like can have the meaning attributed to them in U.S. and international patent law; ex., they can mean "includes", "included", "including" and the like. Terms such as "consisting essentially of" and "consists essentially of" have the meaning attributed to them in U.S. and international patent law, ex., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, ex., novel, nonobvious, inventive, over the prior art, ex., over documents cited herein or incorporated by reference herein. And, the terms "consists of" and "consisting of" have the meaning ascribed to them in U.S. and international patent law; namely, that these terms are closed ended.

The term "antigen", as used herein, refers to a composition, compound, or immunogenic substance that can stimulate the production of antibodies or a T-cell response, or both, in an animal, including compositions that are injected or absorbed into an animal. The immune response may be generated to the whole molecule, or to a portion of the molecule (e.g., an epitope or hapten). The term may be used to refer to an individual macromolecule or to a homogeneous or heterogeneous population of antigenic macromolecules. An antigen reacts with the products of specific immune system of the animal. The term "antigen" broadly encompasses moieties including proteins, polypeptides, antigenic protein fragments, nucleic acids, oligosaccharides, polysaccharides, organic or inorganic chemicals or compositions, and the like. The term "antigen" includes all related antigenic epitopes. Epitopes of a given antigen can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N. J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Furthermore, for purposes of the present invention, an "antigen" can also be used to refer to a protein that includes modifications, such as deletions, additions and substitutions (generally conservative in nature, but they may be non-conservative), to the native sequence, as long as the protein maintains the ability to elicit an immunological response. These modifications may be deliberate, as through site-directed mutagenesis, or through particular synthetic procedures, or through a genetic engineering approach, or may be accidental, such as through mutations of hosts, which produce the antigens. Furthermore, the antigen can be derived or obtained from any parasite, virus, bacterium, protozoan, or fungus, and can be a whole organism or part of organism and can be purified or isolated. Similarly, an oligonucleotide or polynucleotide, which expresses an antigen, such as in nucleic acid immunization applications, is also included in the definition. Synthetic antigens are also included, for example, polyepitopes, flanking epitopes, and other recombinant or synthetically derived antigens (Bergmann et al. (1993) Eur. J. Immunol. 23:2777 2781; Bergmann et al. (1996) J. Immunol. 157:3242 3249; Suhrbier, A. (1997) Immunol. and Cell Biol. 75:402 408; Gardner et al. (1998) 12th World AIDS Conference, Geneva, Switzerland, Jun. 28 Jul. 3, 1998).

The term "heterologous" refers to a combination of elements that are not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature The term "host cell" means any cell of any organism that is selected, modified, transformed, grown, or used or manipulated in any way, for the production of a substance by the cell, for example the expression by the cell of a gene, a DNA or RNA sequence, a protein or an enzyme. A host cell is intended to include any individual cell or cell culture which can be or has been a recipient for vectors or for the incorporation of exogenous nucleic acid molecules, polynucleotides, and/or proteins. It also is intended to include progeny of a single cell. The progeny may not necessarily be completely identical (in morphology or in genomic or total DNA complement) to the original parent cell due to natural, accidental, or deliberate mutation. The cells may be prokaryotic or eukaryotic.

The term "immunogenic composition", as used herein, refers to a composition containing an antigen with or without an immunostimulatory agent such as an adjuvant or molecule used to increase the immune response to the antigen. An immunogenic composition would be understood by one of skill in the art, to be a composition whereby upon administration would elicit an immune response within an animal.

The term "immunogenic fragment" is understood to be a fragment of a full-length protein that still has retained its capability to induce an immune response in a vertebrate host, i.e. comprises an antigenic epitope. In short, an immunogenic fragment is a fragment that is capable of inducing antibodies that react with the full length protein.

"Immune System", as used herein, is defined particularly regarding the fish immune system, possessing the elements of both innate and adaptive immunity. As in other vertebrates, the innate immune system of fish provides the first line of immune defense. Adaptive immunity relies on the generation of random and highly diverse repertoires of T and B-lymphocyte receptors encoded by recombinant activation genes (RAGs) and contributes to a more specific and efficient response against infections.

As used herein, the term "isolated" means that the referenced material is removed from the environment in which it is normally found. Thus, an isolated biological material can be free of cellular components, i.e., components of the cells in which the material is found or produced. In the case of an isolated peptide or protein it may be associated with other proteins or nucleic acids, or both, with which it associates in the cell or with cellular membranes if it is a membrane-associated protein. An isolated organelle, cell, or tissue is removed from the anatomical site in which it is found in an organism. An isolated material may be, but need not be, purified.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

The terms "nucleic acid", "polynucleotide", "nucleic acid molecule" and the like may be used interchangeably herein and refer to a series of nucleotide bases (also called "nucleotides") in DNA and RNA. The nucleic acid may contain deoxyribonucleotides, ribonucleotides, and/or their analogs. The term "nucleic acid" includes, for example, single-stranded and double-stranded molecules. A nucleic acid can be, for example, a gene or gene fragment, exons, introns, a DNA molecule (e.g., cDNA), an RNA molecule (e.g., mRNA), recombinant nucleic acids, plasmids, and other vectors, primers and probes. Both 5' to 3' (sense) and 3' to 5' (antisense) polynucleotides are included. The nucleotides can be deoxyribonucleotides, ribonucleotides, modified nucleotides or bases, and/or their analogs, or any substrate that can be incorporated into a polymer by DNA or RNA polymerase. A poly-nucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, poly-L-Lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-0-methyl-, 2'-0-allyl, 2'-fluoro- or 2'-azido-ribose, carbocyclic sugar analogs, anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (-0-) linkage, aryl, alkenyl, cycloalkyl, cycloalkenyl or araldyl. Not all linkages in a polynucleotide need be identical. The preceding description applies to all polynucleotides referred to herein, including RNA and DNA.

"Operably linked" refers to an arrangement of elements wherein the components so described are configured so as to perform their usual function. Thus, a given promoter that is operably linked to a coding sequence (e.g., a sequence encoding an antigen or interest) is capable of effecting the expression of the coding sequence when the regulatory proteins and proper enzymes are present. In some instances, certain control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence. Thus, a coding sequence is "operably linked" to a transcriptional and translational control sequence in a cell when RNA polymerase transcribes the coding sequence into mRNA, which is then trans-RNA spliced and translated into the protein encoded by the coding sequence The polynucleotides herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, un-natural amino acids, etc.), as well as other modifications known in the art. It is understood that, because the polypeptides of this invention are based upon an antibody, the polypeptides can occur as single chains or associated chains.

The term 'conservative amino acid substitution" indicates any amino acid substitution for a given amino acid residue, where the substitute residue is so chemically similar to that of the given residue that no substantial decrease in polypeptide function (e.g., enzymatic activity) results. Conservative amino acid substitutions are commonly known in the art and examples thereof are described, e.g., in U.S. Pat. Nos. 6,790,639, 6,774,107, 6,194,167, or 5,350,576. In a preferred embodiment, a conservative amino acid substitution will be anyone that occurs within one of the following six groups:
1. Small aliphatic, substantially non-polar residues: Ala, Gly, Pro, Ser, and Thr;
2. Large aliphatic, non-polar residues: Ile, Leu, Val and Met;
3. Polar, negatively charged residues and their amides: Asp and Glu;
4. Amides of polar, negatively charged residues: Asn and Gln;
5. Polar, positively charged residues: Arg and Lys; His; and
6. Large aromatic residues: Trp, Tyr and Phe.

In a preferred embodiment, a conservative amino acid substitution will be any one of the following, which are listed as Native Residue (Conservative Substitutions) pairs: Ala (Ser); Arg (Lys); Asn (Gin; His); Asp (Glu); Gin (Asn); Glu (Asp); Gly (Pro); His (Asn; Gln); lie (Leu; Val); Leu (Ile; Val); Lys (Arg; Gin; Glu); Met (Leu; Iie); Phe (Met; Leu; Tyr); Ser (Thr); Thr (Ser); Trp (Tyr); Tyr (Trp; Phe); and Val (Ile; Leu).

The term "one or more additional sea louse peptide", as used herein, refers to the present vaccine further comprising one or more different recombinant sea louse proteins identified from louse gut, as described herein, used as part of the formulation of the vaccine in addition to the first sea louse. The first sea louse protein is selected from SEQ ID NO.1, SEQ ID NO.5, SEQ ID NO.7, SEQ ID NO.9, SEQ ID NO.13, SEQ ID NO.15 SEQ ID NO.17, SEQ ID NO.19, SEQ ID NO.21, SEQ ID NO. 23, SEQ ID NO. 25, SEQ ID NO. 27, SEQ ID NO.29, SEQ ID NO. 33 and variants or immunogenic fragments thereof. The second sea louse protein is a different peptide than the first sea louse protein but is also selected from SEQ ID NO.1, SEQ ID NO.5, SEQ ID NO.7, SEQ ID NO.9, SEQ ID NO.13, SEQ ID NO.15 SEQ ID NO.17, SEQ ID NO.19 SEQ ID NO.21, SEQ ID NO. 23, SEQ ID NO. 25, SEQ ID NO. 27, SEQ ID NO.29, SEQ ID NO. 33 and variants or immunogenic fragments thereof.

The term "percent identical" or "percent sequence identity" refers to sequence identity between two amino acid sequences or between two nucleotide sequences. The comparison of sequences and determination of percent identity between two sequences can be accomplished using a mathematical algorithm. A non-limiting example of a mathematical algorithm utilized for comparison of sequences is the algorithm of Karlin S and Altschul S F, Proc. Natl. Acad. Sci. USA 87:2264-68 (1990), modified as in Karlin S and Altschul S F, Proc. Natl. Acad. Sci. USA 90:5873-77 (1993). Such an algorithm is incorporated into the NBLAST and XBLAST programs (version 2.0) of Altschul S F et al., J. Mol. Biol. 215:403-10 (1990). BLAST nucleotide searches can be performed with the NBLAST program score=100, word length=12 to obtain homologous nucleotide sequences. BLAST protein searches can be performed with the XBLAST program, score=50, word length=3 to obtain amino acid sequences homologous to the protein molecules of the invention. To obtain gapped alignments for comparison purposes, Gapped BLAST can be utilized as described in Altschul S F et al., Nucleic Acids Res. 25:3389-3402 (1997). When utilizing BLAST and Gapped BLAST programs, the default parameters of the respective programs (e.g., XBLAST and NBLAST) can be used. Another preferred non-limiting algorithm utilized for the comparison of sequences is the algorithm of Myers E W and Miller W, Comput. Appl. Biosci. 4:11-17 (1988). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. In one embodiment, the percent identity of two sequences can be determined by the GCG program with a gap weight of 1, e.g., each amino acid gap is weighted as if it were a single amino acid or nucleotide mismatch between the two sequences.

The terms "vaccine" or "vaccine composition", which are herein used interchangeably, refer to pharmaceutical compositions comprising at least one immunogenic composition that induces an immune response in an animal. A vaccine or vaccine composition may protect the animal from disease or possible death and may or may not include one or more additional components that enhance the immunological activity of the active component. A vaccine or vaccine composition may additionally comprise further components typical to vaccines or vaccine compositions, including, for example, an adjuvant or an immunomodulator. The immunogenically active components of a vaccine may comprise subunit vaccines comprising one or more immunogenic components of an antigen, or genetically engineered, mutated or cloned vaccines prepared by methods known to those skilled in the art or further comprise complete live organisms in either their original form, or as attenuated organisms in a modified live vaccine, or organisms inactivated by appropriate methods in a killed or inactivated vaccine. A vaccine may comprise one or simultaneously more than one of the elements described above. In the present invention, the vaccine composition includes, but is not limited to one or more peptides originally identified in sea louse gut proteins as described herein, described in this patent wherein the one or more isolated peptide has at least about 80% sequence identity with a peptide that is selected from the group consisting of: SEQ ID NO.1, SEQ ID NO.5, SEQ ID NO.7, SEQ ID NO.9, SEQ ID NO.13, SEQ ID NO.15 SEQ ID NO.17, SEQ ID NO.19, SEQ ID NO.21, SEQ ID NO. 23, SEQ ID NO. 25, SEQ ID NO. 27, SEQ ID NO.29, SEQ ID NO. 33 and variants or immunogenic fragments thereof.

There has been an increasing demand for subunit vaccine comprising peptide antigens, such as the vaccine of the present invention. Subunit vaccines can be well tolerated however the limitation of subunit vaccines is that they are, in general, poorly immunogenic and often require the addition of an adjuvant to achieve protective immune responses. The term vaccine adjuvant has been used to define several compounds that enhance the immunogenicity of a co-administered antigen in vivo. As a consequence of this functional definition, the vaccine adjuvants group is composed of diverse classes of molecules such as microbial products, emulsions, mineral salts, small molecules, microparticles and liposomes that have different mechanisms of action. In general, adjuvants are believed to boost a vaccine response by increasing the persistency of the antigen in vivo and/or by targeting innate immune pathways normally associated with response to infection. The recombinant vaccine composition according to the invention comprising recombinant proteins or fragments thereof as outlined above may further comprise an adjuvant. Examples of adjuvants frequently used in fish and shellfish farming are muramyldipeptides, lipopolysaccharides, several glucans and glycans, animal oil, plant oil, mineral oil, Montanide™ and Carbopol®. An extensive overview of adjuvants suitable for fish and shellfish vaccines is given in the review paper by Jan Raa, 1996, Reviews in Fisheries Science 4(3): 229-228.

The vaccine of the invention may further comprise a suitable pharmaceutical carrier. The term "pharmaceutically acceptable carrier" is intended to include any and all solvents, dispersion media, coatings, antibacterial and antifungal agents, isotonic and absorption delaying agents, to hosts. The term "carrier" refers to a diluent, adjuvant, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like. The composition can be formulated with traditional binders and carriers such as triglycerides depending on the method of administration. Particular formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. The formulation should suit the mode of administration.

The appropriate carrier is evident to those skilled in the art and will depend in large part upon the route of administration. Additional components that may be present in this invention are adjuvants, preservatives, surface active agents, chemical stabilizers, suspending or dispersing agents. Typically, stabilizers, adjuvants and preservatives are optimized to determine the best formulation for efficacy in the target subject In a currently preferred embodiment the vaccine is formulated as an emulsion of water in oil. The vaccine may also comprise a "vehicle". A vehicle is a device to which the antigen adheres, without being covalently bound to it. Such vehicles are biodegradable nano/micro-particles or -capsules of PLGA (poly-lactide-co-glycolic acid), alginate or chitosan, liposomes, niosomes, micelles, multiple emulsions and macrosols, all known in the art. A special form of such a vehicle, in which the antigen is partially embedded in the vehicle, is the so-called ISCOM (European patents EP 109.942, EP 180.564 and EP 242.380

In addition, the vaccine may comprise one or more suitable surface-active compounds or emulsifiers, e.g. Cremophore®, Tween® and Span®. Also adjuvants such as interleukin, CpG and glycoproteins may be used.

It is to be understood that the vaccine may further be in a formulation comprising an antigen from a bacterial source, an antigenic material obtained from a viral source, an antigenic material obtained from an additional parasitical source, and/or an antigenic material obtained from a fungal source. Polyvalent vaccines containing antigens from typical fish pathogens other than identified from the gut of sea lice are well known in the art and are already commercially available. In addition, representative isolates of relevant fish pathogens are available from various sources.

In particular embodiments of the invention said antigen from a bacterial source is selected from the group consisting of: live, attenuated or killed bacteria of the species *Piscirickettsias* sp. *Aeromonas* sp., *Vibrio* sp., *Listonella* sp., *Moritella viscosa, Photobacterium damsela, Flavobacterium* sp., *Yersinia* sp., *Renibacterium* sp., *Streptococcus* sp., *Lactococcus* sp., *Leuconostoc* sp., *Bifidobacterium* sp., *Pediococcus* sp., *Brevibacterium* sp., *Edwarsiella* sp., *Francisella* sp., *Pseudomonas* sp., *Cytophaga* sp., *Nocardia* sp., *Mycobacerium* sp., parts or subunits of these bacteria, and any combination hereof.

Isolates of such bacteria are available, e.g. from LGC Promochem/American Type Culture Collection ATCC repository and distribution center (ATCC) including strains of *A. salmonicida* (ATCC 33658), *V. salmonicida* (ATCC 43839), *V. anguillarum* serotype O1(ATCC 43305) and O2(ATCC 19264), and *Moritella viscosa* (ATCC BAA-105). In addition, cultures of *Piscirickettsias salmonis* have been deposited in the European Collection of Cell Culture (ECACC), Health Protection Agency, Porton Down, Salisbury, Wiltshire (UK), SP4 0JG UK on the 9 Jun. 2006 under the following accession numbers: 06050901, 06050902, 06050903 and 07032110.

Other specific embodiments pertain to a vaccine, wherein said antigenic material obtained from a viral source other than the fish virus as defined above is from a virus selected from the group consisting of: Viral Hemorrhagic Septicemia Virus (VHSV), Infectious Hematopoietic Necrosis virus (IHNV), Infectious Pancreatic Necrosis Virus (IPNV), Spring Viremia of Carp (SVC), Channel Catfish Virus (CCV), Infectious Salmon Anaemia virus (ISAV), pancreatic disease virus (SPDV), Iridovirus, Piscine myocarditis virus (PMCV) and heart and skeletal muscle inflammation virus (HSMIV), parts or subunits of any one of these viruses, and combinations thereof. Representative species of such viruses are available to the skilled artisan, for instance from the following deposits: infectious pancreatic necrosis virus (IPNV, ATCC VR-1318, country of origin: unknown), Viral Hemorrhagic Septicemia Virus (VHSV, ATCC VR_1389, country of origin: Denmark); Infectious Hematopoietic Necrosis virus (IHNV, ATCC VR-1392, country of origin: USA)); Pancreatic Necrosis Virus; Spring Viremia of Carp (SVC, ATCC VR-1390, country of origin: Denmark); Channel Catfish Virus (CCV) (ATCC VR-665, country of origin: USA); Infectious Salmon Anaemia (ISA) virus (ATCC VR-1554, country of origin: Canada). Patent deposits have previously been made by the present applicant of the following viral species: Heart and Skeletal Muscle Infection Virus (HSMIV, patent deposit nr ECACC 04050401, country of origin: Norway).

In more specific embodiments, said antigenic material obtained from a viral source other than the fish virus as defined above is from the group consisting of: Glycoprotein of Viral Hemorrhagic Septicemia Virus (VHSV), nucleoprotein of Viral Hemorrhagic Septicemia Virus (VHSV), glycoprotein of Infectious Hematopoietic Necrosis virus (IHNV), nucleoprotein structural proteins of Infectious Pancreatic Necrosis Virus (IPNV), G protein of Spring Viremia of Carp (SVC), and a membrane-associated protein, tegumin or capsid protein or glycoprotein, of Channel Catfish Virus (CCV), antigenic fragments of any of one of these proteins and combinations hereof.

In other embodiments said antigenic material from an additional parasitic source is from a source selected from the *Lepeophtheirus* Sp., *Caligus* Sp., and *Ichthyophthirius* Sp, parts of any one of these parasites, and combinations thereof. In yet other embodiments said antigenic material is from a fungal source selected from the group consisting of *Saprolegnia* Sp., *Branchiomyces sanguinis, Branchiomyces demigrans* and *Icthyophonus hoferi.*

The vaccine according to the invention may in particular be formulated for administration to a fin fish. More specifically the vaccine may be (formulated) for administration to a telostei. The teleostei include, but are not limited to salmonids, basses, breams, cods, snappers, flatfish, catfish, yellowtails and tilapias.

In a presently preferred embodiment the vaccine is formulated for administration to Atlantic salmon (*Salmo salar*), Brown trout (*Salmo trutta*), Rainbow trout (*Oncorhynchus mykiss*), Coho salmon (*Oncorhychus kisutch*), Sockeye salmon (*Oncorhynchus nerka*), Chinook salmon (*Oncorhynchus tshawytscha*), Pink salmon (*Oncorhynchus gorbuscha*), Chum salmon (*Oncorhynchus keta*) and the Masu salmon (*Oncorhynchus masu*).

In further embodiments of the invention the vaccine is formulated for administration by one or more routes selected from the group consisting of: Bath, immersion, intraperitoneal injection, intramuscular injection and oral administration.

A "variant" peptide refers herein to a peptide which differs in amino acid sequence from a "parent" vaccine peptide amino acid sequence by virtue of addition, deletion, and/or substitution of one or more amino acid residue(s) in the parent peptide sequence and retains at least one desired activity of the parent vaccine peptide. For example, the variant may comprise at least one, ex. from about one to about ten, and preferably from about two to about five, substitutions in one or more amino acid sequences of the peptide to be used as part of the vaccine of the present invention. Ordinarily, the variant will have an amino acid sequence having at least 50% amino acid sequence identity with the parent amino acid sequences, preferably at least 65%, more preferably at least 70%, more preferably at least 75%, more preferably at least 80%, more preferably at least 85%, more preferably at least 90%, and most preferably at least 95% sequence identity. Identity or homology with respect to this sequence is defined herein as the percentage of amino acid residues in the candidate sequence that are identical with the parent peptide residues, after aligning the sequences and introducing gaps, if necessary, to achieve the maximum percent sequence identity. None of N-terminal, C-terminal, or internal extensions, deletions, or insertions into the peptide sequence shall be construed as affecting sequence identity or homology. The variant retains the ability to elicit an immune response and preferably has desired activities which are superior to those of the parent peptide.

Variant peptides may be fully functional or may lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis. Cunningham et al., 244 Science 1081-85 (1989). The latter procedure introduces single alanine mutations at every residue in the molecule. The resulting mutant molecules are then tested for biological activity such as epitope binding or in vitro ADCC activity. Sites that are critical for ligand-receptor binding can also be determined by structural analysis such as crystallography, nuclear magnetic resonance, or photoaffinity labeling. Smith et al., 224 J. Mol. Biol. 899-904 (1992); de Vos et al., 255 Science 306-12 (1992).

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill in the art and have been described in great detail in the scientific literature. Several particularly common modifications, glycosylation, lipid attachment, sulfation, gamma-carboxylation of glutamic acid residues, hydroxylation and ADP ribosylation, for instance, are described in most basic texts, such as Proteins-Structure and Molecular Properties (2nd ed., T. E. Creighton, W.H. Freeman & Co., NY, 1993). Many detailed reviews are available on this subject, such as by Wold, Posttranslational Covalent Modification of proteins, 1-12 (Johnson, ed., Academic Press, NY, 1983); Seifter et al. 182 Meth. Enzymol. 626-46 (1990); and Rattan et al. 663 Ann. NY Acad. Sci. 48-62 (1992).

Accordingly, the peptides of the present invention also encompass derivatives or analogs in which a substituted amino acid residue is not one encoded by the genetic code. Similarly, the additions and substitutions in the amino acid sequence as well as variations, and modifications just described may be equally applicable to the amino acid sequence of antigen and/or epitope or peptides thereof, and are thus encompassed by the present invention.

A "therapeutically effective amount" or "immunogenically effective amount" refers to an amount of an active ingredient, for example an agent according to the invention, sufficient to effect beneficial or desired results when administered to a subject. An effective amount can be administered in one or more administrations, applications or dosages. A therapeutically effective amount of a composition according to the invention may be readily determined by one of ordinary skill in the art. An effective amount can be administered in one or more administrations. For purposes of this invention, an effective amount of vaccine is an amount sufficient to induce a protective immune response in fish which will prevent or control a sea lice infestation. The therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art.

As used herein, "treatment" is an approach for obtaining beneficial or desired clinical results. For purposes of this invention, beneficial or desired clinical results include, but are not limited to preventing and/or controlling a sea lice infestation in fish.

A "variant" nucleic acid, refers herein to a molecule which differs in sequence from a "parent" nucleic acid. Polynucleotide sequence divergence may result from mutational changes such as deletions, substitutions, or additions of one or more nucleotides. Each of these changes may occur alone or in combination, one or more times in a given sequence.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. Vectors, as described herein, have expression control sequences meaning that a nucleic acid sequence that directs transcription of a nucleic acid. An expression control sequence can be a promoter, such as a constitutive or an inducible promoter, or an enhancer. The expression control sequence is 'operably linked' to the nucleic acid sequence to be transcribed. A nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Just as a polypeptide may contain conservative amino acid substitution(s), a polynucleotide thereof may contain conservative codon substitution(s). A codon substitution is considered conservative if, when expressed, it produces a conservative amino acid substitution, as described above. Degenerate codon substitution, which results in no amino acid substitution, is also useful in polynucleotides according to the present invention. Thus, for example, a polynucleotide encoding a selected polypeptide useful in an embodiment of the present invention may be mutated by degenerate codon substitution in order to approximate the codon usage frequency exhibited by an expression host cell to be transformed therewith, or to otherwise improve the expression thereof.

Vaccine

A first aspect of the present invention pertains to a vaccine composition for control or prevention of an infestation of sea lice comprising an immunologically or therapeutically effective dose of an isolated sea louse peptide and a pharmaceutically acceptable carrier. In particular, the invention provides for a vaccine comprising a peptide where in the peptide has at least about 80%, 85%, 90% or 95% sequence identity with a peptide that is selected from the group consisting of SEQ ID NO. 1, SEQ ID NO. 5, SEQ ID NO.7, SEQ ID NO.9, SEQ ID NO.13, SEQ ID NO. 15 SEQ ID NO.17, SEQ ID NO. 19, SEQ ID NO.21, SEQ ID NO. 23, SEQ ID NO. 25, SEQ ID NO. 27, SEQ ID NO.29, SEQ ID NO. 33 and variants or immunogenic fragments thereof. Said peptide is a peptide identified from the gut of a sea louse, in particular a salmon louse or *Lepeophtheirus salmonis*. The determination and isolation of the appropriate sea louse gut peptide is described in the examples section below.

The vaccine of the invention is for use is preventing or controlling an infestation of sea lice. In an embodiment of the present invention the vaccine will be used to treat Salmonid. Salmonids are selected from salmon, trout and chars, which are particularly affected by *L. salmonis*. *L. salmonis*, a marine ectoparasitic copepod and obligate parasite, feeds on skin, mucus and blood of and lives on the external surface of the salmon. The increase in salmon farming has increased the dangers of *L. salmonis* infestation in both wild and farmed salmon. If left untreated, sea lice numbers can quickly escalate on farmed salmon in particular, resulting in significant losses.

The vaccine of the invention could be considered by one of skill in the art as a subunit or peptide vaccine. In an embodiment of the present invention the vaccine further comprises an adjuvant used to increase the immune response upon administration of the vaccine composition to a fish. The vaccine adjuvants group is composed of diverse classes of molecules such as microbial products, emulsions, mineral salts, small molecules, microparticles and liposomes that have different mechanisms of action. Examples of adjuvants frequently used in fish and shellfish farming are muramyl-dipeptides, lipopolysaccharides, several glucans and glycans, animal oil, vegetable oil, mineral oil, Montanide® and Carbopol®. An embodiment of the present invention describes a vaccine further comprising an adjuvant selected from muramyl dipeptides, lipopolysaccharides, glucans, glycans, mineral oil-in-water emulsion, Freund's adjuvant and acrylic acid polymers. In a preferred embodiment of the invention the vaccine further comprises a water-in-oil emulsion.

The vaccine of the invention may further comprise a suitable pharmaceutical carrier. The appropriate carrier is evident to those skilled in the art and will depend in large part upon the route of administration. Additional components that may be present in this invention are adjuvants, preservatives, surface active agents, chemical stabilizers, suspending or dispersing agents. Typically, stabilizers, adjuvants and preservatives are optimized to determine the best formulation for efficacy in the target subject The vaccine of the present invention may further comprise a non-sea lice antigen to add additional protection against pathogenic organisms that can infect salmon. The non-sea lice antigen is selected from *Piscirickettsias* sp. *Aeromonas* sp., *Vibrio* sp., *Listonella* sp., *Moritefia viscosa*, *Photobacterium damsela*, *Flavobacterium* sp., *Yersinia* sp., *Renibacterium* sp., *Streptococcus* sp., *Lactococcus* sp., *Leuconostoc* sp., *Bifidobacterium* sp., *Pediococcus* sp., *Brevibacterium* sp., *Edwarsiella* sp., *Francisella* sp., *Pseudomonas* sp., *Cytophaga* sp., *Nocardia* sp., *Mycobacerium* sp., Viral Hemorrhagic Septicemia Virus (VHSV), Infectious Hematopoietic Necrosis virus (IHNV), Infectious Pancreatic Necrosis Virus (IPNV), Spring Viremia of Carp (SVC), Channel Catfish Virus (CCV), Infectious Salmon Anaemia virus (ISAV), pancreatic disease virus (SPDV), Iridovirus, piscine myocarditis virus (PMCV), heart and skeletal muscle inflammation virus (HSMIV), *Saprolegnia* Sp., *Branchiomyces sanguinis*, *Branchiomyces demigrans* and variants and immunogenic fragments thereof.

The vaccine of the present invention may further comprise one or more recombinant peptide(s), as described herein, that were identified from the gut of sea lice, cloned and then expressed. The one or more additional peptide(s) comprises a peptide that is different from the first peptide of the vaccine composition and is selected from peptides that are at least about 80%, 85%, 90% or 90% identical to SEQ ID NO. 1, SEQ ID NO. 5, SEQ ID NO.7, SEQ ID NO.9, SEQ ID NO.13, SEQ ID NO. 15 SEQ ID NO.17, SEQ ID NO. 19, SEQ ID NO.21, SEQ ID NO. 23, SEQ ID NO. 25, SEQ ID NO. 27, SEQ ID NO.29, SEQ ID NO. 33 and variants or immunogenic fragments thereof.

The vaccine of the present invention comprises peptides that are encoded by nucleic acid sequences that are selected from nucleic acids having at least about 80%, 85%, 90% or 95% sequence identity to SEQ ID NO. 2, SEQ ID NO. 6, SEQ ID NO. 8, SEQ ID NO. 10, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 34. The nucleic acids encode peptides of the vaccine and, by way of techniques understood by one of skill in the art, are cloned into vector sequences that enable expression of said nucleic acids in a host cell proceeded by isolation and purification of the peptides utilized as part of the vaccine of the invention.

Method of Administration

One further aspect of the invention provides a method of vaccinating a salmonid susceptible to sea lice infestation which comprises the steps of administering the vaccine composition of the invention. The vaccine composition is described above and the methods are described within the examples section of the present specification. The vaccine of the invention is meant to be administered to fish, particularly salmon. The route of administration is selected from intraperitoneal injection, intramuscular injection, bath, immersion, and oral administration. A preferred embodiment of the present invention comprises the administration route as intraperitoneal injection.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

All patents and other publications identified are expressly incorporated herein by reference for the purpose of describing and disclosing, for example, the methodologies described in such publications that might be used in connection with the present invention. These publications are provided solely for their disclosure prior to the filing date of the present application.

The present invention is further illustrated and supported by the following examples. However, these examples should in no way be considered to further limit the scope of the invention. To the contrary, one having ordinary skill in the art would readily understand that there are other embodiments, modifications, and equivalents of the present invention without departing from the spirit of the present invention and/or the scope of the appended claims.

EXAMPLES

Example 1

Identification of Candidate *Lepeophtheirus salmonis* Antigens

The main objective was to identify candidate antigens for the control of sea lice (*Lepeophtheirus salmonis*) infestations in vaccinated salmon. In particular, overrepresented and overexpressed gut membrane proteins in fed lice, as compared to unfed lice, were considered potentially suitable candidates to be used as protective antigens in vaccines. Additionally, to reduce the number of candidate antigens, gene and protein ontologies were characterized in order to select proteins with low redundancy and important biological functions for louse feeding and development. The rationale behind this approach was to select antigens for which antibodies produced in vaccinated salmon will interact with the protein in feeding lice to affect its biological function and reduce ectoparasite feeding and development.

The gut transcriptome and gut plasma membrane proteomes were obtained in unfed (starved) and fed sea lice using RNAseq and RP-LC-MS/MS, respectively. Total RNA was extracted from unfed and fed sea lice gut samples using Qiazol and the TissueLyzer (Qiagen) following manufacturer's protocol (RNeasy® Lipid Tissue Mini Kit; Qiagen cat. No. 74804). RNeasy® Mini Kit (Qiagen cat. No. 217004) was followed including the DNase in-column treatment. For both samples, more than 7 µg total RNA was obtained and as expected, the unfed: fed RNA ratio was approximately 1:3. The quality of the RNA was checked using the Bio-Analyzer 2100 (Agilent Technologies, Santa Barbara, Calif., USA) and fulfilled criteria for RNAseq. The RNAs were subjected to RNA library prep using the TruSeq RNA sample prep kit v.2 (Illumina) according to the low-throughput procedure.

3 µg of total RNA was used as starting material for library preparation. Messenger RNA was captured using poly-dT magnetic beads and polyA+ RNA was chemically fragmented to a size compatible with Illumina sequencing. Fragmentation time was reduced to 1 min in order to recover fragments of an increased size, which facilitates the assembly of pair-end reads. RNA was then used for cDNA synthesis and remaining RNA was removed, following an end repair procedure and preparation of double-stranded cDNA for adaptor ligation. Adaptor oligonucleotides were ligated to both ends and cDNA samples were washed using AmPure SPRI-based magnetic beads. Adapters included short sequences that allow multiplexing in the sequencing run, in addition to signals for further amplification and sequencing.

PCR enrichment was then performed to amplify the cDNA library, ensuring that all molecules in the library include the desired adapters. Libraries were titrated by quantitative PCR using a reference standard to assign the exact number of molecules. The titration showed that molecular concentration was similar for both unfed lice and fed lice libraries.

The libraries were denatured and sequenced. Sequence reads were trimmed at the error probability higher than 0.05 and read. The remaining pairs of reads were assembled only when the two members of the pair remained after filtering and trimming. The assembled transcripts were also explored using BLASTN against L. salmonis ESTs available at NCBI.

Transcript sequences were clustered by similarity to a set of reference proteins to build Unigenes. Reference proteins were used for transcript clustering to obtain a protein-centered analysis of gene expression that is more useful for functional analysis in a de novo transcriptome. After bioinformatics analysis of transcriptomics and proteomics data nucleic acid and protein sequences were selected. Unigenes encoding putative secreted and membrane proteins and proteins overrepresented with two or more peptides or exclusively represented in fed lice were selected. Gene and protein ontology assignments were considered to select proteins putatively involved in louse feeding and development. The proteins not exposed on the gut membrane or with high redundancy were discarded.

Example 2

Isolation, Cloning and Expression of L. salmonis Peptides

A protocol was developed for the extraction of louse gut plasma membrane proteins. Frozen guts from fed (30 mg) and unfed (20 mg) L. salmonis were homogenized with a glass homogenizer (20 strokes) in STM solution (0.25 M sucrose, 1 mM MgCl2, 10 mM, Tris-HCl, pH 7.4) supplemented with complete mini protease inhibitor cocktail (Roche,Basel, Switzerland) (10 ml/g tissue). Sample was sonicated for 1 min in an ultrasonic cooled bath followed by 10 sec of vortex. After 3 cycles of sonication-vortex, the homogenate was centrifuged at 260×g for 5 min at 4° C. to remove cellular debris. The supernatant was then centrifuged at 13000×g for 30 min at 4° C. and the pellet fraction enriched in crude plasma membranes was collected, resuspended in 150 µl STM solution supplemented with 0.7% DDM and 0.5% ASB14 (detergents), incubated on a shaker 1 h at 4° C. (vortex of 5 sec after 15 min periods) and centrifuged at 13000×g for 30 min at 4° C. The pellet was stored at −80° C. for further processing and the soluble plasma membrane was first precipitated using Chloroform/methanol, dried and also stored at −80° C. until used.

Precipitated plasma membrane soluble and pellet fractions were resuspended in 100 µl Laemmli sample buffer and applied onto 1.2-cm wide wells on a 12% SDS-PAGE gel. The electrophoretic run was stopped as soon as the front entered 3 mm into the resolving gel, so that the whole proteome became concentrated in the stacking/resolving gel interface. The unseparated protein band was visualized by staining with GelCode Blue Stain Reagent (Thermo Scientific), excised, cut into 2×2 mm cubes and digested overnight at 37° C. with 60 ng/µl sequencing grade trypsin (Promega, Madison, Wis., USA) at 5:1 protein:trypsin (w/w) ratio in 50 mM ammonium bicarbonate, pH 8.8 containing 10% (v/v) acetonitrile [Shevchenko et al., 2006]. The resulting tryptic peptides from the gel band were extracted by 30 min-incubation in 12 mM ammonium bicarbonate, pH 8.8.Trifluoroacetic acid was added to a final concentration of 1% and the peptides were finally desalted onto OMIX Pipette tips C18 (Agilent Technologies, Santa Clara, Calif., USA), dried-down and stored at −20° C. until mass spectrometry analysis.

The desalted protein digest was resuspended in 0.1% formic acid and analyzed by RPLC-MS/MS using an Easy-nLC II system coupled to an ion trap LCQ Fleet mass spectrometer (Thermo Scientific). The peptides were concentrated by reverse phase chromatography using a 0.1 mm×20 mm C18 RP precolumn (Thermo Scientific), and separated using a 0.075 mm×100 mm C18 RP column (Thermo Scientific) operating at 0.3 µl/min. Peptides were eluted using a 180-min gradient from 5 to 35% solvent B (Solvent A: 0.1% formic acid in water, solvent B: 0.1% formic acid in acetonitrile). ESI ionization was done using a Fused-silica PicoTip Emitter ID 10 µm (New Objective, Woburn, Mass., USA) interface. Peptides were detected in survey scans from 400 to 1600 amu (1 µscan), followed by three data dependent MS/MS scans (Top 3), using an isolation width of 2 mass-to-charge ratio units, normalized collision energy of 35%, and dynamic exclusion applied during 30 sec periods.

The MS/MS raw files were searched against the Crustacea and Salmoninae Uniprot databases using the SEQUEST algorithm (Proteome Discoverer 1.3; Thermo Scientific. Differential protein representation between different samples for louse proteins was determined using peptides/protein by $\chi 2$-test (p=0.05). A total of 32,738,818 (6,613, 241,236 bp) and 32,380,452 (6,540,851,304 bp) 100 bp pair end pass-filter reads were obtained for fed and unfed lice, respectively. After filtering and trimming, a total of 30,434, 012 and 30,183,992 paired-end reads were de novo assembled obtaining 24,080 and 25,926 transcripts for fed and unfed lice, respectively. These transcripts were annotated and clustered by similarity to Uniprot proteins building a set of 7,428 Unigenes whose differences in expression levels were compared between fed and unfed samples. Of them, 6,697 and 6,712 Unigenes were identified in fed and unfed lice, respectively. After removing Unigenes with identity to the bacteria identified in lice, *F. johnsoniae* and *V. fischeri*, the expression of 716 Unigenes was exclusively detected in fed lice, 731 Unigenes were exclusive to unfed lice and 5,981 Unigenes were expressed in both samples with differential expression (p<0.05) detected in 2,035 of them (927 under expressed and 1,108 overexpressed in fed lice).

For the initial screening of vaccine candidates, the 1,824 Unigenes found exclusively expressed (N=716) and overexpressed (N=1,108) in fed lice were analyzed for putative Unigenes encoding for secreted and membrane proteins. This analysis resulted in the identification of 300 Unigenes.

A total of 388 and 77 unique louse and host salmon proteins were identified in the gut plasma membrane proteome, respectively. Of the 388 louse proteins identified, 181 matched to *L. salmonis* proteins. Of these 388 louse proteins, 67 and 149 were exclusively represented in unfed and fed lice, respectively while 172 were represented in both samples. The number of peptides used for protein identification was higher in fed lice for both louse and salmon proteins, probably reflecting the effect of feeding on proteins represented. Excluding proteins with unknown function (N=96; 25%), louse proteins were annotated into 12 biological processes (BP) and 4 molecular functions (MF). Similar to transcriptomics results, the most represented BPs corresponded to cellular process (31%), metabolic process (23%) and localization (8%) while proteins with binding (43%) and catalytic (33%) activities were the most represented MFs.

For the selection of candidate protective antigens, proteins found exclusively represented (N=149) and overrepresented with two or more peptides (N=70) in fed lice were selected for further analysis.

Further analysis was carried out and it was determined that the candidate antigens exemplified below were to be tested for immunogenicity and protection in Atlantic salmon.

Example 3

After differential expression analysis was performed and peptides were isolated (described above) *L. salmonis* peptides of interest were used to determine immunogenicity and protection against challenge. See Table 1 for description of peptides.

TABLE 1

| IDENTIFIED SEQUNCE NUMBER | PUTATIVE FUNCTION/HOMOLOGOUS SEQUENCES | SEQ ID NO. |
| --- | --- | --- |
| P9 | Uniprot A0A0K2SYS7 Putative peptide sequence of aminopeptidase-like peptide from *L. salmonis*. | 1 |
|  | Nucleotide sequence encoding P9 peptide | 2 |
| P13 | NCBI ACO12150 Peptide sequence of putative RAS-LIKE GTP binding protein Rho1 of *L. salmonis* | 3 |
|  | Nucleotide sequence encoding P13 peptide | 4 |
| P15 | Uncharacterized peptide sequence | 5 |
|  | Nucleotide sequence encoding P15 peptide | 6 |
| P18 | Uncharacterized peptide sequence | 7 |
|  | Nucleotide sequence encoding P18 peptide | 8 |

TABLE 1-continued

| IDENTIFIED SEQUNCE NUMBER | PUTATIVE FUNCTION/HOMOLOGOUS SEQUENCES | SEQ ID NO. |
| --- | --- | --- |
| P21 | Uniprot A0A0K2VDM5- uncharacterized peptide from *L. salmonis* | 9 |
|  | Nucleotide sequence encoding P21 peptide | 10 |
| P26 | UNIPROT A0A0K2T5B3 Putative disintegrin and metalloproteinase domain containing protein from *L. salmonis* | 11 |
|  | Nucleotide sequence encoding P26 peptide | 12 |
| P33 | Uniprot A0A0K2TQ92: Uncharacterized peptide from *L. salmonis*. Homology to human K/Cl cotransporter. | 13 |
|  | Nucleotide sequence encoding P33 peptide | 14 |
| P34 | Uniprot A0A0K2T1P1 Putative Facilitated trehalose transporter from *L. Salmonis* | 15 |
|  | Nucleotide sequence encoding P34 peptide | 16 |
| P37 | Uniprot A0A0K2UYH4 Putative bifunctional heparan sulfate N-deacetylase/N-sulfotransferase peptide from *L. salmonis* | 17 |
|  | Nucleotide sequence encoding P37 peptide | 18 |
| P30 | Uniprot A0A0K2T2M9 Putative peptide Tolllike receptor 6 from *L. salmonis* | 19 |
|  | Nucleotide sequence encoding P30 peptide | 20 |

Production of the proteins of interest (table below) was carried out as followed: the nucleotide sequence coding for each protein was cloned into a standard IPTG inducible expression vector with kanamycin resistance for use in *E. coli*. *E. coli* BL21 (DE3) was transformed with recombinant plasmids. A single colony was inoculated into LB medium containing kanamycin; cultures were incubated at both 15° C. and 37° C. with shaking 200 rpm. Once cell density reached to OD=0.6-0.8 at 600 nm, IPTG was introduced for induction. SDS-PAGE and Western blot were used to monitor the expression. An example of the stained SDS-PAGE gel and subsequent Western blot of the P33 peptide can be seen in FIGS. 11A and 11B demonstrating that the P33 peptide is expressed at both 15° C. and 37° C.

Example 4

Immunogenicity

Recombinant protein was produced as described in Example 3 and formulated into standard water-in-oil formulations. Atlantic salmon 25-30 grams were vaccinated with 50 μg protein in a 0.1 ml vaccine and kept at 12-15° C. in a 500 L tank for 5 weeks and then given a booster injection identical to the initial vaccination. 9 weeks post vaccination; plasma was collected from seven fish and tested in an ELISA assay using standard procedures.

ELISA-plates were coated with 2 mg/ml of protein diluted in NaCl overnight. The plates were washed three times in PBS-Tween, and blocked with 5% dry milk in PBS-Tween for three hours. The plates were washed three times in PBS-Tween, and plasma samples diluted 2-fold from 1/50 to 1/1600 in PBST+1% TM were added. The binding of antibodies to peptides were visualized with a monoclonal antibody against salmon immunoglobulin and a secondary anti-mouse immunoglobulin coupled to alkaline phosphatase. Substrate was added, and the plates read at $OD_{405}$. Readings greater than or equal to two times the control were regarded as a positive response. Results of immunogenicity demonstrated in Table 2. Exemplary results of P33 peptide immunogenicity can be seen in FIG. 12.

TABLE 2

| Protein | Specific antibody response |
|---------|---------------------------|
| P9 | no |
| P13 | no |
| P15 | yes |
| P18 | yes |
| P21 | yes |
| P26 | no |
| P33 | yes |
| P34 | yes |
| P37 | yes |
| P30 | yes |
| Control | No |

Example 5

A total of 36 Atlantic salmon were vaccinated by intraperitoneal injection per peptide group of a 50 µg/ml in a water-in-oil formulation per fish after anesthetizing with Tricain™ (PHARMAQ). The salmon were tagged by shortening of left maxillae. A control group containing 38 Atlantic salmon received a placebo vaccine identical to the test-group, but without antigen. Average weight of the study population was 114 g. The fish were kept together at 12° C. in a 500 L tank for 5 weeks and then given a booster injection identical to the initial vaccination. The vaccinated fish were kept in tanks together with control fish for the duration of the study. The fish were kept in freshwater at 17° C. during the immunization period that lasted 7 weeks. The fish were then transferred to seawater and temperature lowered to 12° C. The fish were challenged by lowering water in the tank to approximately 10-20 cm depth, adding infectious copepods of *Lepeophtheirus salmonis* strain LsGulen, and then gradually increase of water level again. Number of chalimus that developed on each group was counted approximately 2 weeks post challenge. Number of adult lice (both sexes) that developed on each group was counted approximately 5 weeks post challenge as demonstrated in Table 3.

TABLE 3

| Protein | Reduction relative to control group |
|---------|------------------------------------|
| P13 | −18% |
| P15 | 12% |
| P18 | 16% |
| P26 | −24% |
| P33 | 14% |
| P34 | 8% |
| P37 | 31% |
| P30 | 7% |
| Control | N/A |

The specific results as it relates to the sexes of the adult lice were broken down for the P33 group as demonstrated in Table 4.

TABLE 4

| Group | Chalimus | Adult males | Adult females |
|-------|----------|-------------|---------------|
| P33 | 13.64 ± 0.7849 | 4.167 ± 0.3994 | 3.806 ± 0.3376 |
| Control | 15.85 ± 1.122 | 4.950 ± 0.3986 | 5.825 ± 0.5761 |

Vaccination with the vaccine comprising the P33 water-in-oil formulation as described above reduced the number of chalimus by 14%, the number of adult males with 16% and number of adult female lice with 35%.

Example 6

A total of 10 Atlantic salmon were vaccinated with P33 (50 µg/ml) by intraperitoneal injection of 0.1 ml per fish, and tagged by shortening of left maxillae. A control group containing 10 Atlantic salmon received a placebo vaccine identical to the test-group, but without antigen. Average weight of the study population was 114 g. The fish were kept together at 12° C. in a 500 L tank for 5 weeks and then given a booster injection identical to the initial vaccination. Fish were then challenged approximately 10 weeks after the first vaccination by placing 15 (8 males and 7 females) pre-adult *Lepeophtheirus salmonis* directly on the surface of each anesthetized fish. The fish were then moved to 20 solitary tanks (approx. 40 L) where one fish is kept in each tank. A similar system has been described previously by Hamre et al 2013. The proportion of adult lice that developed on each fish was registered approximately 5 weeks post challenge and the length of each eggstring was measured as demonstrated in Table 5

TABLE 5

| Group | Adult survival (proportion) | Eggstring length (mm) |
|-------|---------------------------|----------------------|
| P33 | 0.2612 ± 0.0251 | 8.587 ± 0.8397 |
| Control | 0.3589 ± 0.0585 | 10.38 ± 0.6253 |

Vaccination reduced the development of adult lice from pre-adults by 27% and the length of eggstrings by 17%.

Example 7

Atlantic salmon parr of approximate weight 30 g were anesthetized with Tricain (PHARMAQ) and vaccinated intraperitoneally with 0.1 ml per fish of a water-in-oil formulation of antigens P4 (SEQ ID NO. 21), P5 (SEQ ID NO. 23), P12 (SEQ ID NO. 25), P14 (SEQ ID NO. 27), P16 (SEQ ID NO. 29), P17 (SEQ ID NO. 31), P30 (SEQ ID NO. 19), and P39 (SEQ ID NO. 33) or a commercial vaccine as control (n=15 per group). The groups were kept as mixed populations during the experiment. The groups were tagged during the vaccination process with intradermal injection of colored elastomer for identification of groups. The fish were immunized in freshwater and then transferred to seawater at 12° C. The fish were challenged adding infectious copepodids of *Lepeophtheirus salmonis*. The number of attached lice was counted on each fish two weeks post challenge. At this point, the lice had reached the chalimus stage. In addition, blood samples were taken for quantification of immunoglobulin levels against the respective antigens. The immunoglobulin levels were measured by ELISA, using the following protocol with washing with PBS between each incubation:

50 µL of antigen at a concentration of (1.0 µg/mL) in standard carbonate coating buffer pH 9.6. and incubated overnight at 4° C.;
  200 µL 5% BSA and incubated 1 hr at RT;
  50 µL of Fish plasma/serum in dilution 1:50. Incubate 2 h at RT;
  50 µL 4C10 (mouse anti-salmon IgM) (1:20) and incubate at RT for 1 h;
  100 µL tertiary antibody (sheep anti-mouse IgG1 HRP, GE Healthcare, NA931V) (1:4 000) and incubate at RT for 1 h;
  100 µL Ultra TMB-ELISA (Thermo Scientific), Incubate for 10 min at RT;
  2M H2SO4;
  The optical density were read at 450 nm and the data are presented in FIGS. 1 and 2.

Results

TABLE 6

| | Tank 1 | | | | Tank 2 | | |
| --- | --- | --- | --- | --- | --- | --- | --- |
| Group | Attached chalimus mean | Attached chalimus SD | Reduction relative to control | Group | Attached chalimus mean | Attached chalimus SD | Reduction relative to control |
| Control | 23.45 | 8.42 | 0.00% | Control | 14.54 | 5.01 | 0.00% |
| P16 | 24.53 | 9.71 | 4.6% | P17 | 16.27 | 6.38 | 11.9% |
| P12 | 18.47 | 7.59 | −21.3% | P39 | 14.67 | 4.83 | 0.9% |
| P5 | 17.80 | 7.51 | −24.1% | P30 | 14.04 | 7.40 | −3.4% |
| P4 | 25.25 | 9.57 | 7.7% | P31 | 13.71 | 3.27 | −5.7% |
| P14 | 17.87 | 5.66 | −23.8% | | | | |

Figure 21:
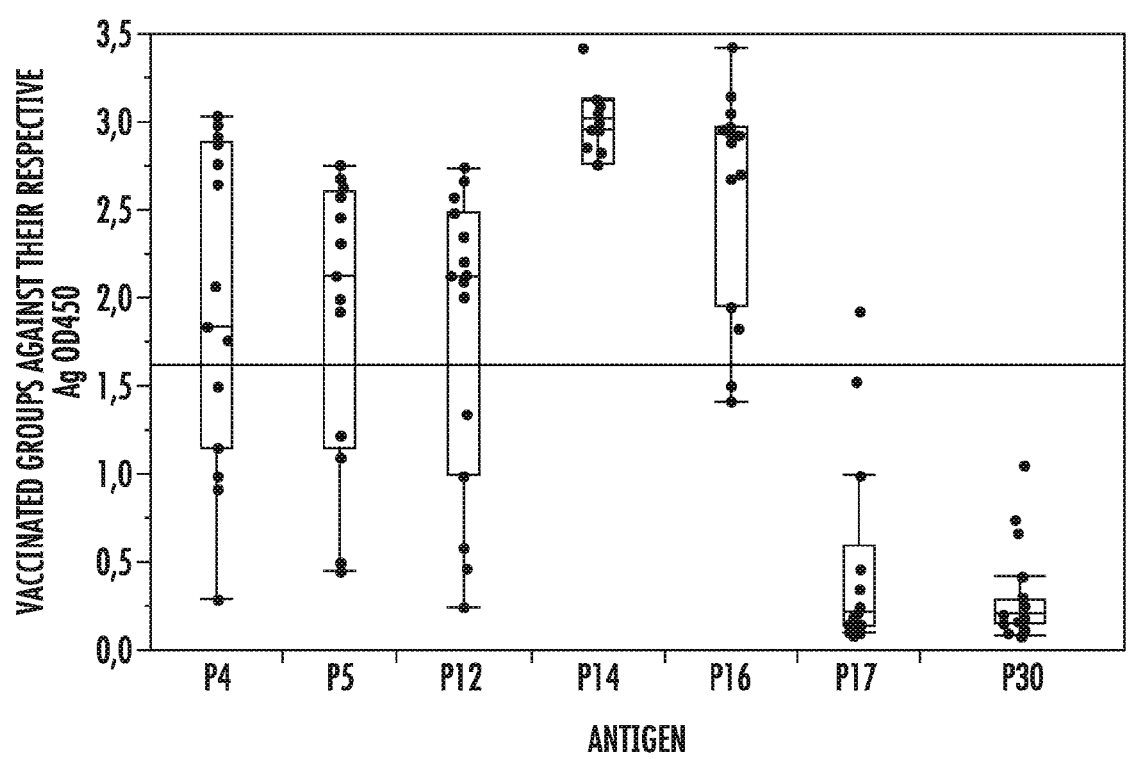
FIG. 21: ELISA results showing the antibody response in vaccinated groups against peptides P4, P5, P12, P14, P16, P17 and P30.
Figure 22:
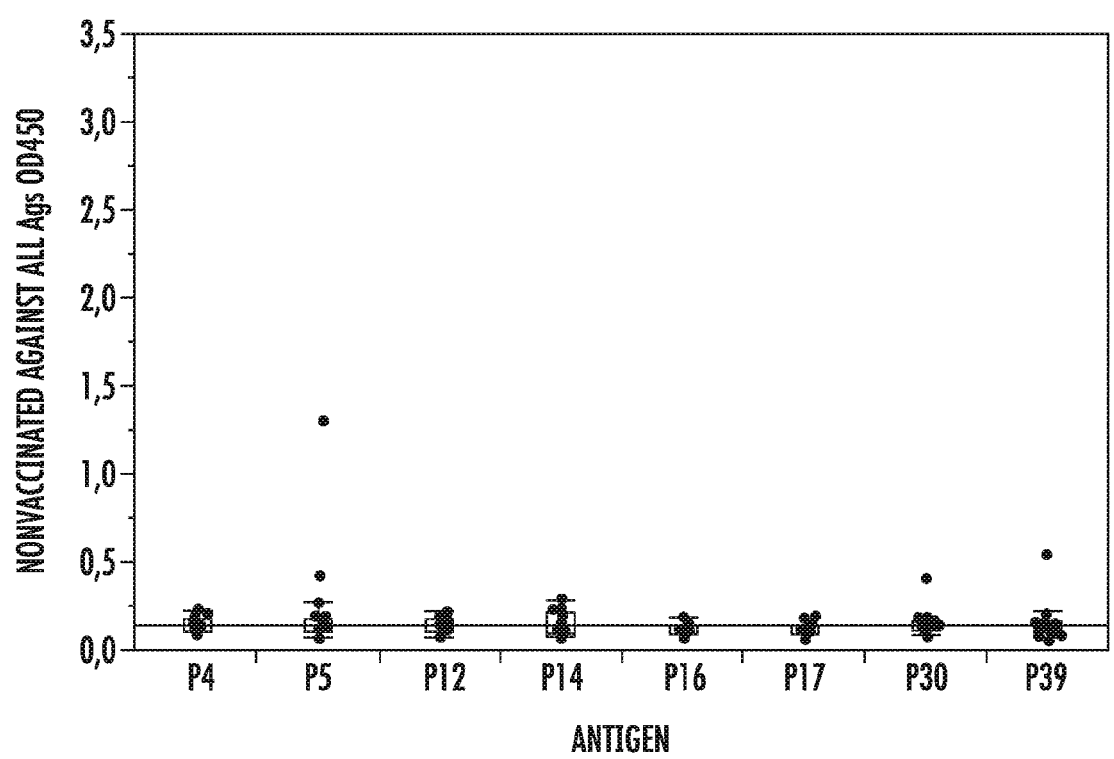
FIG. 22: ELISA results showing antibody response in unvaccinated groups.

Graphic representation of the data in Table 6 can be seen in FIGS. 21 and 22. FIG. 21 graphically depicts the antibody response in vaccinated groups against their respective serotype. FIG. 22 graphically represents the antibody response in the unvaccinated group against all antigens (the control for unspecific binding).

Groups vaccinated with P4, P5, P12, P14 and P16 antigens all showed a high mean antibody response against their respective antigens. The individual variation in antibody response varied between the individuals as expected in outbred Atlantic salmon. The individual variation in the group vaccinated with P14 was particularly low, with all individual fish showing very strong reactivity.

Groups vaccinated with P17 and P30 showed a response that on average was much weaker, and only a minority of individual fish had responded to vaccination. The unvaccinated group in general showed no reactivity to any of the antigens. The few individual fish having some reactivity could be related to cross-reactivity acquired from encounter with natural bacteria or some technical error/variation,

What is claimed is:

1. A vaccine composition for the control or prevention of an infestation of sea lice comprising an immunologically effective dose of a recombinant sea louse peptide and a pharmaceutically acceptable carrier, wherein the peptide has at least about 90% sequence identity to SEQ ID NO: 13, and further comprising a pharmaceutically acceptable adjuvant.

2. The vaccine of claim 1 wherein the sea louse is selected from the genus *Lepeophtheirus* or *Caligus*.

3. The vaccine of claim 2 wherein the sea louse comprises the genus *Lepeophtheirus* and comprises *Lepeophtheirus salmonis*.

4. The vaccine of claim 2 wherein the sea louse comprises the genus *Caligus* and comprises *Caligus rogercresseyi*.

5. The vaccine composition of wherein the peptide has at least about 95% sequence identity to SEQ ID NO: 13.

6. The vaccine of claim 5 wherein the peptide has at least about 95% sequence identity to SEQ ID NO: 13 and is a conservatively substituted variant thereof.

7. The vaccine composition of claim 1 wherein the adjuvants are selected from the group consisting of muramyl dipeptides, lipopolysaccharides, glucans, glycans, oil-in-water emulsion, Freund's adjuvant, acrylic acid polymers, and water-in-oil emulsion.

8. The vaccine composition of claim 7, wherein the adjuvant is water-in-oil emulsion.

9. The vaccine composition of claim 1, wherein in the peptide has at least 90 sequence identity to SEQ ID NO.13 and is a conservatively substituted variant thereof.

10. The vaccine composition of claim 1 further comprising one or more antigens obtained from bacteria, virus, fungus or parasites other than sea lice.

11. The vaccine composition of claim 10 wherein the one or more antigens are selected from the group consisting of *Piscirickettsias* sp. *Aeromonas* sp., *Vibrio* sp., *Listonella* sp., *Moritella viscosa, Photobacterium damsela, Flavobacterium* sp., *Yersinia* sp., *Renibacterium* sp., *Streptococcus* sp., *Lactococcus* sp., *Edwarsiella* sp., *Francisella* sp., *Pseudomonas* sp., *Nocardia* sp., Mycobacerium sp., Viral Hemorrhagic Septicemia Virus (VHSV), Infectious Hematopoietic Necrosis virus (IHNV), Infectious Pancreatic Necrosis Virus (IPNV), Spring Viremia of Carp (SVC), Channel Catfish Virus (CCV), Infectious Salmon Anaemia virus (ISAV), pancreatic disease virus (SPDV), Iridovirus, and heart and skeletal muscle inflammation virus (HSMIV), Piscine Myocarditis virus (PMCV), *Saprolegnia* Sp., *Branchiomyces sanguinis*, and *Branchiomyces demigrans* variants or immunogenic fragments thereof.

12. The vaccine composition of claim 1 further comprising one or more additional sea louse peptides.

13. The vaccine of claim 12 wherein the one or more additional recombinant sea louse peptides comprise a peptide that has at least 80% sequence identity to SEQ ID NO. 19.

14. A method of vaccinating a Salmonid to prevent or control a sea lice infestation comprising the administering of the vaccine of claim 1.

15. The method of claim 14, wherein the vaccine is administered by a route selected from the group of intraperitoneal injection, intramuscular injection, bath, immersion, and oral administration.

16. The method of claim 15, wherein the vaccine is administered by intraperitoneal injection.

* * * * *